(12) United States Patent
Martin et al.

(10) Patent No.: US 7,902,237 B2
(45) Date of Patent: Mar. 8, 2011

(54) HETEROCYCLIC COMPOUNDS AS PHARMACEUTICAL AGENTS

(75) Inventors: Richard Martin, San Diego, CA (US); Brenton Todd Flatt, Poway, CA (US); Jeffrey Dean Kahl, San Antonio, TX (US)

(73) Assignee: Exelixis, Inc., South San Francisco, CA (US)

(*) Notice: Subject to any disclaimer, the term of this patent is extended or adjusted under 35 U.S.C. 154(b) by 783 days.

(21) Appl. No.: 11/573,614

(22) PCT Filed: Aug. 9, 2005

(86) PCT No.: PCT/US2005/028357
§ 371 (c)(1),
(2), (4) Date: Aug. 3, 2007

(87) PCT Pub. No.: WO2006/020680
PCT Pub. Date: Feb. 23, 2006

(65) Prior Publication Data
US 2008/0132519 A1 Jun. 5, 2008

Related U.S. Application Data

(60) Provisional application No. 60/600,239, filed on Aug. 10, 2004.

(51) Int. Cl.
*A61K 31/426* (2006.01)
*C07D 277/04* (2006.01)

(52) U.S. Cl. ......... 514/370; 548/146; 548/184; 548/233; 548/300.1; 514/369; 514/374; 514/396

(58) Field of Classification Search .................. 548/146, 548/182, 184, 215, 233, 300.1; 514/365, 514/369, 370, 374, 396
See application file for complete search history.

(56) References Cited

U.S. PATENT DOCUMENTS

| | | | |
|---|---|---|---|
| 2,719,162 A | 9/1955 | Sawdey et al. | |
| 2,808,330 A | 10/1957 | Sawdey | |
| 3,097,100 A | 7/1963 | Lappin et al. | |
| 3,678,041 A | 7/1972 | Mousseron | |
| 5,198,454 A * | 3/1993 | Chiou | 514/369 |
| 5,750,712 A * | 5/1998 | Yoneda et al. | 548/186 |
| 6,353,006 B1 * | 3/2002 | Dixon et al. | 514/338 |
| 6,696,473 B2 | 2/2004 | Martin et al. | |
| 2003/0212111 A1 | 11/2003 | Martin et al. | |

FOREIGN PATENT DOCUMENTS

| | | |
|---|---|---|
| BE | 608 790 A1 | 4/1962 |
| DE | 15 45 766 A1 | 2/1970 |
| JP | 06-128234 A | 5/1994 |

OTHER PUBLICATIONS

Chiou et al (1993): STN International HCAPLUS database, (Columbus, Ohio), Accession No. 1993:440938.*
Okawara et al (1986): STN International HCAPLUS database, (Columbus, Ohio), Accession No. 1987:4932.*
Farghaly, A.M. et al., "Synthesis of Novel 2-Substituted Quinoline Derivatives: Antimicrobial, Inotropicand Chronotopic Activities", Archiv Der Pharmazie, 1990, vol. 323, 247-251.
Sahu, J. et al., "Studies on Thiazolidinones. Part-XV. Synthesis of Thiazolidinones from Mono- and Di-Substituted Thioureas Possessing Alicyclic and Heterocyclic Substituents", Journal of the Indian Chemical Society, 1985, 62(1), 71-73.
Dains, F.B. et al., "The Reactions of Formamidines. VIII. Some Thiazolidone Derivatives", Journal of the American Chemical Society, 1921. vol. 43, 613-618.
Dains, F.B. et al., "The Reactions of Formamidines. VI. Some Thiazole Derivatives", Journal of the American Chemical Society, 1916, vol. 38. 1841-1844.

* cited by examiner

*Primary Examiner* — Golam M Shameem
(74) *Attorney, Agent, or Firm* — McDonnell Boehnen Hulbert & Berghoff LLP

(57) ABSTRACT

Compounds, compositions and methods for modulating the activity of receptors are provided. In particular, compounds and compositions are provided for modulating the activity of receptors and for the treatment, prevention, or amelioration of one or more symptoms of the disease or disorder directly or indirectly related to the activity of the receptors.

21 Claims, No Drawings

HETEROCYCLIC COMPOUNDS AS PHARMACEUTICAL AGENTS

CROSS REFERENCE TO RELATED APPLICATION

This application is a US national phase of international application PCT/US2005/028357 filed on Aug. 9, 2005, which claims priority to U.S. Provisional Patent Application Ser. No. 60/600,239 filed on Aug. 10, 2004, the disclosure of which is incorporated herein by reference.

FIELD OF THE INVENTION

Compounds, compositions and methods are provided for modulating the activity of receptors and for the treatment, prevention, or amelioration of one or more symptoms of disease or disorder related to the activity of the receptors.

BACKGROUND OF THE INVENTION

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptor (PPAR)) and ecdysone, bind to HREs as heterodimers with a common partner, the retinoid X receptors (i.e., RXRs, also known as the 9-cis retinoic acid receptors; see, e.g., Levin et al. (1992) *Nature* 355:359-361 and Heyman et al., (1992) *Cell* 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841-850). The latter receptors, termed the class II nuclear receptor subfamily, include many which are established or implicated as important regulators of gene expression. There are three RXR genes (see, e.g., Mangelsdorf et al. (1992) *Genes Dev.* 6:329-344), coding for RXRα, -β, and -γ, all of which are able to heterodimerize with any of the class II receptors, although there appear to be preferences for distinct RXR subtypes by partner receptors in vivo (see, e.g., Chiba et al. (1997) *Mol. Cell. Biol.* 17:3013-3020). In the adult liver, RXRα is the most abundant of the three RXRs (see, e.g., Mangelsdorf et al. (1992) *Genes Dev.* 6:329-344), suggesting that it might have a prominent role in hepatic functions that involve regulation by class II nuclear receptors. See also, Wan et al. (2000) *Mol. Cell. Biol.* 20:4436-4444.

Orphan Nuclear Receptors

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for FXR (infra).

Since it is known that products of intermediary metabolism act as transcriptional regulators in bacteria and yeast, such molecules may serve similar functions in higher organisms (see, e.g., Tomkins (1975) *Science* 189:760-763 and O'Malley (1989) *Endocrinology* 125:1119-1120). For example, one biosynthetic pathway in higher eukaryotes is the mevalonate pathway, which leads to the synthesis of cholesterol, bile acids, porphyrin, dolichol, ubiquinone, carotenoids, retinoids, vitamin D, steroid hormones and farnesylated proteins.

FXR

FXR (originally isolated as RIP14 (retinoid X receptor-interacting protein-14), see, e.g., Seol et al., (1995) *Mol. Endocrinol.* 9:72-85) is a member of the nuclear hormone receptor superfamily and is primarily expressed in the liver, kidney and intestine (see, e.g., Seol et al., supra and Forman et al., (1995) *Cell* 81:687-693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (see, e.g., Makishima et al. (1999) *Science* 284: 1362-1365, Parks et al. (1999) *Science* 284:1365-1368, Wang et al. (1999) *Mol. Cell.* 3:543-553), which serve to inhibit cholesterol catabolism. See also, Urizar et al. (2000) *J. Biol. Chem.* 275:39313-39317.

LXRα and LXRβ

LXRα is found predominantly in the liver, with lower levels found in kidney, intestine, spleen and adrenal tissue (see, e.g., Willy, et al. (1995) *Gene Dev.* 9(9):1033-1045). LXRβ, also known as UR (ubiquitous receptor), is ubiquitous in mammals and was found in nearly all tissues examined. LXRs are activated by certain naturally occurring, oxidized derivatives of cholesterol (see, e.g., Lehmann, et al. (1997) *J. Biol. Chem.* 272(6):3137-3140). LXRα is activated by oxy-cholesterol and promotes cholesterol metabolism (Peet et al. (1998) *Cell* 93:693-704). Thus, LXRs appear to play a role in, e.g., cholesterol metabolism (see, e.g., Janowski, et al. (1996) *Nature* 383:728-731).

Nuclear Receptors and Disease

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,5103), hyperlipoproteinemia (see, e.g., International Patent Application Publication No. WO 01/60818), hypertriglyceridemia, lipodystrophy, peripheral occlusive disease, ischemic stroke, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g., U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see, e.g., International Patent Application Publication No. WO 00/17334).

Activity of nuclear receptors, including FXR, LXRs and/or orphan nuclear receptors, has been implicated in physiological processes including, but not limited to, bile acid biosynthesis, cholesterol metabolism or catabolism, and modulation of cholesterol 7α-hydroxylase gene (CYP7A1) transcription (see, e.g., Chiang et al. (2000) *J. Biol. Chem.* 275:10918-10924), HDL metabolism (see, e.g., Urizar et al. (2000) *J. Biol. Chem.* 275:39313-39317), hyperlipidemia, cholestasis, and increased cholesterol efflux and increased expression of ATP binding cassette transporter protein (ABC1) (see, e.g., International Patent Application Publication No. WO 00/78972).

Thus, there is a need for compounds, compositions and methods of modulating the activity of nuclear receptors, including FXR, LXRs and/or orphan nuclear receptors. Such compounds are useful in the treatment, prevention, or amelioration of one or more symptoms of diseases or disorders in which nuclear receptor activity is implicated.

SUMMARY OF THE INVENTION

Compounds for use in compositions and methods for modulating the activity of nuclear receptors are provided. In particular, compounds for use in compositions and methods for modulating farnesoid X receptor (FXR), liver X receptors (LXRα and LXRβ) and/or orphan nuclear receptors, are provided. In certain embodiments, the compounds are heterocyclic compounds that are substituted with a heterocyclylene group and an imine moiety. In one embodiment, the compounds provided herein are agonists of FXR and/or LXR. In another embodiment, the compounds provided herein are antagonists of FXR and/or LXR. Agonists that exhibit low efficacy are, in certain embodiments, antagonists.

In one embodiment, the compounds for use in the compositions and methods provided herein have formulae I:

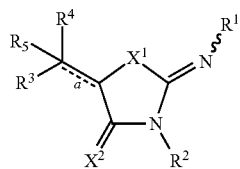

or a pharmaceutically acceptable derivative thereof, wherein:
bond a is a single bond or double bond;
$X^1$ is $NR^6$, O or $S(O)_t$;
$X^2$ is S or O;
$R^1$ is optionally substituted alkyl, optionally substituted alkenyl or optionally substituted alkynyl, all or which, when substituted, are substituted with one to five substituents each independently selected from the group consisting of cyano, nitro, halo, pseudohalo, —$OR^{10}$, —$SR^{16}$, —$N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$—$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, —$Si(R^{14})_3$, —$N(R^{10})S(O)_tR^{15}$ and —$R^9$—$S(O)_tR^{15}$;
or $R^1$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$;
or $R^1$ is —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$N(R^{10})C(J)R^{13}$, —$R^9$—$N(R^{10})C(J)OR^{10}$, —$R^9$—$S(O)_tR^{15}$ or —$R^9$—$N(R^{10})C(J)N(R^{11})(R^{12})$;

$R^2$ is optionally substituted alkyl, optionally substituted alkenyl, optionally substituted alkynyl, all or which, when substituted, are substituted with one to five substituents from the group consisting of cyano, nitro, halo, pseudohalo, —$OR^{10}$, —$SR^{16}$, —$N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$, —$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, —$Si(R^{14})_3$, —$N(R^{10})S(O)_tR^{15}$ and —$S(O)_tR^{15}$;
or $R^2$ is optionally substituted cycloalkyl, optionally substituted cycloalkylalkyl, optionally substituted heterocyclyl, optionally substituted heterocyclylalkyl, optionally substituted aryl, optionally substituted heteroaryl, optionally substituted aralkyl, optionally substituted heteroaralkyl or optionally substituted aryl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R_{10})C(J)N(R^{11})(R^{12})$, —$R^9$—$OC(J)R^{13}$, —$R^9$—$OC(J)OR^{10}$, $R^9$—$OC(J)N(R^{11})(R^{12})$, —$Si(R^{14})_3$, —$N(R^{10})S(O)_tR^{15}$ and —$R^9$—$S(O)_tR^{15}$;
or $R^2$ is —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$N(R^{11})(R^{12})$ or —$R^9$—$S(O)_tR^{15}$;

$R^3$, $R^4$ and $R^5$ are each independently selected as in (a), (b) or (c) as follows:
(a) $R^3$, $R^4$ and $R^5$ are each independently optionally substituted alkyl, optionally substituted alkenyl or optionally substituted alkynyl, all of which, when substituted are substituted with cyano, nitro, halo, pseudohalo, —$OR^{10}$, —$SR^{16}$, $N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$, —$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, $Si(R^{14})_3$, —$N(R^{10})S(O)_tR^{15}$ and —$S(O)_tR^{15}$;
or (b) $R^3$, $R^4$ and $R^5$ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, $R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—OC(J)$R^{13}$, —$R^9$—C(J)O$R^{10}$, —$R^9$—OC(J)N($R^{11}$)($R^{12}$), —Si($R^{14}$)$_3$, —N($R^{10}$)S(O)$_t R^{15}$ and —$R^9$—S(O)$_t R^{15}$;

or (c) $R^3$, $R^4$ and $R^5$ are each independently selected from a group consisting of hydrogen, halo, —N($R^7$)($R^8$), —N($R^{10}$)C(J)$R^{13}$, —N($R^{10}$)C(J)O$R^{10}$, —$R^9$—C(J)$R^{13}$, —N($R^{10}$)C(J)N($R^{11}$)($R^{12}$) and —N($R^{10}$)S(O)$_t R^{15}$;

provided that $R^5$ is present only when bond a is a single bond;

and further provided that:

when $R^3$, $R^4$ or $R^5$ is cycloalkylalkyl or —N($R^7$)($R^8$) and bond a is a single bond, then $R^1$ is phenyl substituted with at least two different substituents selected from the following: cyano, —$R^9$—C(J)$R^{13}$, —$R^9$—C(J)O$R^{10}$, —$R^9$—C(J)N($R^{11}$)($R^{12}$), —$R^9$—C(J)N($R^{10}$)N($R^{12}$)$R^{13}$, —$R^9$—N($R^{10}$)C(J)O$R^{10}$, —$R^9$—N($R^{10}$)C(J)N($R^{11}$)($R^{12}$), —N($R^{10}$)S(O)$_t R^{13}$, —$R^9$—N($R^{10}$)C(J)$R^{13}$ and —$R^9$—N($R^{11}$)($R^{12}$);

or when $R^3$, $R^4$ or $R^5$ is alkyl, alkenyl, alkynyl, halo, haloalkyl, cycloalkyl, heterocyclylalkyl, aralkyl, —$R^9$—C(J)$R^{13}$, —$R^9$—C(J)O$R^{10}$, —$R^9$—S(O)$_t R^{15}$, aryl or heteroaryl, then $R^1$ is phenyl and $R^1$ is substituted with at least two different substituents selected from the following: cyano, —$R^9$—C(J)$R^{13}$, —$R^9$—C(J)O$R^{10}$, —$R^9$—C(J)N($R^{11}$)($R^{12}$), —$R^9$—C(J)N($R^{10}$)N($R^{12}$)$R^{13}$, —$R^9$—N($R^{10}$)C(J)O$R^{10}$, —$R^9$—N($R^{10}$)C(J)N($R^{11}$)($R^{12}$), —N($R^{10}$)S(O)$_t R^{13}$, —$R^9$—N($R^{10}$)C(J)$R^{13}$, and —$R^9$—N($R^{11}$)($R^{12}$);

and further provided that $R^3$, $R^4$ and $R^5$ are not all hydrogen;

$R^6$ is hydrogen, alkyl, alkenyl, alkynyl, aryl, heteroaryl, cycloalkyl, heterocyclyl, aralkyl, heteroaralkyl, —$R^9$—S(O)$_t R^{15}$, —$R^9$—C(J)$R^{13}$, —$R^9$—C(J)O$R^{10}$ or —$R^9$—C(J)N($R^{11}$)($R^{12}$);

$R^7$ and $R^3$ each independently selected as in (a), (b) or (c) as follows:

(a) $R^7$ and $R^8$ are each independently optionally substituted alkyl, optionally substituted alkenyl or optionally substituted alkynyl, all of which, when substituted, are substituted with one to three substituents from the group consisting of cyano, nitro, halo, pseudohalo, —O$R^{10}$, —S$R^{16}$, —N($R^{11}$)($R^{12}$), —O$R^{16}$O$R^{10}$, —C(J)$R^{13}$, —C(J)O$R^{10}$, —C(J)N($R^{11}$)($R^{12}$), —C(J)N($R^{10}$)N($R^{11}$)($R^{12}$), —N($R^{10}$)C(J)$R^{13}$, —N($R^{10}$)C(J)O$R^{10}$, —N($R^{10}$)C(J)N($R^{11}$)($R^{12}$), OC(J)$R^{13}$, —OC(J)O$R^{10}$, —OC(J)N($R^{11}$)($R^{12}$), —Si($R^{14}$)$_3$, —N($R^{10}$)S(O)$_t R^{15}$ and —S(O)$_t R^{15}$;

or (b) $R^7$ and $R^3$ are each independently is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—O$R^{10}$, —$R^9$—O$R^{16}$O$R^{10}$, —$R^9$—S$R^{16}$, —$R^9$—N($R^{11}$)($R^{12}$), —$R^9$—C(J)$R^{13}$, —$R^9$—C(J)O$R^{10}$, —$R^9$—C(J)N($R^{11}$)($R^{12}$), —$R^9$—N($R^{10}$)C(J)$R^{13}$, —$R^9$—N($R^{10}$)C(J)O$R^{10}$, —$R^9$—N($R^{10}$)C(J)N($R^{11}$)($R^{12}$), —$R^9$—C(J)N($R^{10}$)N($R^{11}$)($R^{12}$), —$R^9$—OC(J)$R^{13}$, —$R^9$—OC(J)O$R^{10}$, —$R^9$—OC(J)N($R^{11}$)($R^{12}$), —Si($R^{14}$)$_3$, —N($R^{10}$)S(O)$_t R^{15}$ and —$R^9$—S(O)$_t R^{15}$;

or (c) $R^7$ and $R^8$ are each independently hydrogen, —C(J)$R^{13}$, —C(J)O$R^{10}$, —C(J)N($R^{11}$)($R^{12}$), —N($R^{10}$)C(J)O$R^{10}$ or —S(O)$_t R^{15}$ provided, however, that both $R^7$ and $R^8$ cannot be hydrogen;

or $R^7$ and $R^8$ together with the nitrogen atom to which they are attached, form an optionally substituted heterocyclyl or an optionally substituted heteroaryl, either of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—O$R^{10}$, $R^9$—O$R^{16}$O$R^{10}$, —$R^9$—S$R^{16}$, —$R^9$—N($R^{11}$)($R^{12}$), —$R^9$—C(J)$R^{13}$, —$R^9$—C(J)O$R^{10}$, —$R^9$—C(J)N($R^{11}$)($R^{12}$), —$R^9$—C(J)N($R^{10}$)N($R^{11}$)($R^{12}$), —$R^9$—N($R^{10}$)C(J)$R^{13}$, —$R^9$—N($R^{10}$)C(J)O$R^{10}$, —$R^9$—N($R^{10}$)C(J)N($R^{11}$)($R^{12}$), —$R^9$—OC(J)$R^{13}$, —$R^9$—OC(J)O$R^{10}$, —$R^9$—OC(J)N($R^{11}$)($R^{12}$), —Si($R^{14}$)$_3$, —N($R^{10}$)S(O)$_t R^{15}$ and —S(O)$_t R^{15}$;

each $R^9$ is independently a direct bond or a straight or branched alkylene chain;

$R^{10}$ and $R^{13}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{11}$ and $R^{12}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{11}$ and $R^{12}$ together with the nitrogen atom to which they are attached, form a heterocyclyl, heterocyclylalkenyl, or heteroaryl;

$R^{14} R^{15}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each t is independently 0 to 2.

Also of interest are any pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutical compositions formulated for administration by an appropriate route and means containing effective concentrations of one or more of the compounds provided herein, or pharmaceutically acceptable derivatives thereof, that deliver amounts effective for the treatment, prevention, or amelioration of one or more symptoms of diseases or disorders that are modulated or otherwise affected by nuclear receptor activity, including FXR, LXR and/or orphan nuclear receptor activity, or in which nuclear receptor activity, including FXR, LXR and/or orphan nuclear receptor activity, is implicated, are also provided. The effective amounts and concentrations are effective for ameliorating any of the symptoms of any of the diseases or disorders.

Methods for treatment, prevention, or amelioration of one or more symptoms of diseases or disorders mediated by or in which nuclear receptor activity, including FXR, LXR and/or orphan nuclear receptor activity, is implicated, are provided.

Such methods include methods of treatment, prevention and amelioration of one or more symptoms of hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, or cardiovascular disorders, using one or more of the compounds provided herein, or pharmaceutically acceptable derivatives thereof.

Methods of modulating the activity of nuclear receptors, including FXR, LXR and/or orphan nuclear receptors, using the compounds and compositions provided herein are also provided. The compounds and compositions provided herein are active in assays that measure the activity of nuclear receptors, including FXR, LXR and/or orphan nuclear receptors, including the assays provided herein. These methods include inhibiting and up-regulating the activity of nuclear receptors, including FXR, LXR and/or orphan nuclear receptors.

Methods of reducing cholesterol levels in a subject in need thereof by administration of one or more compounds or compositions provided herein are also provided.

Methods of modulating cholesterol metabolism using the compounds and compositions provided herein are provided.

Methods of treating, preventing, or ameliorating one or more symptoms of diseases or disorders which are affected by cholesterol, triglyceride, or bile acid levels by administration of one or more of the compounds and compositions provided herein are also provided.

In practicing the methods, effective amounts of the compounds or compositions containing therapeutically effective concentrations of the compounds, which are formulated for systemic delivery, including parenteral, oral, or intravenous delivery, or for local or topical application, for the treatment of nuclear receptor, including FXR, LXR and/or orphan nuclear receptor, mediated diseases or disorders, or diseases or disorders in which nuclear receptor activity, including FXR, LXR and/or orphan nuclear receptor activity, is implicated, including, but not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneform skin conditions, diabetes, Parkinson's disease; cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, or cardiovascular disorders, are administered to an individual exhibiting the symptoms of these diseases or disorders. The amounts are effective to ameliorate or eliminate one or more symptoms of the diseases or disorders.

Articles of manufacture containing packaging material, a compound or composition, or pharmaceutically acceptable derivative thereof, provided herein, which is effective for modulating the activity of nuclear receptors, including FXR, LXR and/or orphan nuclear receptors, or for treatment, prevention or amelioration of one or more symptoms of nuclear receptor, including FXR, LXR and/or orphan nuclear receptor, mediated diseases or disorders, or diseases or disorders in which nuclear receptor activity, including FXR, LXR and/or orphan nuclear receptor activity, is implicated, within the packaging material, and a label that indicates that the compound or composition, or pharmaceutically acceptable derivative thereof, is used for modulating the activity of nuclear receptors, including FXR, LXR and/or orphan nuclear receptors, or for treatment, prevention or amelioration of one or more symptoms of nuclear receptor, including FXR, LXR and/or orphan nuclear receptor, mediated diseases or disorders, or diseases or disorders in which nuclear receptor activity, including FXR, LXR and/or orphan nuclear receptor activity, is implicated, are provided.

DETAILED DESCRIPTION OF EMBODIMENTS

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, a nuclear receptor is a member of a superfamily of regulatory proteins that are receptors for, e.g., steroids, retinoids, vitamin D and thyroid hormones. These proteins bind to cis-acting elements in the promoters of their target genes and modulate gene expression in response to a ligand therefor. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors are FXR and LXR.

As used herein, an orphan nuclear receptor is a nuclear receptor for which the natural ligand is unknown.

As used herein, farnesoid X receptor or FXR refers to a nuclear receptor as described in U.S. Pat. No. 6,005,086.

As used herein, liver X receptor or LXR or UR refers to a nuclear receptor implicated in cholesterol homeostasis. As used herein, the term LXR refers to both LXRα and LXRβ, two forms of the protein found in mammals. Liver X receptor-α or LXRα refers to the receptor described in U.S. Pat. No. 5,757,661 and Willy et al. (1995) *Gene Dev.* 9(9):1033-1045. Liver X receptor-β or LXRβ refers to the receptor described in Peet et al. (1998) *Curr. Opin. Genet. Dev.* 8(5): 571-575; Song et al. (1995) *Ann. N.Y. Acad. Sci.* 761:38-49; Alberti et al. (2000) *Gene* 243(1-2):93-103; and references cited therein.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxy-methyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a nuclear receptor, including FXR, LXR and/or orphan nuclear receptor, mediated diseases or disorders, or diseases or disorders in which nuclear receptor activity, including FXR, LXR and/or orphan nuclear receptor activity, is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, the term agonist refers to an agent which produces activation of a nuclear receptor and provides for a substantial increase in binding of one or more coactivator protein(s) to nuclear receptor, and relieves binding of one or more corepressors to the nuclear receptor.

As used herein the term antagonist refers to an agent which opposes the agonist activity of a known agonist of the nuclear receptor LBD, or enhances or stabilizes binding of a co-repressor protein to a nuclear receptor and inhibits binding of one or more coactivators to the nuclear receptor.

As used herein, the $IC_{50}$ refers to an amount, concentration or dosage of a particular test compound that achieves a 50% inhibition of a maximal response, such as modulation of FXR activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form. It is also to be understood that the compounds provided herein may include both the E and Z configuration around the double bond.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-penytyl and isohexyl. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. Examples of such heterocyclyl radicals include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl; carbazolyl, cinnolinyl, dioxolanyl, dibenzofuranyl, decahydroisoquinolyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thiophenyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$, where t is 0 to 2 and where each J and each $R^9$-$R^{15}$ are as defined above in the Summary of the Invention.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a heterocyclyl radical as defined above which is aromatic. Examples include, but are not limited to, pyridinyl, furanyl, thiophenyl, benzofuranyl, benzothiophenyl, and pyrrolyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$; —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$, where t is 0 to 2 and where each J and each $R^9$-$R^{15}$ are as defined above in the Summary of the Invention.

As used herein, a "heteroarylium" group is a heteroaryl group that is positively charged on one or more of the heteroatoms.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —$S(O)_2$—.
As used herein, "sulfo" refers to —$S(O)_2O$—.

As used herein, "carboxy" refers to a divalent radical, —C(O)O—.

As used herein, "aminocarbonyl" refers to —$C(O)NH_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NRCOR in which R' and R are independently alkyl, including lower alkyl.

As used herein, "diarylaminocarbonyl" refers to —C(O)NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O) NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

Where the number of any given substituent is not specified (e.g., "haloalkyl"), there may be one or more substituents present. For example, "haloalkyl" may include one or more of the same or different halogens. As another example, "C$_{1-3}$ alkoxyphenyl" may include one or more of the same or different alkoxy groups containing one, two or three carbons.

As used herein, the following terms have their accepted meaning in the chemical literature:

| | |
|---|---|
| AcOH | acetic acid |
| CHCl$_3$ | chloroform |
| conc | concentrated |
| DBU | 1,8-diazabicyclo[5.4.0]undec-7-ene |
| DCM | dichloromethane |
| DME | 1,2-dimethoxyethane |
| DMF | N,N-dimethylformamide |
| DMSO | dimethylsulfoxide |
| EtOAc | ethyl acetate |
| EtOH | ethanol (100%) |
| Et$_2$O | diethyl ether |
| Hex | hexanes |
| H$_2$SO$_4$ | sulfuric acid |
| MeCN | acetonitrile |
| MeOH | methanol |
| Pd/C | palladium on activated carbon |
| TEA | triethylamine |
| THF | tetrahydrofuran |
| TFA | trifluoroacetic acid |
| TMOF | trimethyl orthoformate |

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Preferred Embodiments of the Compounds of the Invention

Compounds for use in compositions and methods for modulating the activity of nuclear receptors are provided. In particular, compounds for use in compositions and methods for modulating farnesoid X receptor (FXR), liver X receptors (LXRα and LXRβ) and/or orphan nuclear receptors, are provided.

The present invention provides compounds represented by the formula (I):

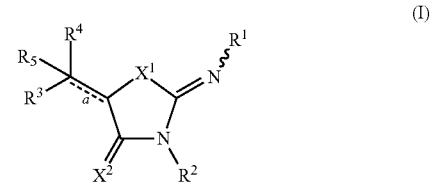

In formula (I), the letter $X^1$ represents $NR^6$, O or $S(O)_t$ where subscript t is an integer from 0 to 2 and the letter $X^2$ represents S or O. The letter "a" represents a bond which may be a single bond or a double bond. The symbol $R^1$ represents optionally substituted alkyl, optionally substituted alkenyl or optionally substituted alkynyl, all of which, when substituted, are substituted with one to five substituents from the group consisting of cyano, nitro, halo, pseudohalo, —OR$^{10}$, —SR$^{16}$, —N(R$^{11}$)(R$^{12}$), —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_t$R$^{15}$ and —R$^9$—S(O)$_t$R$^{15}$. Alternatively, R$^1$ represents optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, is substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{10}$)(R$^{12}$), —Si(R$^{14}$)$_3$, —N(R$^{10}$)S(O)$_t$R$^{15}$ and —R$^9$—S(O)$_t$R$^{15}$. Alternatively, R$^1$ represents —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—N(R$^{10}$)C(J)R$^{13}$, —R$^9$—N(R$^{10}$)C(J)OR$^{10}$, —R$^9$—S(O)$_t$R$^{15}$ or —R$^9$—N(R$^{10}$)C(J)N(R$^{11}$)(R$^{12}$).

The symbol $R^2$ represents optionally substituted alkyl, optionally substituted alkenyl, optionally substituted alkynyl, all of which, when substituted, are substituted with one to five substituents from the group consisting of cyano, nitro, halo, pseudohalo, —OR$^{10}$, —SR$^{16}$, —N(R$^{11}$)(R$^{12}$), —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_t$R$^{15}$ and —S(O)$_t$R$^{15}$.

Alternatively, R$^2$ represents optionally substituted cycloalkyl, optionally substituted cycloalkylalkyl, optionally substituted heterocyclyl, optionally substituted heterocyclylalkyl, optionally substituted aryl, optionally substituted heteroaryl, optionally substituted aralkyl or optionally substituted heteroaralkyl, and optionally substituted aryl, which, when substituted, is substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)

$C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-R^9-S(O)_tR^{15}$.

Alternatively, $R^2$ is $-R^9-C(J)R^{13}$, $-R^9-C(J)OR^{10}$, $-R^9-C(J)N(R^{11})(R^{12})$, $-R^9-C(J)N(R^{10})N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-N(R^{11})(R^{12})$ or $-R^9-S(O)_tR^{15}$.

The symbols $R^3$, $R^4$ and $R^5$ are each independently selected from (a), (b) or (c) as follows:

(a) $R^3$, $R^4$ and $R^5$ are each independently optionally substituted alkyl, optionally substituted alkenyl, optionally substituted alkynyl, all of which, when substituted is substituted with cyano, nitro, halo, pseudohalo, $-OR^{10}$, $-SR^{16}$, $-N(R^{11})(R^{12})$, $-C(J)R^{13}$, $-C(J)OR^{10}$, $-C(J)N(R^{11})(R^{12})$, $-C(J)N(R^{10})N(R^{11})(R^{12})$, $-N(R^{10})C(J)R^{13}$, $-N(R^{10})C(J)OR^{10}$, $-N(R^{10})C(J)N(R^{11})(R^{12})$, $-OC(J)R^{13}$, $-OC(J)OR^{10}$, $-OC(J)N(R^{11})(R^{12})$, $-Si(R^{14})_3$, $-N(R^{10})S(O)_tR^{15}$ and $-S(O)_tR^{15}$;

or (b) $R^3$, $R^4$ and $R^5$ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, all of which, when substituted, is substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-R^9-S(O)_tR^{15}$;

or (c) $R^3$, $R^4$ and $R^5$ are each independently selected from a group consisting of hydrogen, halo, $-N(R^7)(R^8)$, $-N(R^{10})C(J)R^{13}$, $-N(R^{10})C(J)OR^{10}$, $-R^9-C(J)R^{13}$, $-N(R^{10})C(J)N(R^{11})(R^{12})$ and $-N(R^{10})S(O)_tR^{15}$;

provided that $R^5$ is present only when bond a is a single bond;

and further provided that:

when $R^3$, $R^4$ or $R^5$ is cycloalkylalkyl or $-N(R^7)(R^8)$ and bond a is a single bond, then $R^1$ is phenyl substituted with at least two different substituents selected from the following: cyano, $-R^9-C(J)R^{13}$, $-R^9-C(J)OR^{10}$, $-R^9-C(J)N(R^{11})(R^{12})$, $-R^9-C(J)N(R^{10})N(R^{12})R^{13}$, $-R^9-N(R^{10})C(J)OR^{10}$, $-R^9-N(R^{10})C(J)N(R^{11})(R^{12})$, $-N(R^{10})S(O)_tR^{13}$, $-R^9-N(R^{10})C(J)R^{13}$, and $-R^9-N(R^{11})(R^{12})$;

or when $R^3$, $R^4$ or $R^5$ is alkyl, alkenyl, alkynyl, halo, haloalkyl, cycloalkyl, heterocyclylalkyl, aralkyl, $-R^9-C(J)R^{13}$, $-R^9-C(J)OR^{10}$, $-R^9-S(O)_tR^{15}$, aryl or heteroaryl, then $R^1$ is phenyl and $R^1$ is substituted with at least two different substituents selected from the following: cyano, $-R^9-C(J)R^{13}$, $-R^9-C(J)OR^{10}$, $-R^9-C(J)N(R^{11})(R^{12})$, $-R^9-C(J)N(R^{10})N(R^{12})R^{13}$, $-R^9-N(R^{10})C(J)OR^{10}$, $-R^9-N(R^{10})C(J)N(R^{11})(R^{12})$, $-N(R^{10})S(O)_tR^{13}$, $-R^9-N(R^{10})C(J)R^{13}$, and $-R^9-N(R^{11})(R^{12})$;

and further provided that $R^3$, $R^4$ and $R^5$ are not all hydrogen.

The symbol $R^6$ represents hydrogen, alkyl, alkenyl, alkynyl, aryl, heteroaryl, cycloalkyl, heterocyclyl, aralkyl, heteroaralkyl, $-R^9-S(O)_tR^{15}$, $-R^9-C(J)R^{13}$, $-R^9-C(J)OR^{10}$ or $-R^9-C(J)N(R^{11})(R^{12})$.

The symbol $R^7$ represents optionally substituted alkyl, optionally substituted alkenyl or optionally substituted alkynyl, all of which, when substituted, is substituted with one to three substituents from the group consisting of cyano, nitro, halo, pseudohalo, $-OR^{10}$, $-SR^{16}$, $N(R^{11})(R^{12})$, $-OR^{16}OR^{10}$, $-C(J)R^{13}$, $-C(J)OR^{10}$, $-C(J)N(R^{11})(R^{12})$, $-C(J)N(R^{10})N(R^{11})(R^{12})$, $-N(R^{10})C(J)R^{13}$, $-N(R^{10})C(J)OR^{10}$, $N(R^{10})C(J)N(R^{11})(R^{12})$, $-OC(J)R^{13}$, $-OC(J)OR^{10}$, $-OC(J)N(R^{11})(R^{12})$, $-Si(R^{14})_3$, $-N(R^{10})S(O)_tR^{15}$ and $-S(O)_tR^{15}$.

Alternatively, $R^7$ represents optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, is substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-OR^{16}OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})$, $R^9-N(R^{10})C(J)R^{13}$, $-R^9-N(R^{10})C(J)OR^{10}$, $-R^9-N(R^{10})C(J)N(R^{11})(R^{12})$, $-R^9-C(J)N(R^{10})N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-R^9-S(O)_tR^{15}$.

Alternatively, $R^7$ represents hydrogen, $-C(J)R^{13}$, $C(J)OR^{10}$, $-C(J)N(R^{11})(R^{12})$, $-N(R^{10})C(J)OR^{10}$ or $-S(O)_tR^{15}$.

The symbol $R^8$ represents optionally substituted alkyl, optionally substituted alkenyl, optionally substituted alkynyl, all of which, when substituted, are substituted with one to three substituents from the group consisting of cyano, nitro, halo, pseudohalo, $-OR^{10}$, $-SR^{16}-N(R^{11})(R^{12})$, $-OR^{16}OR^{10}$, $-C(J)R^{13}$, $-C(J)OR^{10}$, $-C(J)N(R^{11})(R^{12})$, $-C(J)N(R^{10})N(R^{11})(R^{12})$, $-N(R^{10})C(J)R^{13}$, $-N(R^{10})C(J)OR^{10}$, $-N(R^{10})C(J)N(R^{11})(R^{12})-OC(J)R^{13}$, $-OC(J)OR^{10}$, $-OC(J)N(R^{11})(R^{12})$, $-Si(R^{14})_3$, $-N(R^{10})S(O)_tR^{15}$ and $-S(O)_tR^{15}$.

Alternatively, $R^8$ represents optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-OR^{16}OR^{10}$, $-R^9-SR^{10}$, $-R^9-N(R^{11})(R^{12})$, $-R^9-C(J)R^{13}$, $-R^9-C(J)OR^{10}$, $-R^9-C(J)N(R^{11})(R^{12})$, $-R^9-C(J)N(R^{10})N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-S(O)_tR^{15}$.

Alternatively, $R^8$ represents hydrogen, $-C(J)R^{13}$, $-C(J)OR^{10}$, $-C(J)N(R^{11})(R^{12})$, $-N(R^{10})C(J)OR^{10}$, $-N(R^{10})C(J)N(R^{11})(R^{12})$ or $-S(O)_tR^{15}$, provided, however, that both $R^7$ and $R^8$ cannot be hydrogen.

Alternatively, $R^7$ and $R^8$ together with the nitrogen atom to which they are attached, form an optionally substituted heterocyclyl or an optionally substituted heteroaryl, either of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-OR^{16}OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})-R^9-C(J)N(R^{10})N(R^{11})(R^{12})-$ $R^9-N(R^{10})C(J)R^{13}$, $-R^9-N(R^{10})C(J)OR^{10}$, $-R^9-N$ $(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-S(O)_tR^{15}$.

For the embodiments above, each $R^9$ is independently a direct bond or a straight or branched alkylene chain;

$R^{10}$ and $R^{13}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{11}$ and $R^{12}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{11}$ and $R^{12}$ together with the nitrogen atom to which they are attached, form a heterocyclyl, heterocyclylalkenyl, or heteroaryl;

$R^{14}$ $R^{15}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each t is independently 0 to 2.

A number of preferred embodiments are provided herein. For example, in one preferred embodiment, the compound is represented by the formula (II):

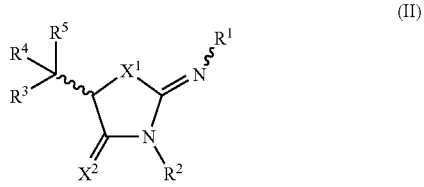

or a pharmaceutically acceptable derivative thereof, wherein $X^1$, $X^2$ and $R^1$-$R^5$ are as described in the Summary of the Invention.

In a further preferred embodiment, the compound is represented by formula (II), wherein $X^1$ is S; $X^2$ is O;

$R^1$ is optionally substituted cycloalkyl, optionally substituted heterocyclyl, optionally substituted aryl or optionally substituted heteroaryl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})$, $-R^9-C(J)N(R^{10})N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-R^9-S(O)_tR^{15}$;

$R^2$ is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-SR^{10}$ and $-R^9-N(R^{11})(R^{12})$; and $R^3$, $R^4$ and $R^5$ are each independently selected as in (a), (b) or (c) as follows:

(a) $R^3$, $R^4$ and $R^5$ are each independently optionally substituted alkyl or optionally substituted alkenyl, either of which, when substituted is substituted with cyano, nitro, halo, pseudohalo, $-OR^{10}$, $-SR^{16}$, $-N(R^{11})(R^{12})$, $-C(J)R^{13}$, $-C(J)OR^{10}$, $-C(J)N(R^{11})(R^{12})$, $-C(J)N(R^{10})N(R^{11})(R^{12})$, $-N(R^{10})C(J)R^{13}$, $-N(R^{10})C(J)OR^{10}$, $-N(R^{10})C(J)N(R^{11})(R^{12})$, $-OC(J)R^{13}$, $-OC(J)OR^{10}$, $-OC(J)N(R^{11})(R^{12})$, $-Si(R^{14})_3$, $-N(R^{10})S(O)_tR^{15}$ and $-S(O)_tR^{15}$;

(b) $R^3$, $R^4$ and $R^5$ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-SR^{16}$, $-R^9-N(R^{11})(R^{12})$ $-R^9-C(J)R^{13}$, $R^9-C(J)OR^{10}$, $-R^9-C(J)N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-R^9-S(O)_tR^{15}$;

or (c) $R^3$, $R^4$ and $R^5$ are each independently hydrogen or $-R^9-C(J)R^{13}$.

In another preferred embodiment, the compound is represented by formula (II) described previously above, wherein:

$R^1$ is optionally substituted cycloalkyl, optionally substituted heterocyclyl, optionally substituted aryl or optionally substituted heteroaryl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})$, $-R^9-C(J)N(R^{10})N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-R^9-S(O)_tR^{15}$;

$R^2$ is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-SR^{16}$ and $-R^9-N(R^{11})(R^{12})$; and $R^3$, $R^4$ and $R^5$ are each independently selected as in (a) or (c) as follows:

(a) $R^3$, $R^4$ and $R^5$ are each independently optionally substituted alkyl, optionally substituted alkenyl or optionally substituted alkynyl, all of which, when substituted are substituted with cyano, nitro, halo, pseudohalo, $-OR^{10}$, $-SR^{16}$, $-N(R^{11})(R^{12})$, $-C(J)R^{13}$, $-C(J)OR^{10}$, $-C(J)N(R^{11})(R^{12})$, $-C(J)N(R^{10})N(R^{11})(R^{12})$, $-N(R^{10})C(J)R^{13}$, $-N(R^{10})C(J)OR^{10}$, $-N(R^{10})C(J)N(R^{11})(R^{12})$, $-OC(J)R^{13}$, $-OC(J)OR^{10}$, $-OC(J)N(R^{11})(R^{12})$, $-Si(R^{14})_3$, $-N(R^{10})S(O)_tR^{15}$ and $-S(O)_tR^{15}$;

or (c) $R^3$, $R^4$ and $R^5$ are each independently selected from a group consisting of hydrogen, halo, $-N(R^7)(R^8)$, $-N(R^{10})C(J)R^{13}$, $-N(R^{10})C(J)OR^{10}$, $-R^9-C(J)R^{13}$, $-N(R^{10})C(J)N(R^{11})(R^{12})$ and $-N(R^{10})S(O)_tR^{15}$.

In another embodiment, $R^3$, $R^4$ and $R^5$ are each independently selected from a group consisting of hydrogen, alkyl, haloalkyl, halo, $-N(R^7)(R^8)$, $-N(R^{10})C(J)R^{13}$, $-N(R^{10})C(J)OR^{10}$, $-R^9-C(J)R^{13}$, $-N(R^{10})C(J)N(R^{11})(R^{12})$ and $-N(R^{10})S(O)_tR^{15}$.

In a further preferred embodiment of the invention, the compounds are:
2-(5-acetyl-2-ethylamino-phenylimino)-3-benzyl-5-(2-oxo-2-phenylethyl)-thiazolidin-4-one;
2-(5-acetyl-2-ethylamino-phenylimino)-3,5-dibenzyl-thiazolidin-4-one; and
2-(5-acetyl-2-ethylamino-phenylimino)-3-benzyl-5-phenethyl-thiazolidin-4-one.

In another preferred embodiment, the compound is represented by the formula (III):

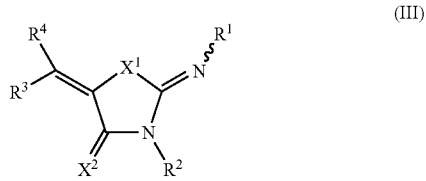

(III)

wherein $X^1$, $X^2$ and $R^1$-$R^4$ are as described in the Summary of the Invention.

In a further preferred embodiment, the compound is represented by the formula (III) described above, wherein:
$X^1$ is S;
$X^2$ is O;
$R^1$ is optionally substituted alkyl, optionally substituted with one to five substituents from the group consisting of cyano, nitro, halo, pseudohalo, —$OR^{10}$, —$SR^{16}$, and —$N(R^{11})(R^{12})$;
or $R^1$ is optionally substituted cycloalkyl, optionally substituted heterocyclyl, optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$;

$R^2$ is optionally substituted alkyl or optionally substituted alkenyl, optionally substituted with one to five substituents from the group consisting of cyano, nitro, halo, pseudohalo, —$OR^{10}$, —$SR^{16}$ and —$N(R^{11})(R^{12})$,
or $R^2$ is optionally substituted cycloalkyl, optionally substituted cycloalkylalkyl, optionally substituted heterocyclyl, optionally substituted heterocyclylalkyl, optionally substituted aryl, optionally substituted aralkyl or optionally substituted heteroaryl, optionally substituted heteroaralkyl, optionally substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$ and —$R^9$—$N(R^{11})(R^{12})$;

$R^3$ and $R^4$ are each independently selected as in (a), (b) or (c) as follows:
(a) $R^3$ and $R^4$ are each independently optionally substituted alkyl, optionally substituted alkenyl or optionally substituted alkynyl, all of which, when substituted are substituted with cyano, nitro, halo, pseudohalo, —$OR^{10}$, —$SR^{16}$, —$N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$, —$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, —$Si(R^{14})_3$, —$N(R^{10})S(O)_tR^{15}$ and —$S(O)_tR^{15}$;

(b) $R^3$ and $R^4$ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$;

or (c) $R^3$ and $R^4$ are each independently hydrogen or —$R^9$—$C(J)R^{13}$;

provided that when $R^3$ or $R^4$ is alkyl, alkenyl, alkynyl, halo, haloalkyl, cycloalkyl, —$R^9$—$C(J)R^{13}$, aryl or heteroaryl, then $R^1$ is phenyl and $R^1$ is substituted with at least two different substituents selected from the following: cyano, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{12})R^{13}$, $R^9$—$N(R^{10})C(J)OR^{10}$, —$R^9$—$N(R^{10})C(J)N(R^{11})(R^{12})$, —$N(R^{10})S(O)_tR^{13}$, —$R^9$—$N(R^{10})C(J)R^{13}$, and —$R^9$—$N(R^{11})(R^{12})$;

and further provided that $R^3$ and $R^4$ are not both hydrogen.

In a still further preferred embodiment of the invention, the compounds are:
2-(5-acetyl-2-ethylamino-phenylimino)-3-benzyl-5-benzylidene-thiazolidin-4-one; and
2-(5-acetyl-2-ethylamino-phenylimino)-3-benzyl-5-furan-2-ylmethylene-thiazolidin-4-one.

In a particularly preferred embodiment of the invention, the compounds are represented by the formulae (IVa or IVb):

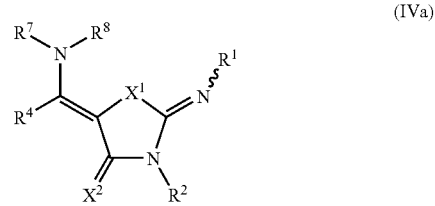

(IVa)

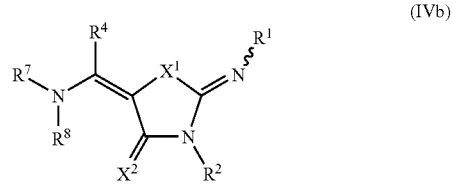

(IVb)

wherein $X^1$, $X^2$, $R^1$, $R^2$, $R^4$, $R^7$ and $R^8$ are as described in the Summary of the Invention.

A further preferred embodiment of the invention, the compounds are represented by the formulae (IVa or IVb) described above, wherein:
$X^1$ is S;
$X^2$ is O;
$R^1$ is optionally substituted alkyl, optionally substituted alkenyl or optionally substituted alkynyl, all or which, when substituted, are substituted with one to five substituents from the group consisting of cyano, nitro, halo, pseudohalo, —OR$^{10}$, —SR$^{16}$, —N(R$^{11}$)(R$^{12}$), —C(J)R$^{13}$, —C(J)OR$^{10}$, C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_r$R$^{15}$ and —R$^9$—S(O)$_r$R$^{15}$;

or R$^1$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_r$R$^{15}$ and —R$^9$—S(O)$_r$R$^{15}$;

or R$^1$ is —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—N(R$^{10}$)C(J)R$^{13}$, R$^9$—N(R$^{10}$)C(J)OR$^{10}$, —R$^9$—S(O)$_r$R$^{15}$ or —R$^9$—N(R$^{10}$)C(J)N(R$^{11}$)(R$^{12}$);

R$^2$ is optionally substituted alkyl, optionally substituted alkenyl, optionally substituted alkynyl, all or which, when substituted, are substituted with one to five substituents from the group consisting of cyano, nitro, halo, pseudohalo, —OR$^{10}$, —SR$^{16}$, —N(R$^{11}$)(R$^{12}$), —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_r$R$^{15}$ and —S(O)$_r$R$^{15}$;

or R$^2$ is optionally substituted cycloalkyl, optionally substituted cycloalkylalkyl, optionally substituted heterocyclyl, optionally substituted heterocyclylalkyl, optionally substituted aryl, optionally substituted heteroaryl, optionally substituted aralkyl, optionally substituted heteroaralkyl or optionally substituted aryl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_r$R$^{15}$ and —R$^9$—S(O)$_r$R$^{15}$;

or R$^2$ is —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), R$^9$—N(R$^{11}$)(R$^{12}$) or —R$^9$—S(O)$_r$R$^{15}$;

R$^4$ is hydrogen, halo or alkyl;

R$^7$ is hydrogen or optionally substituted alkyl, optionally substituted with cyano, nitro, halo, pseudohalo, —OR$^{10}$, —SR$^{16}$, —N(R$^{11}$)(R$^{12}$), —OR$^{16}$OR$^{10}$, —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_r$R$^{15}$ and —S(O)$_r$R$^{15}$;

or R$^7$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—OR$^{16}$OR$^{10}$, —R$^9$—SR$^{16}$, R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—C(J)N(R$^{10}$)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_r$R$^{15}$ and —R$^9$—S(O)$_r$R$^{15}$; and R$^8$ is optionally substituted alkyl, optionally substituted alkenyl or optionally, substituted alkynyl, all of which, when substituted, are substituted with one to three substituents from the group consisting of cyano, nitro, halo, pseudohalo, —OR$^{10}$, —SR$^{16}$, —N(R$^{11}$)(R$^{12}$), —OR$^{16}$OR$^{10}$, —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_r$R$^{15}$ and —S(O)$_r$R$^{15}$;

or R$^8$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—OR$^{16}$OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_r$R$^{15}$ and —S(O)$_r$R$^{15}$;

or R$^7$ and R$^8$ together with the nitrogen atom to which they are attached, form an optionally substituted heterocyclyl, optionally substituted heterocyclylalkyl or an optionally substituted heteroaryl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—OR$^{16}$OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_r$R$^{15}$ and —S(O)$_r$R$^{15}$.

In yet another particularly preferred embodiment of the invention, the compounds are represented by the formulae (IVa or IVb) described previously above, wherein:

X$^1$ is S;

X$^2$ is O;

R$^1$ is optionally substituted cycloalkyl, optionally substituted heterocyclyl, optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_r$R$^{15}$ and —R$^9$—S(O)$_r$R$^{15}$;

R$^2$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, optionally substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$ and —R$^9$—N(R$^{11}$)(R$^{12}$);

R$^4$ is hydrogen, halo or alkyl;

R$^7$ and R$^8$ together with the nitrogen atom to which they are attached, form an optionally substituted heterocyclyl or an optionally substituted heteroaryl optionally substituted with cyano, nitro, halo, pseudohalo, —OR$^{10}$, —SR$^{16}$ or —N(R$^{11}$)(R$^{12}$).

In another particularly preferred embodiment of the invention, the compounds are:

3-[3-benzyl-5-(2,3-dihydroindol-1-ylmethylene)-4-oxothiazolidin-2-ylideneamino]-4-ethylamino-benzonitrile;

2-(5-acetyl-2-ethylamino-phenylimino)-3-benzyl-5-(2,3-dihydroindol-1-ylmethylene)-thiazolidin-4-one;

2-(3-acetylphenylimino)-5-(2,3-dihydroindol-1-ylmethylene)-3-furan-2-ylmethyl-thiazolidin-4-one;

N-{4-[5-(2,3-dihydroindol-1-ylmethylene)-3-furan-2-ylmethyl-4-oxothiazolidin-2-ylideneamino]-phenyl}-acetamide; and 2-(5-acetyl-2-ethylamino-phenylimino)-3-benzyl-5-(4-methylpiperazin-1-ylmethylene)-thiazolidin-4-one.

In yet another particularly preferred embodiment of the invention, the compound is represented by the formulae (IVa) and (IVb) described previously above, wherein:

X$^1$ is S;

X$^2$ is O;

R$^1$ is optionally substituted cycloalkyl, optionally substituted heterocyclyl, optionally substituted aryl, optionally substituted aralkyl,—optionally substituted heteroaryl- or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_r$R$^{15}$ and —R$^9$, —S(O)$_r$R$^{15}$;

R$^2$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, optionally substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$ and —R$^9$—N(R$^{11}$)(R$^{12}$);

R$^4$ is hydrogen, halo or alkyl;

R$^7$ is hydrogen or optionally substituted alkyl, optionally substituted with cyano, nitro, halo, pseudohalo, —OR$^{10}$, —SR$^6$ or —N(R$^{11}$)(R$^{12}$);

or R$^7$ is optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—OR$^{16}$OR$^{10}$, —R$^9$—SR$^{16}$ and —R$^9$—N(R$^{11}$)(R$^{12}$); and R$^8$ is optionally substituted alkyl, optionally substituted with cyano, nitro, halo, pseudohalo, —OR$^{10}$, —SR$^{16}$ and —N(R$^{11}$)(R$^{12}$);

or R$^8$ is optionally substituted aryl, optionally substituted aralkyl, optionally substituted heteroaryl or optionally substituted heteroaralkyl, all of which, when substituted, are substituted with one to five substituents from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—OR$^{16}$OR$^{10}$, —R$^9$—SR$^{11}$ and —R$^9$—N(R$^{11}$)(R$^{12}$).

In another particularly preferred embodiment of the invention, the compounds are:

3-{3-Benzyl-5-[(N-methyl-phenylamino)-methylene]-4-oxothiazolidin-2-ylideneamino}-4-ethylamino-benzonitrile;

2-(5-acetyl-2-ethylamino-phenylimino)-3-benzyl-5-[(N-methyl-phenylamino)-methylene]-thiazolidin-4-one;

3-{3-benzyl-5-[(N-benzyl-methylamino)-methylene]-4-oxothiazolidin-2-ylideneamino}-4-ethylamino-benzonitrile;

2-(5-acetyl-2-ethylamino-phenylimino)-3-benzyl-5-[(N-benzyl-methylamino)-methylene]-thiazolidin-4-one;

3-(3-benzyl-5-{[N-(4-methoxyphenyl)-methylamino]-methylene}-4-oxothiazolidin-2-ylideneamino)-4-ethylamino-benzonitrile;

2-(5-acetyl-2-ethylamino-phenylimino)-3-benzyl-5-{[N-(4-methoxyphenyl)-methylamino]-methylene}-thiazolidin-4-one;

3-(3-benzyl-5-{[N-(2-methoxyphenyl)-methylamino]-methylene}-4-oxothiazolidin-2-ylideneamino)-4-ethylamino-benzonitrile;

2-(5-acetyl-2-ethylamino-phenylimino)-3-benzyl-5-{[N-(3-methoxyphenyl)-methylamino]-methylene}-thiazolidin-4-one;

2-(5-acetyl-2-ethylamino-phenylimino)-3-benzyl-5-[(N-methyl-phenethylamino)-methylene]-thiazolidin-4-one;

2-(5-acetyl-2-ethylamino-phenylimino)-3-benzyl-5-({N-[4-(2-methoxy-ethoxy)-phenyl]-methylamino}-methylene)-thiazolidin-4-one;

3-{3-benzyl-5-[(4-methoxyphenylamino)-methylene]-4-oxothiazolidin-2-ylideneamino}-4-ethylamino-benzonitrile;

3-(3-benzyl-5-dimethylaminomethylene-4-oxothiazolidin-2-ylideneamino)-4-ethylamino-benzonitrile;

2-(5-acetyl-2-ethylamino-phenylimino)-3-benzyl-5-dimethylaminomethylene-thiazolidin-4-one; and 2-(5-acetyl-2-ethylamino-phenylimino)-3-benzyl-5-{[(3-dimethylaminopropyl)-methylamino]-methylene}-thiazolidin-4-one.

In one embodiment, the compounds for use in the composition and methods provided are set forth in Table I.

C. Preparation of the Compounds of the Invention

Starting materials in the synthesis examples provided herein are either available from commercial sources or via literature procedures. All commercially available compounds were used without further purification unless otherwise indicated. CDCl$_3$ (99.8% D, Cambridge Isotope Laboratories) was used in all experiments as indicated. Proton ($^1$H) nuclear magnetic resonance (NMR) spectra were recorded on a Bruker Avance 400 MHz NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low-resolution mass spectra (MS) were obtained as electrospray ionization (ESI) mass spectra, which were recorded on a Perkin-Elmer SCIEX HPLC/MS instrument using reverse-phase conditions (acetonitrile/water, 0.05% trifluoroacetic acid). Flash chromatography was performed using Merck Silica Gel 60 (230-400 mesh) following standard protocol (Still et al. (1978) *J. Org. Chem.* 43, 2923).

The following illustrations depict general preparations of compounds claimed herein and consist of reactions typically known to one skilled in the art of chemical synthesis. The substituents $X^1$, $X^2$ and $R^1$-$R^8$ have been previously described. Also it will be apparent to one skilled in the art that many of the products could exist as one or more isomers, that is E/Z isomers, enantiomers and/or diastereomers.

Provisional application No. 60/342,720, filed on Dec. 21, 2001, and its corresponding non-provisional application Ser. No. 10/329,668, filed Dec. 20, 2002, which describe in additional detail certain background information, procedures, compounds and/or compositions, are hereby incorporated by reference in their entirety. In general, compounds of Formula (I), such as alkylidene-5-yl-2-iminoazolidines (2a-b), can be prepared via condensation reactions with 2-iminoazolines (1) as depicted in Scheme 1. Thus, for example, when 1 is 2-imino-4-thiazolidinone ($X^1$=S; $X^2$=O), it can be condensed with aldehydes (e.g. $R^3$CHO) or ketones to yield alkylidene-5-yl-2-imino-4-thiazolidinones, 2a-b ($R^4$=H; $X^1$=S; $X^2$=O). Other azolines 1 (e.g. $X^1$=O or $NR^6$) also can undergo similar condensation reactions.

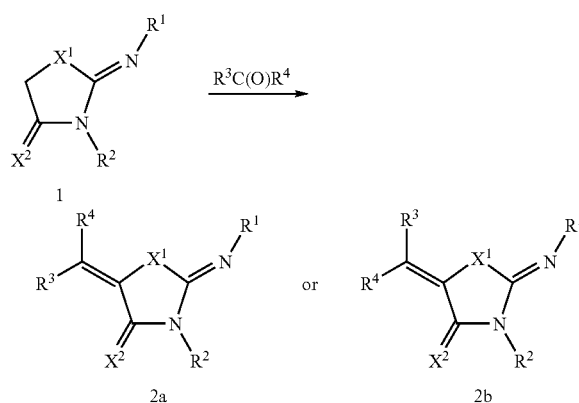

In addition, 5-aminomethylene-2-iminoazolidines (3) can be prepared via condensation reactions with 2-iminoazolines 1 as depicted in Scheme 2. Thus, for example, when 1 is 2-imino-4-thiazolidinone ($X^1$=S; $X^2$=O), it can be condensed with formamide acetals to yield 5-aminomethylene-2-imino-4-thiazolidinones, 3 ($X^1$=S; $X^2$=O). Formamide acetals can be prepared or generated in situ from a mixture of an amine, $HN(R^6)R^7$, and an orthoformate (e.g. trimethylorthoformate) or a lower amide acetal (e.g. dimethylformamide dimethyl acetal) at elevated temperature (Abdulla et al., (1979) *Tetrahedron* 35:1675-1735; and U.S. Pat. No. 4,431,653). Alternatively, 1 can react with a mixture of an amine and an orthoformate in a one-pot synthesis to yield a 5-aminomethylene-2-iminoazolidine 3. Moreover, 1 can react with higher amide acetals (e.g. dimethylacetamide dimethyl acetal) to afford the corresponding 5-(1-amino)alkylene-2-iminoazolidines (e.g. 5-(1-amino)ethylene-2-iminoazolidines).

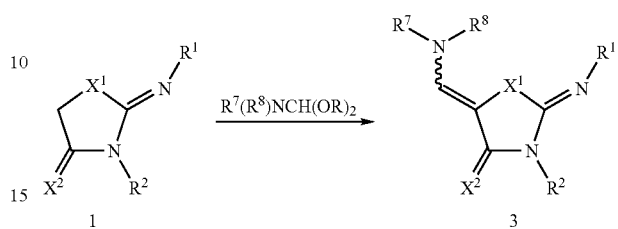

Also, 2-iminoazolines 1 can react with other electrophiles. Thus, for example, when 1 is 2-imino-4-thiazolidinone ($X^1$=S; $X^2$=O), it can be alkylated with alkyl halides to yield 5-alkyl-2-imino-4-thiazolidinones (4, $X^1$=S; $X^2$=O) as depicted in Scheme 3.

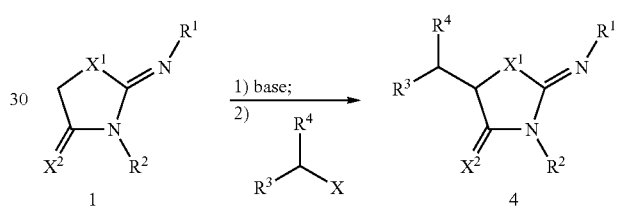

In general, 2-iminoazolidines 1 can be synthesized as depicted in Scheme 4. Thus, for example, when 1 is an 2-imino-4-thiazolidinone ($X^1$=S; $X^2$=O), it can be prepared by condensing a thiourea 5 ($X^1$=S) with a 2-haloester ($X^2$=O) in the presence of base, in which $R^1$ is typically aryl or heteroaryl (International Patent Application Pub. No. WO 00/42031; and Seada et al. (1993) *Indian J. Heterocycl. Chem.* 3:81).

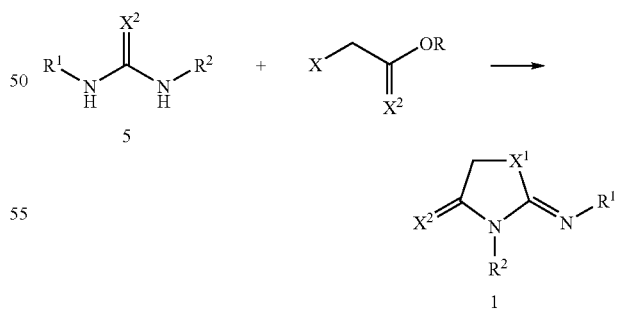

In addition, 2-iminoazolidines 1 can be synthesized from a carbodiimide (6) as depicted in Scheme 5. For example, when 1 is a 2-imino-4-imidazolidinone ($X^1$=$NR^6$; $X^2$=O), it can be prepared by reacting carbodiimide 6 with an 2-aminoester ($X^1$=$NR^6$; $X^2$=O). Likewise, an 2-imino-4-oxazolidinones ($X^1$-$X^2$=O) can be prepared from carbodiimide 6 and a 2-hydroxyester.

SCHEME 5

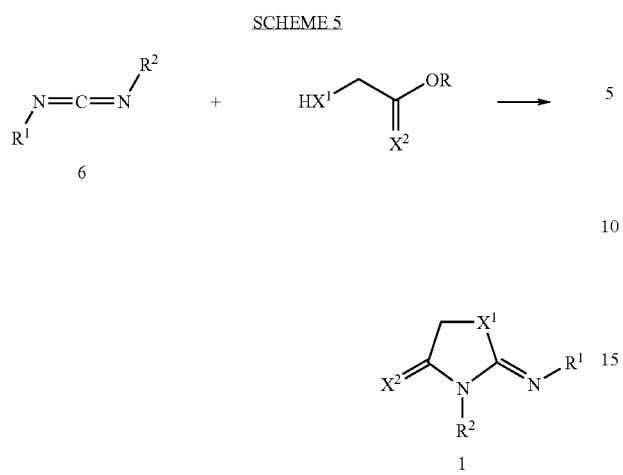

As depicted in Scheme 6, 2-thioxoazolines (7) can undergo similar condensation reactions as described earlier. Thus, for example, when 7 is 2-thioxo-4-thiazolidinone ($X^1$=S; $X^2$=O), it can be condensed with an aldehyde (e.g. $R^3$CHO) to yield an alkyliden-5-yl-2-thioxo-4-thiazolidinone (8a-b, $X^1$=S; $X^2$=O) or with a formamide acetal to yield a 5-aminomethylene-2-thioxo-4-thiazolidinone (9, $X^1$=S; $X^2$=O).

SCHEME 6

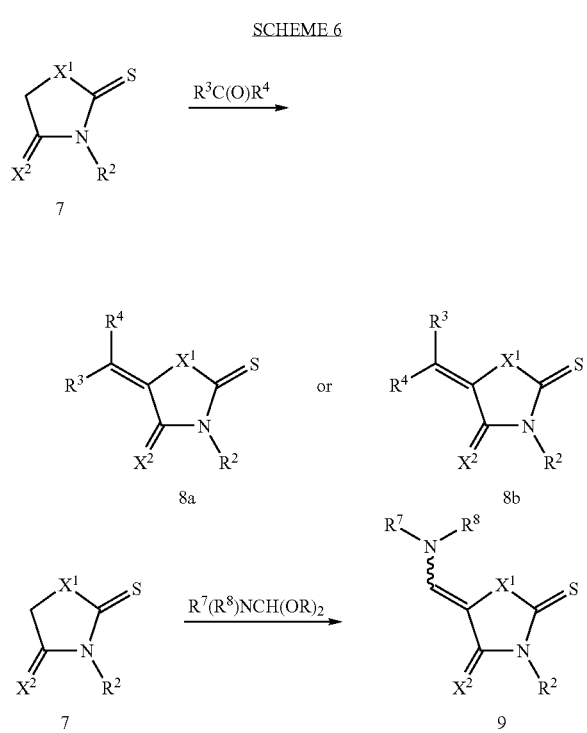

Intermediates 8a-b then can be converted to their respective imine products 2a-b as depicted in Scheme 7. Thus, for example, when 2a-b is alkyliden-5-yl-2-imino-4-thiazolidinone ($X^1$=S; $X^2$=O), it can be prepared stepwise by alkylation of alkyliden-5-yl-2-thioxo-4-thiazolidinone 8a-b ($X^1$=S; $X^2$=O) to afford an intermediate alkyliden-5-yl-2-alkylthio-4-thiazolidinon-3-ium complex, which can be reacted subsequently with an amine ($R^1NH_2$) to yield imine 2a-b.

SCHEME 7

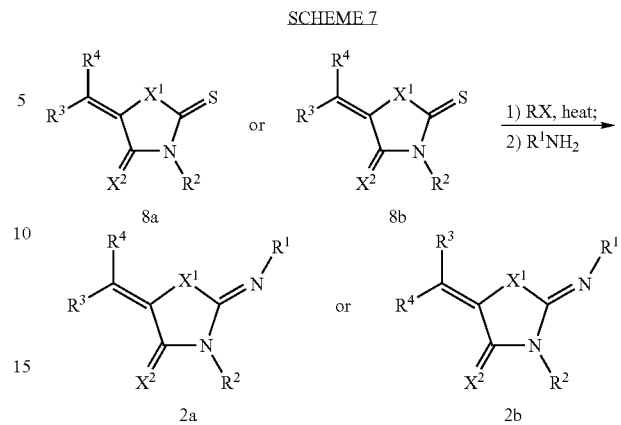

Likewise, 9 can be converted to its respective imine 3 as depicted in Scheme 8. For example, when 3 is 5-aminomethylene-2-imino-4-thiazolidinones ($X^1$=S; $X^2$=O), it can be prepared stepwise by alkylation of 5-aminomethylene-2-thioxo-4-thiazolidinone, 9 ($X^1$=S; $X^2$=O) to afford an intermediate 5-aminomethylene-2-alkylthio-4-thiazolidinon-3-ium complex, that can be subsequently reacted with an amine to yield imine 3.

SCHEME 8

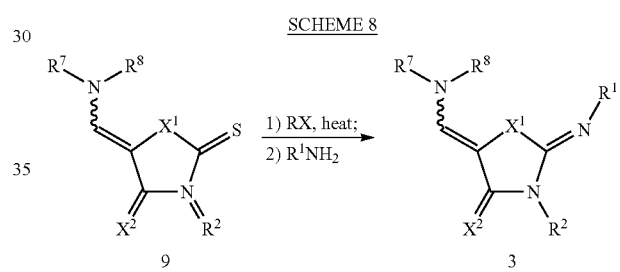

Isothiocyanates, aryl amines, heteroaryl amines, unsymmetrical thioureas 5, carbodiimides 6 and 2-thioxoazolines 7 can be synthesized utilizing known methodology (see, e.g., Katritzky et al. (1984) *Comprehensive Heterocyclic Chemistry*; Pergamon Press: Oxford, UK; Katritzky et al. (2000) *Handbook of Heterocyclic Chemistry*, 2$^{nd}$ Ed.; Pergamon Press: Oxford, UK; March Advanced Organic Chemistry, 4$^{th}$ Ed.; John Wiley: New York (1992); and International Patent Application Publication No. WO 00/42031). For example, isothiocyanates are readily prepared from reaction of an amine with thiophosgene or a thiophosgene equivalent, e.g. thiocarbonyl diimidazole. Many isothiocyanates also are commercially available. Unsymmetrical thioureas 5 can be prepared from reaction of an isothiocyanate with a primary amine. Also, for example, when 7 is 2-thioxo-4-thiazolidinones ($X^1$=S; $X^2$=O), it can be prepared by reaction (addition-condensation) of isothiocyanates with 2-mercaptoacids or 2-mercaptoesters (see, e.g., Dogan et al. (1992) *Tetrahedron* 48:7157; and Drobnica et al. (1972) *Chem. Zvesti* 26:538). Furthermore, some 2-thioxo-4-thiazolidinones (also referred to as rhodanines) are commercially available.

D. Formulation of Pharmaceutical Compositions

The pharmaceutical compositions provided herein contain therapeutically effective amounts of one or more of the nuclear receptor activity modulators provided herein that are useful in the prevention, treatment, or amelioration of one or more of the symptoms of diseases or disorders associated with nuclear receptor activity, including FXR, LXR and/or orphan nuclear receptor activity. Such diseases or disorders include, but are not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, and cardiovascular disorders.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with nuclear receptor activity or in which nuclear receptor activity is implicated. Such diseases or disorders include, but are not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, and cardiovascular disorders.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in International Patent Application Publication Nos. 99/27365 and 00/25134 (see, e.g., EXAMPLES 53 and 54) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with nuclear receptor activity or in which nuclear receptor activity is implicated, as described herein.

Typically, a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with nuclear receptor activity or in which nuclear receptor activity is implicated, as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings. The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with nuclear receptor activity or in which nuclear receptor activity is implicated. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically, a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

Pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for modulating the activity of nuclear receptors, including the farnesoid X receptor and/or orphan nuclear receptors, or for treatment, prevention or amelioration of one or more symptoms of nuclear receptor, including the farnesoid X receptor and/or orphan nuclear receptor, mediated diseases or disorders, or diseases or disorders in which nuclear receptor activity, including the farnesoid X receptor and/or orphan nuclear receptor activity, is implicated, within the packaging material, and a label that indicates that the compound or composition, or pharmaceutically acceptable derivative thereof, is used for modulating the activity of nuclear receptors, including the farnesoid X receptor and/or orphan nuclear receptors, or for treatment, prevention or amelioration of one or more symptoms of nuclear receptor, including the farnesoid X receptor and/or orphan nuclear receptor, mediated diseases or disorders, or diseases or disorders in which nuclear receptor activity, including the farnesoid X receptor and/or orphan nuclear receptor activity, is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which nuclear receptor activity, including the farnesoid X receptor and/or orphan nuclear receptor activity, is implicated as a mediator or contributor to the symptoms or cause.

E. Evaluation of the Activity of the Compounds

Standard physiological, pharmacological and biochemical procedures are available for testing the compounds to identify those that possess biological activities that modulate the activity or nuclear receptors, including the farnesoid X receptor and/or orphan nuclear receptors. Such assays include, for example, biochemical assays such as binding assays, fluorescence polarization assays, FRET based coactivator recruitment assays (see generally Glickman et al., *J. Biomolecular Screening*, 7 No. 1 3-10 (2002)), as well as cell based assays including the co-transfection assay, the use of LBD-Gal 4 chimeras and protein-protein interaction assays (see, Lehmann. et al, *J. Biol. Chem.*, 272(6) 3137-3140 (1997).

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see for example, Owicki, J., Biomol Screen 2000 October; 5(5):297) scintillation proximity assays (SPA) (see for example, Carpenter et al., Methods Mol Biol 2002; 190:31-49) and fluorescence resonance energy transfer energy transfer (FRET) or time resolved FRET based coactivator recruitment assays (Mukherjee et al., *J Steroid Biochem Mol Biol* 2002 July; 81(3):217-25; (Zhou et al., *Mol. Endocrinol.* 1998 October; 12(10):1594-604). Generally such assays can be preformed using either the full length receptor, or isolated ligand binding domain (LBD). In the case of the farnesoid X receptor, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound generates an optical signal when it is brought into close proximity to a scintillant such as a Ysi-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of the farnesoid X receptor with RXRα can also be measured by fluorescence resonance energy transfer (FRET), or time resolved FRET, to monitor the ability of the compounds provided herein to bind to the farnesoid X receptor or other nuclear receptors. Both approaches rely upon the fact that energy transfer from a donor molecule to an acceptor molecule only occurs when donor and acceptor are in close proximity. Typically, the purified LBD of the nuclear receptor of interest is labeled with biotin then mixed with stoichiometric amounts of europium labeled streptavidin (Wallac Inc.), and the purified LBD of RXRα is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically, the assay in this case involves the use a recombinant Glutathione-S-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor.

In addition, a variety of cell based assay methodologies may be successfully used in screening assays to identify and profile the specificity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor. (See for example U.S. Pat. Nos. 5,071,773; 5,298,429, 6,416,957, WO 00/76523). Treatment of the transfected cells with an agonist for the nuclear receptor increases the transcriptional activity of that receptor which is reflected by an increase in expression of the reporter gene, which may be measured by a variety of standard procedures.

For those receptors that function as heterodimers with RXR, such as the farnesoid X receptor, the co-transfection assay typically includes the use of expression plasmids for both the nuclear receptor of interest and RXR. Typical co-transfection assays require access to the full-length nuclear receptor and suitable response elements that provide sufficient screening sensitivity and specificity to the nuclear receptor of interest.

Genes encoding the following full-length previously described proteins, which are suitable for use in the co-transfection studies and profiling the compounds described herein, include rat farnesoid X receptor (GenBank Accession No. NM_021745), human farnesoid X receptor (GenBank Accession No. NM_005123), human RXR α (GenBank Accession No. NM_002957), human RXR β (GenBank Accession No. XM_042579), human RXR γ (GenBank Accession No. XM_053680), human LXR α (GenBank Accession No. NM_005693), human LXR β (GenBank Accession No. NM_007121), human PPARα (GenBank Accession No. NM_005036) and human PPAR δ (GenBank Accession No. NM_006238).

Reporter plasmids may be constructed using standard molecular biological techniques by placing cDNA encoding for the reporter gene downstream from a suitable minimal promoter. For example, luciferase reporter plasmids may be constructed by placing cDNA encoding firefly luciferase immediately down stream from the herpes virus thymidine kinase promoter (located at nucleotides residues-105 to +51 of the thymidine kinase nucleotide sequence) which is linked in turn to the various response elements.

Numerous methods of co-transfecting the expression and reporter plasmids are known to those of skill in the art and may be used for the co-transfection assay to introduce the plasmids into a suitable cell type. Typically, such a cell will not endogenously express nuclear receptors that interact with the response elements used in the reporter plasmid.

Numerous reporter gene systems are known in the art and include, for example, alkaline phosphatase Berger, J., et al. (1988) Gene 66 1-10; Kain, S. R. (1997) Methods. Mol. Biol. 63 49-60), β-galactosidase (See, U.S. Pat. No. 5,070,012, issued Dec., 3, 1991 to Nolan et al., and Bronstein, I., et al., (1989) J. Chemilum. Biolum. 4 99-111), chloramphenicol acetyltransferase (See Gorman et al., Mol Cell Biol. (1982) 2 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; 5,843,746) and naturally fluorescent proteins (Tsien, R. Y. (1998) Annu. Rev. Biochem. 67 509-44).

The use of chimeras comprising the ligand binding domain (LBD) of the nuclear receptor of interest to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general, the methodology is similar to that used with the basic co-transfection assay, except that a chimeric construct is used in place of the full-length nuclear receptor. As with the full-length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional regulators such as members of the GAL 4 and Lex A/Umud super families are used.

A third cell based assay of utility for screening compounds of the present invention is a mammalian two-hybrid assay that measures the ability of the nuclear hormone receptor to interact with a cofactor in the presence of a ligand. (See for example, U.S. Pat. Nos. 5,667,973, 5,283,173 and 5,468,614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene, which can be measured for various reporter genes as described above. Transcription of the reporter gene is thus driven by the interaction of the interacting protein and nuclear receptor of interest in a ligand dependent fashion.

Any compound which is a candidate for activation of the farnesoid X receptor may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally, the compounds and compositions can be evaluated for their ability to increase or decrease the expression of genes known to be modulated by the farnesoid X receptor and other nuclear receptors in vivo, using Northern-blot, RT PCR or oligonucleotide microarray analysis to analyze RNA levels. Western-blot analysis can be used to measure expression of proteins encoded by farnesoid X receptor target genes. Genes that are known to be regulated by the farnesoid X receptor include cholesterol 7 α-hydroxylase (CYP7A1), the rate limiting enzyme in the conversion of cholesterol to bile acids, the small heterodimer partner-1 (SHP-1), the bile salt export pump (BSEP, ABCB11), canalicular bile acid export protein, sodium taurocholate cotransporting polypeptide (NTCP, SLC10A1) and intestinal bile acid binding protein (1-BABP).

Established animal models exist for a number of diseases of direct relevance to the claimed compounds and these can be used to further profile and characterize the claimed compounds. These model systems include diabetic dislipidemia using Zucker (fa/fa) rats or (db/db) mice, spontaneous hyperlipidemia using apolipoprotein E deficient mice (ApoE$^{-/-}$), diet-induced hyperlipidemia, using low density lipoprotein receptor deficient mice (LDR$^{-/-}$) and atherosclerosis using both the Apo E($^{-/-}$) and LDL($^{-/-}$) mice fed a western diet, (21% fat, 0.05% cholesterol). Additionally farnesoid X receptor or LXR animal models (e.g., knockout mice) can be used to further evaluate the present compounds and compositions in vivo (see, for example, Sinal, et al., *Cell*, 102: 731-744 (2000), Peet, et al., *Cell*, 93:693-704 (1998)).

F. Methods of Use of the Compounds and Compositions

Methods of use of the compounds and compositions provided herein are also provided. The methods involve both in vitro and in vivo uses of the compounds and compositions for altering nuclear receptor activity, including the farnesoid X receptor and/or orphan nuclear receptor activity, and for treatment, prevention, or amelioration of one or more symptoms of diseases or disorder that are modulated by nuclear receptor activity, including the farnesoid X receptor and/or orphan nuclear receptor activity, or in which nuclear receptor activity, including the farnesoid X receptor and/or orphan nuclear receptor activity, is implicated. Such compounds or compositions will typically exhibit farnesoid X receptor agonist, partial agonist, partial antagonist or antagonist activity in one of the in vitro assays described herein.

Methods of altering nuclear receptor activity, including the farnesoid X receptor, and/or orphan nuclear receptor activity, by contacting the receptor with one or more compounds or compositions provided herein, are provided.

Methods of reducing plasma cholesterol levels and of directly or indirectly modulating cholesterol metabolism, catabolism, synthesis, absorption, re-absorption, secretion or excretion are provided through administering the claimed compounds and compositions provided herein. Methods of reducing dietary cholesterol absorption (see, e.g., International Patent Application Publication No. 00/40965) using the compounds and compositions are provided herein. Also provided, are methods of increasing the expression of ATP-Binding Cassette (ABCA1), thereby increasing reverse cholesterol transport in mammalian cells using the claimed compounds and compositions (see, e.g., International Patent Application Publication No. WO 00/78972).

Methods of reducing plasma triglyceride levels and of directly or indirectly modulating triglyceride metabolism, catabolism, synthesis, absorption, re-absorption, secretion or excretion are provided through administering the claimed compounds and compositions provided herein.

Methods of reducing bile acid levels and of directly or indirectly modulating bile acid metabolism, catabolism, synthesis, absorption, re-absorption, secretion, excretion, or bile acid pool size or composition are provided through administering the claimed compounds and compositions provided herein.

Methods of treatment, prevention, or amelioration of one or more symptoms of a disease or disorder affecting cholesterol, triglyceride, or bile acid levels, or any combination thereof, are provided using the compounds and compositions provided herein.

Methods are provided for the treatment, prevention, or amelioration of one or more symptoms of, as well as treating the complications of, hyperlipidemia, hypercholesterolemia, dyslipidemia and lipodystrophy.

The term "hyperlipidemia" refers to the presence of an abnormally elevated level of lipids in the blood. Hyperlipidemia can appear in at least three forms: (1) hypercholesterolemia, i.e., an elevated LDL cholesterol level (120 mg/dL and above); (2) hypertriglyceridemia, i.e., an elevated triglyceride level; (150 mg/dL and above) and (3) combined hyperlipidemia, i.e., a combination of hypercholesterolemia and hypertriglyceridemia.

The term "dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL) (less than 40 mg/dL)).

Methods are also provided for the treatment, prevention, or amelioration of one or more symptoms of atherosclerosis, atherosclerotic disease, atherosclerotic disease events and atherosclerotic cardiovascular diseases.

Atherosclerosis is the process in which deposits of fatty substances, cholesterol, cellular waste products, calcium and other substances build up in the inner lining of an artery. This buildup is called plaque. It initially affects large and medium-sized arteries. Some hardening of arteries often occurs when people grow older.

Plaques can grow large enough to significantly reduce the blood's flow through an artery. However significant damage to the body can also occur when the artery walls become fragile and rupture. Atherosclerotic plaques that rupture can cause blood clots to form that can block blood flow or break off and travel to another part of the body. If either happens and the blood clot blocks a blood vessel that feeds the heart, it can cause a heart attack. If the blood clot blocks a blood vessel that feeds the brain, it can cause a stroke. And if blood supply to the arms or legs is reduced, it can cause difficulty walking and eventually gangrene.

Accordingly, atherosclerosis encompasses a range of vascular diseases and conditions that arise as a result of the primary disease modality. Atherosclerotic cardiovascular diseases can be recognized and understood by physicians practicing in the relevant fields of medicine and include the following: Restenosis following revascularization procedures, coronary heart disease (also known as coronary artery heart disease or ischemic heart disease), cerebrovascular disease including ischemic stroke, multi-infarct dementia, and peripheral vessel disease, including erectile dysfunction.

A compound or composition of the present invention may be administered to prevent or reduce the risk of occurrence, or recurrence where the potential exists, of coronary heart disease event, a cerebrovascular event, and/or intermittent claudication.

Coronary heart disease events are intended to include coronary heart disease death, myocardial infarction and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease.

The term "atherosclerotic disease event" as used herein is intended to encompass coronary heart disease events, cerebrovascular events, and intermittent claudication. It is intended that person who have previously experienced one or more non-fatal atherosclerotic disease events are those for whom the potential for recurrence of such an event exists.

Additionally, the instant invention also provides a method for preventing or reducing the risk of a first or subsequent occurrence of an atherosclerotic disease event comprising the administration of a prophylactically effective amount of a compound or composition of the present invention to a patient at risk for such an event. The patient may already have atherosclerotic disease at the time of administration, or may be at risk for developing it.

Risk factors for developing atherosclerotic disease events include increasing age (65 and over), male gender, a family history of atherosclerotic disease events, high blood cholesterol (especially LDL or "bad" cholesterol over 100 mg/dL), cigarette smoking and exposure to tobacco smoke, high blood pressure, Diabetes mellitus, obesity and physical inactivity.

In another aspect, the method of this invention also serves to remove cholesterol from tissue deposits such as atherosclerotic plaques or xanthomas in a patient with atherosclerotic disease manifest by clinical signs such as angina, claudication, bruits, one that has suffered a myocardial infarction or transient ischemic attack, or one diagnosed by angiography, sonography or MRI.

Methods of treatment, prevention, or amelioration of one or more of the symptoms of diabetes mellitus, as well as treating the complications of diabetes mellitus, (see, e.g., International Patent Application Publication No. WO 01/82917) are also provided using the compounds and compositions provided herein.

Diabetes mellitus, commonly called diabetes, refers to a disease or condition that is generally characterized by metabolic defects in production and utilization of glucose which result in the failure to maintain appropriate blood sugar levels in the body (see, e.g., LeRoith, D. et al., (eds.), DIABETES MELLITUS (Lippincott-Raven Publishers, Philadelphia, Pa. U.S.A. 1996)).

In the case of diabetes of the type 2 form, the disease is characterized by insulin resistance, in which insulin loses its ability to exert its biological effects across a broad range of concentrations. This resistance to insulin responsiveness results in insufficient insulin activation of glucose uptake, oxidation and storage in muscle and inadequate insulin repression of lipolysis in adipose tissue and of glucose production and secretion in liver (see, e.g., Reaven, G. M., J. Basic & Clin. Phys. & Pharm. (1998) 9: 387-406 and Flier, J. Ann Rev. Med. (1983) 34:145-60). The resulting condition is elevated blood glucose, which is called "hyperglycemia." Uncontrolled hyperglycemia is associated with increased and premature mortality due to an increased risk for microvascular and macrovascular diseases, including retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys), hypertension, cerebrovascular disease and coronary heart disease. Therefore, control of glucose homeostasis is an important approach for the treatment of diabetes.

Methods of treatment, prevention, or amelioration of one or more of the symptoms of insulin insensitivity or resistance as well as treating the complications of insulin insensitivity or resistance (see, e.g., International Patent Application Publication No. WO 01/82917) are also provided using the compounds and compositions provided herein.

Methods of treatment, prevention, or amelioration of one or more of the symptoms of hyperglycemia as well as treating the complications of hyperglycemia (see, e.g., International Patent Application Publication No. WO 01/82917) are also provided using the compounds and compositions provided herein.

Insulin resistance has been hypothesized to unify the clustering of hypertension, glucose intolerance, hyperinsulinemia, increased levels of triglyceride and decreased HDL cholesterol, and central and overall obesity. The association of insulin resistance with glucose intolerance, an increase in plasma triglyceride and a decrease in high-density lipoprotein cholesterol concentrations, hypertension, hyperuricemia, smaller denser low-density lipoprotein particles, and higher circulating levels of plasminogen activator inhibitor-1, has been referred to as "Syndrome X" (see, e.g., Reaven, G. M., Physiol. Rev. (1995) 75: 473-486). Accordingly, methods of treatment, prevention, or amelioration of any disorders related to diabetes, hyperglycemia or insulin resistance including the cluster of disease states, conditions or disorders that make up "Syndrome X" are provided.

Additionally, the instant invention also provides a method for preventing or reducing the risk of hyperglycemia, insulin resistance or diabetes development in a patient, comprising the administration of a prophylactically effective amount of a compound or composition of the present invention to a patient at risk for such an event. The patient may already be obese, (BMI of 30.0 or greater), overweight (BMI of 25.0 to 30.0) or possess other risk factors for developing diabetes including age, family history and physical inactivity.

Further provided herein are methods for the treatment, prevention, or amelioration of one or more symptoms of cholestasis, as well as for the treatment of the complications of cholestasis by administering a compound or composition provided herein.

Cholestasis is typically caused by factors within the liver (intrahepatic) or outside the liver (extrahepatic) and leads to the accumulation of bile salts, bile pigment bilirubin, and lipids in the blood stream instead of being eliminated normally.

Intrahepatic cholestasis is characterized by widespread blockage of small ducts or by disorders, such as hepatitis, that impair the body's ability to eliminate bile. Intrahepatic cholestasis may also be caused by alcoholic liver disease, primary binary cirrhosis, cancer that has spread (metastasized) from another part of the body, primary sclerosing cholangitis, gallstones, biliary colic and acute cholecystitis. It can also occur as a complication of surgery, serious injury, cystic fibrosis, infection, or intravenous feeding or be drug induced. Cholestasis may also occur as a complication of pregnancy and often develops during the second and third trimesters.

Extrahepatic cholestasis is most often caused by choledocholithiasis (Bile Duct Stones), benign biliary strictures (noncancerous narrowing of the common duct), cholangiocarcinoma (ductal carcinoma), and pancreatic carcinoma. Extrahepatic cholestasis can occur as a side effect of many medications.

Accordingly, compounds or compositions provided herein may be used for the treatment, prevention, or amelioration of one or more symptoms of intrahepatic or extrahepatic cholestasis, including without limitation, biliary artesia, obstetric cholestasis, neonatal cholestasis, drug induced cholestasis, cholestasis arising from Hepatitis C infection, chronic cholestatic liver disease such as primary biliary cirrhosis (PBC) and primary sclerosing cholangitis (PSC).

Further provided by this invention are methods for treating obesity, as well as treating the complications of obesity, by administering a compound or composition of the present invention. The terms "obese" and "obesity" refers to, according to the World Health Organization, a Body Mass Index (BMI) greater than 27.8 kg/m$^2$ for men and 27.3 kg/m$^2$ for women (BMI equals weight (kg)/height (m$^2$). Obesity is linked to a variety of medical conditions including diabetes and an atherosclerotic disease event. (See, e.g., Barrett-Conner, E., Epidemol. Rev. (1989) 11: 172-181; and Knowler, et al., Am. J. Clin. Nutr. (1991) 53:1543-1551). Accordingly the claimed compounds or compositions that may be used for treating obesity or its complications, and can be identified, formulated, and administered as previously described above.

G. Combination Therapy

Also contemplated herein is combination therapy using one or more compounds or compositions provided herein, or a pharmaceutically acceptable derivative thereof, in combination with one or more of the following: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A: cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, LXR α or β agonists, antagonists or partial agonists, aspirin or fibric acid derivatives. The compound or composition provided herein, or pharmaceutically acceptable derivative thereof, is administered simultaneously with, prior to, or after administration of one or more of the above agents. Pharmaceutical compositions containing a compound provided herein and one or more of the above agents are also provided.

Combination therapy includes administration of a single pharmaceutical dosage formulation which contains a compound of the present invention and one or more additional active agents, as well as administration of a compound of the present invention and each active agent in its own separate pharmaceutical dosage formulation. For example, a farnesoid X receptor agonist, partial agonist, partial antagonist, or antagonist of the present invention and an HMG-CoA reductase inhibitor can be administered to the patient together in a single oral dosage composition such as a tablet or capsule, or each agent administered in separate oral dosage formulations. Where separate dosage formulations are used, the compounds described herein and one or more additional active agents can be administered at essentially the same time, i.e., concurrently, or at separately staggered times, i.e., sequentially; combination therapy is understood to include all these regimens.

An example of combination therapy that modulates, or prevents the onset of the symptoms, or associated complications of atherosclerosis, is administered with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; LXR α or β agonists, antagonists, or partial agonists, an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin.

A compound or composition of the present invention is preferably administered with a cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Other HMG-CoA reductase inhibitors can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulas of these and additional HMG-CoA reductase inhibitors that can be used in the methods of the present invention are described at page 87 of M. Yalpani, "Cholesterol Lowering Drugs," *Chemistry & Industry*, pp. 85-89 (5 Feb. 1996). In one embodiment, the HMG-CoA reductase inhibitor is selected from lovastatin and simvastatin.

Dosage information for HMG-CoA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA reductase inhibitor is from about 1 to 200 mg/day and, more preferably, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg.

Oral administration may be in a single or divided doses of two, three, or four times daily, although a single daily dose of the HMG-CoA reductase inhibitor is preferred.

Diabetic patients are likely to suffer from premature development of atherosclerotic disease events and increased rate of cardiovascular and peripheral vascular diseases. Hyperlipidemia and dyslipidemia are important precipitating factors for these diseases. See, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Dyslipidemia is characterized by abnormal levels of lipoproteins in blood plasma (e.g. elevated levels of LDL, VLDL and depressed levels of HDL), and has been shown to be one of the main contributors to the increased incidence of coronary events and deaths among diabetic subjects (see, e.g., Joslin, E. Ann. Chim. Med. (1927) 5: 1061-1079). Epidemiological studies since then have confirmed the association and have shown a several-fold increase in coronary deaths among diabetic subjects when compared with non-diabetic subjects (see, e.g., Garcia, M. J. et al., *Diabetes* (1974) 23: 105-11 (1974); and Laakso, M. and Lehto, S., Diabetes Reviews (1997) 5(4): 294-315).

The methods of the present invention can be used effectively in combination with one or more additional active anti-diabetes agents depending on the desired target therapy (see, e.g., Turner, N. et al. *Prog. Drug Res.* (1998) 51: 33-94; Haffner, S. Diabetes Care (1998) 21: 160-178; and DeFronzo, R. et al. (eds.), Diabetes Reviews (1997) Vol. 5 No. 4).

A number of studies have investigated the benefits of combination therapies with oral agents (see, e.g., Mahler, R., J. Clin. Endocrinol. Metab. (1999) 84: 1165-71; United Kingdom Prospective Diabetes Study Group: UKPDS 28, Diabetes Care (1998) 21: 87-92; Bardin, C. W., (ed.), CURRENT THERAPY IN ENDOCRINOLOGY AND METABOLISM, 6th Edition (Mosby—Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al, *Diabet. Med.* (1996) 13 365-370; Kwiterovich, P. Am. J. Cardiol (1998) 82(12A): 3U-17U). These studies indicate that the modulation of hyperlipidemia associated with diabetes can further improve the treatment outcome of diabetics.

Accordingly, another combination therapy claimed herein is suitable for treating diabetes and its related symptoms, complications, and disorders, and includes the co-administration of the compounds or compositions provided herein with for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); and related insulin sensitizers, such as selective and non-selective activators of PPARα, PPARβ, and PPARγ, LXR α or β agonists, antagonists and partial agonists, dehydroepiandrosterone (also referred to as DHEA or its conjugated sulphate ester, DHEA-SO$_4$); antiglucocorticoids; TNFα-inhibitors; α-glucosidase inhibitors (such as acarbose, miglitol, and voglibose), pramlintide (a synthetic analog of the human hormone amylin), other insulin secretogues (such as repaglinide, gliquidone, and nateglinide), insulin, as well as the active agents discussed above for treating atherosclerosis.

Another example of combination therapy claimed herein is the co-administration of the claimed compounds or compositions provided herein with compounds or compositions for treating obesity or obesity-related disorders, wherein the claimed compounds can be effectively used in combination with, for example, phenylpropanolamine, phentermine, diethylpropion, mazindol; fenfluramine, dexfenfluramine, phentiramine, $\beta_3$ adrenoceptor agonist agents; sibutramine, gastrointestinal lipase inhibitors (such as orlistat), LXR (or p agonists, antagonists and partial agonists, and leptins. Other agents used in treating obesity or obesity-related disorders include neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Another example of a claimed combination therapy is the co-administration of the claimed compound or composition provided herein with compounds or compositions for treating cholestasis and its related symptoms, complications, and disorders. Such co-administered compounds include for example, Actigall (Ursodeoxycholic acid—UDCA), corticosteroids, anti-infective agents (Rifampin, Rifadin, Rimactane), anti-viral agents, Vitamin D, Vitamin A, phenobarbital, cholestyramine, UV light, antihistamines, oral opiate receptor antagonists and biphosphates, for the treatment, prevention, or amelioration of one or more symptoms of intrahepatic or extrahepatic cholestasis. Dosage information for these agents is well known in the art.

The following examples are provided for illustrative purposes only and are not intended to limit the scope of the invention.

Example 1

Preparation of 3-amino-4-ethylaminobenzonitrile

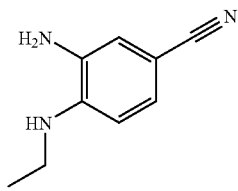

A. To a solution of 4-fluoro-3-nitrobenzonitrile (5.0 g, 30 mmol) in THF (15 mL, anhyd) was added a solution of ethylamine (2.0 M, 23 mL, 46 mmol) in THF. After stirring 16 h, precipitated solids were collected by filtration, triturated with a mixture of THF-hexanes (1:1, 50 mL), filtered again and dried under vacuum to give 4-ethylamino-3-nitrobenzonitrile (4.7 g, 82%) as a yellow solid. $^1$H-NMR (CDCl$_3$): $\delta$ 8.51 (1H, d), 8.34 (1H, br s), 7.62 (1H, dd), 6.93 (1H, d), 3.44 (2H, m), 1.42 (3H, t).

A 250 mL pressure flask was sparged with a stream of nitrogen and then charged with 4-ethylamino-3-nitrobenzonitrile (1.6 g, 8.5 mmol), EtOAc (35 mL) and 10% w/w Pd/C (1.0 g, 11 mol %). The pressure flask was affixed to a Parr hydrogenation apparatus, evacuated briefly and back-filled with argon (2 cycles), then evacuated briefly and back-filled with hydrogen (3 cycles). The flask was pressurized to 50 psi of hydrogen and shaken vigorously. After 3 h, the flask was vented and sparged with a stream of nitrogen for 5 min. The reaction mixture was filtered through Celite and concentrated under reduced pressure to give the title product (1.4 g, quant.) as a pale brown solid. $^1$H-NMR (CDCl$_3$): $\delta$ 7.14 (1H, dd), 6.91 (1H, d), 6.56 (1H, d), 3.91 (1H, br s), 3.32 (2H, br s), 3.19 (2H, q), 1.31 (3H, t).

Preparation of 3-(3-benzyl-4-oxothiazolidin-2-ylideneamino)-4-ethylamino-benzonitrile

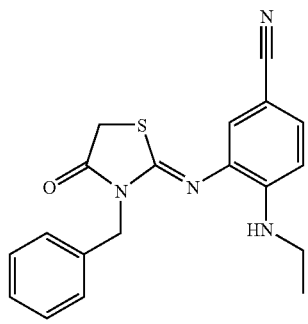

B. To a solution of 3-amino-4-ethylamino-benzonitrile (1.0 g, 6.2 mmol) in THF (50 mL, anhyd) was added benzyl-isothiocyanate (0.92 g, 6.2 mmol). The reaction mixture was heated at 50° C. with stirring. After 6 h, the reaction mixture was cooled, concentrated under reduced pressure, and chromatographed (silica gel, 1:1 EtOAc/Hex) to yield 1-benzyl-3-(5-cyano-2-ethylaminophenyl)thiourea (1.78 g, 93%). $^1$H-NMR (CDCl$_3$): $\delta$ 7.48 (1H, dd), 7.37 (1H, d), 7.31 (3H, m), 7.24 (1H, s), 7.18 (1H, br), 6.67 (1H, d), 5.95 (1H, br), 4.81 (2H, d), 4.68 (1H, br), 3.19 (2H, m), 1.23 (3H, t).

To a solution of 1-benzyl-3-(5-cyano-2-ethylaminophenyl)thiourea (1.0 g, 3.2 mmol) in ethanol (40 mL, anhyd) was added ethyl chloroacetate (0.39 g, 3.2 mmol) and then DBU (0.58 g, 3.8 mmol). The reaction mixture was heated at 80° C. with stirring. After 1 h the reaction mixture was cooled, concentrated under reduced pressure, and chromatographed (silica gel, 1:1 EtOAc/Hex) to afford the title product (0.98 g, 87%). $^1$H-NMR (CDCl$_3$): $\delta$ 7.38 (6H, m), 7.11 (1H, d), 6.50 (1H, d), 5.05 (2H, s), 3.96 (2H, s), 3.01 (2K, m), 1.03 (3H, t).

Preparation of 3-{3-Benzyl 5-[(N-methyl-phenylamino)-methylene]-4-oxothiazolidin-2-ylideneamino}-4-ethylamino-benzonitrile

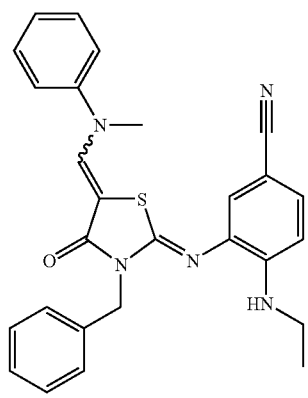

C. To a mixture of trimethyl orthoformate (TMOF)-toluene (1:1, 1.5 mL, anhyd) was added N-methylaniline (43 µL, 0.40 mmol) and 3-(3-benzyl-4-oxothiazolidin-2-ylideneamino)-4-ethylamino-benzonitrile (88 mg, 0.25 mmol). The reaction mixture was heated at reflux for 24 h, cooled and purified by reverse-phase HPLC (C18 column), eluting with 0.05% TFA in MeCN—H$_2$O (1:9 to 9:1) to afford the title product (68 mg, 58%) as a yellow solid. $^1$H-NMR (CDCl$_3$): δ 7.95 (1H, s), 7.27-7.43 (8H, m), 7.24 (1H, dd), 7.15-7.19 (2H, m), 7.07 (1H, d), 6.44 (1H, d), 5.10 (2H, s), 3.54 (3H, s), 2.97 (2H, q), 0.99 (3H, t); MS (ESI): 468 (MH$^+$).

D. In a similar manner, as described for Example 1C, but replacing N-methylaniline with the appropriate amine, the following compounds were prepared:

3-{3-benzyl-5-[(N-benzyl-methylamino)-methylene]-4-oxothiazolidin-2-ylideneamino}-4-ethylamino-benzonitrile; $^1$H-NMR (CDCl$_3$): δ 7.82 (1H, s), 7.20-7.42 (11H, m), 7.12 (1H, d), 6.45 (1H, d), 5.11 (2H, s), 4.45 (2H, s), 4.14 (1H, br t), 3.04 (3H, s), 2.98 (2H, m), 1.00 (3H, t); MS (ESI): 482 (MH$^+$);

3-[3-benzyl-5-(2,3-dihydroindol-1-ylmethylene)-4-oxothiazolidin-2-ylideneamino]-4-ethylamino-benzonitrile; $^1$H-NMR (CDCl$_3$): δ 8.21 (1H, s), 7.24-7.44 (6H, m), 7.15-7.24 (3H, m), 7.05 (1H, d), 7.01 (1H, app t), 6.49 (1H, d), 5.14 (2H, s), 4.27 (2H, t), 4.15 (1H, br s), 3.26 (2H, t), 3.00 (2H, q), 1.01 (3H, t); MS (ESI): 480 (MH$^+$);

3-{3-benzyl-5-[(4-methoxyphenylamino)-methylene]-4-oxothiazolidin-2-ylideneamino}-4-ethylamino-benzonitrile; $^1$H-NMR (CDCl$_3$): δ 8.01 (1H, d), 7.27-7.43 (6H, m), 7.17 (1H, d), 6.95-7.01 (2H, m), 6.86-6.92 (2H, m), 6.49 (1H, d), 6.14 (1H, d), 5.12 (2H, s), 3.80 (3H, s), 3.00 (2H, q), 1.01 (3H, t); MS (ESI): 484 (MH$^+$);

3-(3-benzyl-5-{[N-(4-methoxyphenyl)-methylamino]-methylene}-4-oxothiazolidin-2-ylideneamino)-4-ethylamino-benzonitrile; $^1$H-NMR (CDCl$_3$): δ 7.85 (1H, s), 7.27-7.40 (6H, m), 7.23 (1H, dd), 7.08-7.13° (2H, m), 7.04 (1H, d), 6.88-6.93 (2H, m), 6.48 (1H, d), 5.12 (2H, s), 3.84 (3H, s), 3.49 (3H, s), 2.96 (2H, q), 0.99 (3H, t); MS (ESI): 498 (MH$^+$);

3-(3-benzyl-5-{[N-(2-methoxyphenyl)-methylamino]-methylene}-4-oxothiazolidin-2-ylideneamino)-4-ethylamino-benzonitrile; $^1$H-NMR (CDCl$_3$): δ 7.79 (1H, s), 7.25-7.42 (6H, m), 7.18 (1H, dd), 7.13 (1H, dd), 6.94-6.99 (3H, m), 6.39 (1H, d), 5.04 (2H, s), 3.86 (3H, s), 3.42 (3H, s), 2.94 (2H, q), 0.97 (3H, t); MS (ESI): 498 (MH$^+$);

Example 2

Preparation of 3'-amino-4'-ethylamino-acetophenone

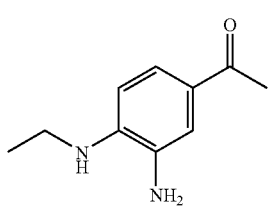

A. In a manner similar to Example 1A, 5-acetyl-2-ethylamino-aniline was prepared by replacing 4-fluoro-3-nitrobenzonitrile with 4'-chloro-3'-nitroacetophenone. $^1$H-NMR (CDCl$_3$): δ 7.52 (1H, dd), 7.39 (1H, d), 6.58 (1H, d), 3.94 (1H, br s), 3.30 (2 h, br s), 3.24 (2H, q), 2.50 (3H, s), 1.33 (3H, t).

Preparation of 3-benzyl-5-[(N-methyl-phenylamino)-methylene]-2-thioxothiazolidin-4-one

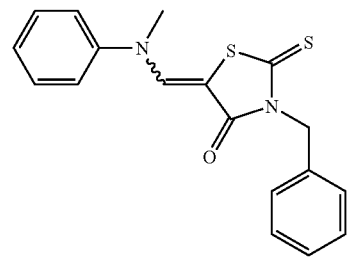

B. To a mixture of TMOF-toluene (1:1, 6 mL, anhyd) was added N-methylaniline (0.33 mL, 3.0 mmol) and 3-benzyl-rhodanine (0.67 g, 3.0 mmol). After heating at reflux for 2 h, the reaction mixture was cooled, concentrated and chromatographed (silica gel, 0:100 to 40:60 EtOAc-Hex) to yield the title product (0.40 g, 39%) as a yellow solid. $^1$H-NMR (CDCl$_3$): δ 7.79 (1H, s), 7.34-7.47 (5H, m), 7.17-7.31 (5H, m), 5.25 (2H, s), 3.54 (3H, s).

Preparation of 2-(5-acetyl-2-ethylamino-phenylimino)-3-benzyl-5-[(N-methyl-phenylamino)-methylene]-thiazolidin-4-one

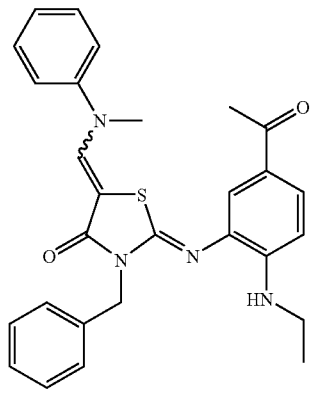

C. A mixture of 3-benzyl-5-[(N-methyl-phenylamino)-methylene]-2-thioxo-thiazolidin-4-one (0.40 g, 1.2 mmol) and methyl p-toluenesulfonate (0.26 g, 1.4 mmol) in DMF (2 mL, anhyd) was heated at 125° C. After 2 h, the reaction mixture was cooled and an aliquot (0.4 mL) of the intermediate was transferred to an oven-dried vial. The intermediate was diluted with MeCN (2 mL, anhyd) and charged with 3'-amino-4'-ethylamino-acetophenone (53 mg, 0.30 mmol). The reaction mixture was warmed to 50° C., charged with TEA (100 µL), sealed and heated at 65° C. After 16 h, the reaction mixture was cooled, concentrated and chromatographed (silica gel, 0:100 to 50:50 EtOAc-Hex) to give the title product (14 mg) as a yellow solid. $^1$H-NMR (CDCl$_3$): δ

7.92 (1H, s), 7.65 (1H, dd), 7.50 (1H, d), 7.27-7.42 (7H, m), 7.14-7.23 (3H, m), 6.48 (1H, d), 5.12 (2H, s), 4.27 (1H, br s), 3.51 (3H, s), 3.02 (2H, q), 2.45 (3H, s), 1.01 (3H, t); MS (ESI): 485 (MH$^+$).

Example 3

Preparation of 2-(5-acetyl-2-ethylamino-phenylimino)-3-benzyl-thiazolidin-4-one

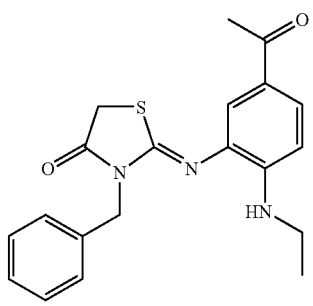

A. In a manner similar to Example 1B, the title product was prepared by replacing 3-amino-4-ethylamino-benzonitrile with 3'-amino-4'-ethylamino-acetophenone. $^1$H-NMR (CDCl$_3$): δ 7.69 (1H, dd, J=8.6 Hz, 2.0 Hz), 7.58 (1H, d, J=2.0 Hz), 7.29-7.44 (5H, m), 6.52 (1H, d, J=8.6 Hz), 5.06 (2H, s), 4.06 (1H, br s), 3.93 (2H, s), 3.06 (2H, q, J=7.2 Hz), 2.49 (3H, s), 1.06 (3H, t, J=7.2 Hz).

Preparation of 2-(5-acetyl-2-ethylamino-phenylimino)-3-benzyl-5-(2,3-dihydroindol-1-ylmethylene)-thiazolidin-4-one

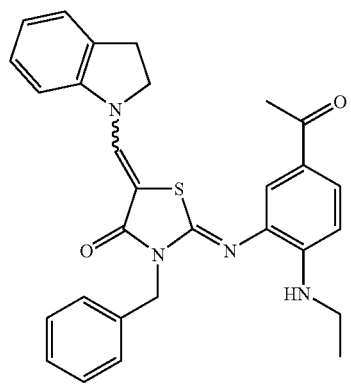

B. In a manner similar to Example 1C, indoline and 2-(5-acetyl-2-ethylamino-phenylimino)-3-benzyl-thiazolidin-4-one were condensed to yield the title product. $^1$H-NMR (CDCl$_3$): δ 8.19 (1H, s), 7.68 (1H, dd), 7.61 (1H, d), 7.44 (2H, m), 7.15-7.39 (5H, m), 7.03 (1H, d), 6.98 (1H, app t), 6.51 (1H, d), 5.16 (2H, s), 4.22 (2H, t), 4.17 (1H, br s), 3.20 (2H, t), 3.05 (2H, q), 2.51 (3H, s), 1.04 (3H, t); MS (ESI): 497 (MH$^+$).

C. In a manner similar as described for Example 3B, but replacing indoline with the appropriate amine, the following compounds were prepared:

2-(5-acetyl-2-ethylamino-phenylimino)-3-benzyl-5-{[N-(4-methoxyphenyl)-methylamino]-methylene}-thiazolidin-4-one; $^1$H-NMR (CDCl$_3$): δ 7.82 (1H, s), 7.62 (1H, dd), 7.47 (1H, d), 7.27-7.40 (5H, m), 7.10 (2H, m), 6.87 (2H, m), 6.45 (1H, d), 5.09 (2H, s), 4.22 (1H, br s), 3.77 (3H, s), 3.46 (3H, s), 3.00 (2H, q), 2.43 (3H, s), 1.00 (3H, t); MS (ESI): 515 (MH$^+$); and 2-(5-acetyl-2-ethylamino-phenylimino)-3-benzyl-5-{[N-(3-methoxyphenyl)-methylamino]-methylene}-thiazolidin-4-one; $^1$H-NMR (CDCl$_3$): δ 7.91 (1H, s), 7.65 (1H, dd), 7.51 (1H, d), 7.24-7.43 (6H, m), 6.74 (2H, m), 6.66 (1H, app t), 6.48 (1H, d), 5.12 (2H, s), 3.80 (3H, s), 3.49 (3H, s), 3.02 (2H, q), 2.46 (3H, s), 1.01 (3H, t); MS (ESI): 515 (MH$^+$).

Example 4

Preparation of 3-(3-benzyl-5-dimethylaminomethylene-4-oxothiazolidin-2-ylideneamino)-4-ethylamino-benzonitrile

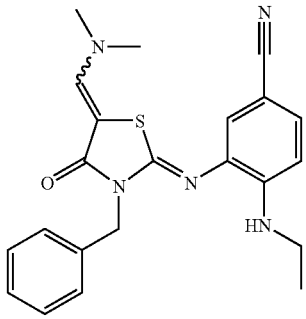

A. To a solution of 3-(3-benzyl-4-oxothiazolidin-2-ylideneamino)-4-ethylamino-benzonitrile (84 mg, 0.24 mmol) in toluene (1.0 mL, anhyd) was added N,N-dimethylformamide dimethyl acetal (1.0 mL, 7.5 mmol). The reaction mixture was heated at 125° C. After 20 h, the mixture was cooled and chromatographed (silica gel, DCM) to afford the title product (60 mg, 62%) as a pale yellow solid. $^1$H-NMR (CDCl$_3$): δ 7.60 (1H, s), 7.24-7.40 (6H, m), 7.15 (1H, d), 6.46 (1H, d), 5.09 (2H, s), 4.14 (1H, br t), 3.12 (6H, s), 2.98 (2H, m), 0.99 (3H, t); MS (ESI): 406 (MH$^+$).

B. In a similar manner, but replacing 3-(3-benzyl-4-oxothiazolidin-2-ylideneamino)-4-ethylamino-benzonitrile with 2-(5-acetyl-2-ethylamino-phenylimino)-3-benzyl-thiazolidin-4-one, the following compound was prepared:

2-(5-acetyl-2-ethylamino-phenylimino)-3-benzyl-5-dimethylaminomethylene-thiazolidin-4-one; $^1$H-NMR (CDCl$_3$): δ 7.66 (1H, dd), 7.59 (1H, d), 7.58 (1H, s), 7.27-7.42 (5H, m), 6.49 (1H, d), 5.11 (2H, s), 4.16 (1H, br t), 3.08 (6H, s), 3.03 (2H, m), 2.49 (3H, s), 1.02 (3H, t); MS (ESI): 423 (MH+).

Example 5

Preparation of 2-(5-acetyl-2-ethylamino-phenylimino)-3-benzyl-5-(4-methylpiperazin-1-ylmethylene)-thiazolidin-4-one

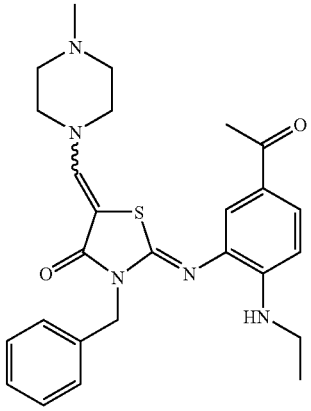

A. A mixture of 1-methylpiperazine (0.22 mL, 2.0 mmol) in N,N-dimethylformamide dimethyl acetal (1.5 mL) was heated at 100° C. After 3 h, the mixture was concentrated under reduced pressure and diluted with toluene (2 cycles), and then concentrated under vacuum. Next an aliquot (80 μL) of the concentrated intermediate was added to a solution of 2-(5-acetyl-2-ethylamino-phenylimino)-3-benzyl-thiazolidin-4-one (60 mg, 0.16 mmol) in toluene (1.0 mL, anhyd). After heating at 120° C. for 1 h, the mixture was cooled, concentrated and chromatographed (silica gel, DCM to 0.2:10:89.8 DEA/MeOH/DCM) to yield the title product (61 mg, 78%) as a yellow solid. ¹H-NMR (CDCl₃): δ 7.66 (1H, dd), 7.58 (1H, d), 7.55 (1H, s), 7.27-7.42 (5H, m), 6.49 (1H, d), 5.11 (2H, s), 4.12 (1H, br t), 3.45 (4H, br t), 3.03 (2H, m), 2.49 (3K, s), 2.43 (4H, br t), 2.30 (3H, s), 1.02 (3H, t); MS (ESI): 478 (MH+).

B. In a similar manner as described above, but replacing 1-methylpiperazine with the appropriate amine, the following compounds were prepared:

2-(5-acetyl-2-ethylamino-phenylimino)-3-benzyl-5-[(N-benzyl-methylamino)-methylene]-thiazolidin-4-one; ¹H-NMR (CDCl₃): δ 7.80 (1H, s), 7.64 (1H, dd), 7.56 (1H, d), 7.28-7.45 (8H, m), 7.21 (2H, m), 6.48 (1H, d), 5.13 (2H, s), 4.42 (2H, s), 4.20 (1H, br s), 3.03 (2H, q), 3.00 (3H, s), 2.44 (3H, s), 1.03 (3H, t); MS (ESI): 499 (MH+);

2-(5-acetyl-2-ethylamino-phenylimino)-3-benzyl-5-{[(3-dimethylaminopropyl)-methylamino]-methylene}-thiazolidin-4-one; ¹H-NMR (CDCl₃): δ 7.65 (1H, dd), 7.63 (1H, s), 7.60 (1H, d), 7.27-7.43 (5H, m), 6.49 (1H, d), 5.11 (2H, s), 4.19 (1H, br t), 3.31 (2H, t), 3.10 (3H, s), 3.03 (2H, m), 2.48 (3H, s), 2.29 (2H, br s), 2.23 (6H, br s), 1.76 (2H, br t), 1.02 (3H, t); MS (ESI): 494 (MH+); and 2-(5-acetyl-2-ethylamino-phenylimino)-3-benzyl-5-[(N-methyl-phenethylamino)-methylene]-thiazolidin-4-one; ¹H-NMR (CDCl₃): δ 7.67 (1H, dd), 7.62 (1H, d), 7.56 (1H, s), 7.20-7.43 (8H, m), 7.15 (2H, m), 6.51 (1H, d), 5.12 (2H, s), 4.31 (1H, br s), 3.46 (2H, br t), 3.03 (3H, m), 2.88 (2H, m), 2.49 (3H, s), 1.03 (3H, t); MS (ESI): 513 (MH+).

Example 6

Preparation of 3-benzyl-5-{[N-(4-methoxyphenyl)-methylamino]-methylene}-2-thioxothiazolidin-4-one

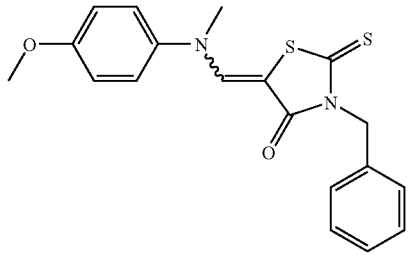

A. In a manner similar to Example 2B, the title product was prepared by replacing N-methylaniline with N-methyl-p-anisidine. ¹H-NMR (CDCl₃): δ 7.73 (1H, s), 7.44 (2H, d), 7.23-7.30 (3H, m), 7.12 (2H, m), 6.94 (2H, m), 5.23 (2H, s), 3.85 (3H, s), 3.49 (3H, s).

Preparation of 3-benzyl-5-({N-[4-(2-methoxyethoxy)-phenyl]-methylamino}-methylene)-2-thioxothiazolidin-4-one

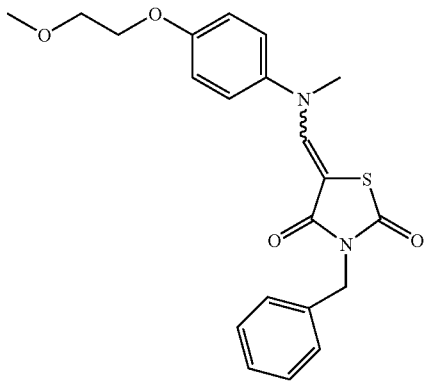

B. To a stirred solution of 3-benzyl-5-{[N-(4-methoxyphenyl)-methylamino]-methylene}-2-thioxothiazolidin-4-one (0.25 g, 0.67 mmol) in DCM (6 mL, anhyd) chilled to −78° C. was added dropwise a 1.0 M solution of boron tribromide in DCM (4.0 mL, 4.0 mmol). The reaction flask was removed from the dry-ice bath and allowed to warm to ambient temperature. After 4 h the reaction flask was chilled again to −78° C., and the reaction mixture was quenched by addition of MeOH (30 mL). The reaction mixture then was concentrated under reduced pressure and chromatographed (silica gel, DCM) to afford 3-benzyl-5-{[N-(4-hydroxyphenyl)-methylamino]-methylene}-2-thioxothiazolidin-4-one (0.16 g, 67%) as a yellow solid. ¹H-NMR (CDCl₃): δ 7.73 (1H, s), 7.44 (2H, d), 7.23-7.31 (3H, m), 7.07 (2H, m), 6.89 (2H, m), 5.30 (1H, s), 5.24 (2H, s), 3.49 (3H, s).

To a solution of 3-benzyl-5-{[N-(4-hydroxyphenyl)-methylamino]-methylene}-2-thioxothiazolidin-4-one (71 mg, 0.20 mmol) in DMF (1.0 mL, anhyd) was added anhyd K₂CO₃ (29 mg, 0.21 mmol) and 2-bromoethyl methyl ether (20 μL, 0.21 mmol). The reaction mixture was heated at 50° C. After 20 h the reaction mixture was cooled, diluted with CHCl₃ (50 mL), washed with H₂O (3×25 mL) and brine, dried over anhyd Na₂SO₄, concentrated and then chromatographed (silica gel, 0:100 to 20:80 EtOAc-DCM) to give the title product (60 mg, 73%) as a yellow solid. ¹H-NMR (CDCl₃): δ 7.73 (1H, s), 7.44 (2H, d), 7.21-7.30 (3H, m), 7.11 (2H, d), 6.97 (2H, d), 5.23 (2H, s), 4.15 (2H, m), 3.79 (2H, m), 3.48 (3H, s), 3.47 (3H, s).

Preparation of 2-(5-acetyl-2-ethylamino-phenylimino)-3-benzyl-5-({N-[4-(2-methoxy-ethoxy)-phenyl]-methylamino}-methylene)-thiazolidin-4-one

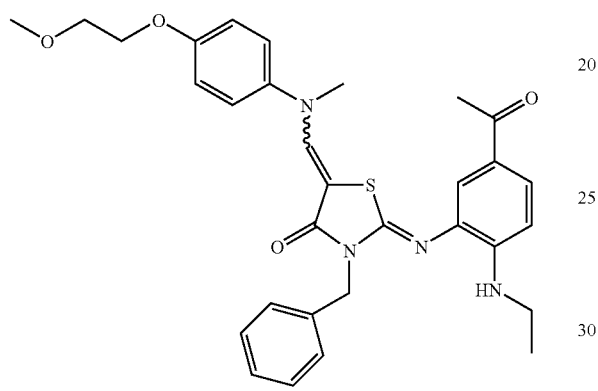

C. A mixture of 3-benzyl-5-({N-[4-(2-methoxy-ethoxy)-phenyl]-methylamino}-methylene)-2-thioxothiazolidin-4-one (60 mg, 0.14 mmol) and methyl p-toluenesulfonate (54 mg, 0.29 mmol) in DMF (1.0 mL, anhyd) was heated at 130° C. After 2 h the reaction mixture was allowed to cool to ambient temperature, charged with 3'-amino-4'-ethylamino-acetophenone (50 mg, 0.28 mmol) and TEA (70 μL, 0.72 mmol), and then heated at 65° C. After 20 h the reaction mixture was cooled and chromatographed (HPLC-MS conditions) to yield the title product (7 mg) as a yellow solid. ¹H-NMR (CDCl₃): δ 7.82 (1H, s), 7.61 (1H, dd), 7.48 (1H, d), 7.27-7.40 (5H, m), 7.08 (2H, m), 6.90 (2H, m), 6.44 (1H, d), 5.09 (2H, s), 4.20 (1H, br s), 4.07 (2H, m), 3.73 (2H, m), 3.46 (3H, s), 3.44 (3H, s), 3.00 (2H, m), 2.43 (3H, s), 1.00 (3H, t); MS (ESI): 559 (MH⁺).

Example 7

Preparation of 2-(3-acetylphenylimino)-3-furan-2-ylmethyl-thiazolidin-4-one

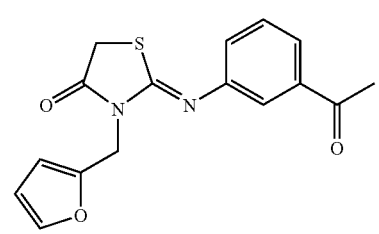

A. In a manner similar to Example 1B, the title compound was prepared from 2-furfurylisothiocyanate and 3'-aminoacetophenone. ¹H-NMR (CDCl₃): δ 7.74 (1H, m), 7.56 (1H, app t), 7.45 (1H, app t), 7.38 (1H, dd), 7.17 (1H, m), 6.42 (1H, d), 6.35 (1H, dd), 5.04 (2H, s), 3.85 (2H, s), 2.61 (3H, s).

Preparation of 2-(3-acetylphenylimino)-5-(2,3-dihydroindol-1-ylmethylene)-3-furan-2-ylmethyl-thiazolidin-4-one

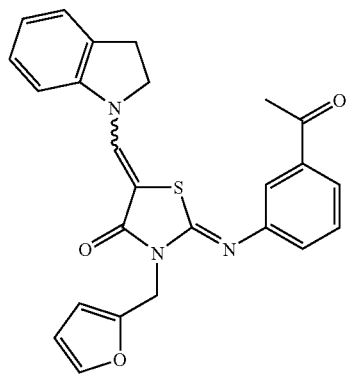

B. In a manner similar to Example 1C, indoline and 2-(3-acetylphenylimino)-3-(furan-2-ylmethyl)-thiazolidin-4-one were condensed to yield the title product. ¹H-NMR (CDCl₃): δ 8.13 (1H, s), 7.73 (1H, m), 7.58 (1H, m), 7.45 (1H, app t), 7.39 (1H, m), 7.15-7.23 (3H, m), 6.95-7.01 (2H, m), 6.43 (1H, d), 6.34 (1H, dd), 5.13 (2H, s), 4.16 (2H, t), 3.17 (2H, t), 2.62 (3H, s); MS (ESI): 443 (MH⁺).

Example 8

Preparation of N-[4-(3-furan-2-ylmethyl-4-oxothiazolidin-2-ylideneamino)-phenyl]-acetamide

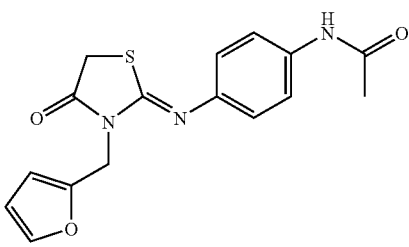

A. In a manner similar to Example 1B, the title compound was prepared from 2-furfurylisothiocyanate and 4'-aminoacetanilide. ¹H-NMR (CDCl₃): δ 7.49 (2H, d), 7.37 (1H, m), 7.17 (1H, br s), 6.94 (2H, d), 6.41 (1H, d), 6.33 (1H, dd), 5.03 (2H, s), 3.83 (2H, s), 2.18 (3H, s).

Preparation of N-{4-[5-(2,3-dihydroindol-1-ylmethylene)-3-furan-2-ylmethyl-4-oxothiazolidin-2-ylideneamino]-phenyl}-acetamide

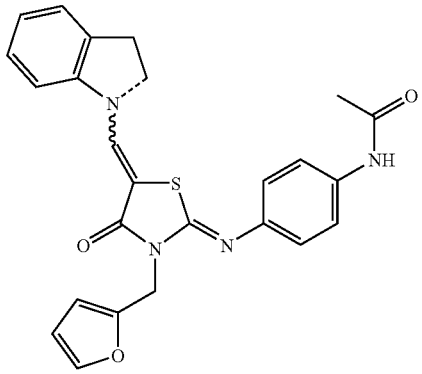

B. In a manner similar to Example 1C, indoline and N-[4-(3-furan-2-ylmethyl-4-oxothiazolidin-2-ylideneamino)-phenyl]-acetamide were condensed to yield the title product. ¹H-NMR (CDCl₃): δ 8.11 (1H, s), 7.48 (2H, d), 7.37 (1H, m), 7.14-7.23 (3H, m), 6.94-7.00 (4H, m), 6.42 (1H, d), 6.32 (1H, dd), 5.12 (2H, s), 4.18 (2H, t), 3.18 (2H, t), 2.19 (3H, s); MS (ESI): 459 (MH⁺).

Example 9

Preparation of 2-(5-acetyl-2-ethylamino-phenylimino)-3,5-dibenzyl-thiazolidin-4-one

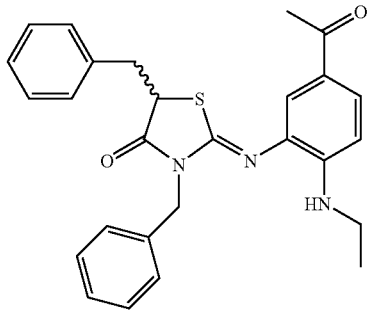

A. To a stirred solution of 2-(5-acetyl-2-ethylamino-phenylimino)-3-benzyl-thiazolidin-4-one (0.11 g, 0.30 mmol) in THF (3 mL, anhyd) chilled to 0° C. was added dropwise 1.0 M solution of lithium bis(trimethylsilyl)amide in THF (0.30 mL, 0.30 mmol). After 5 min benzyl bromide (36 µL, 0.30 mmol) was added to the reaction mixture, which was stirred at 0° C. for 2 h and then allowed to warm to ambient temperature. After 1 h the reaction mixture was quenched with satd NH₄Cl and extracted with EtOAc. The organic layer was isolated, washed with brine, dried over anhyd Na₂SO₄, concentrated and chromatographed (silica gel, 0:100 to 20:80 EtOAc-Hex) to yield the title product (11 mg) as a white solid.

¹H-NMR (CDCl₃): δ 7.66 (1H, dd, J=8.5 Hz, 2.0 Hz), 7.49 (1H, d, J=2.0 Hz), 7.19-7.35 (10H, m), 6.48 (1H, d, J=8.5 Hz), 5.00 (2H, m), 4.48 (1H, dd, J=9.0 Hz, 3.8 Hz), 3.92 (1H, hr t), 3.53 (1H, dd, J=14.1 Hz, 3.8 Hz), 3.17 (1H, dd, J=14.1 Hz, 9.0 Hz), 3.02 (2H, m), 2.47 (3H, s), 1.02 (3H, t); MS (ESI): 458 (MH⁺).

B. In a similar manner as described above, the following compounds were prepared by replacing benzyl bromide with either (2-iodoethyl)benzene or 2-bromoacetophenone, respectively:

2-(5-acetyl-2-ethylamino-phenylimino)-3-benzyl-5-phenethyl-thiazolidin-4-one; ¹H-NMR (CDCl₃): δ 7.70 (1H, dd), 7.60 (1H, d), 7.26-7.39 (7H, m), 7.15-7.24 (3H, m), 6.52 (1H, d), 5.03 (2H, m), 4.10 (1H, dd), 4.06 (1H, br s), 3.05 (2H, m), 2.78-2.87 (1H, m), 2.66-2.75 (1H, m), 2.53-2.63 (1H, m), 2.51 (3H, s), 2.11-2.22 (1H, m), 1.04 (1H, t); MS (ESI): 472 (MH⁺); and 2-(5-acetyl-2-ethylamino-phenylimino)-3-benzyl-5-(2-oxo-2-phenylethyl)-thiazolidin-4-one; ¹H-NMR (CDCl₃): δ 7.65 (1H, dd), 7.32-7.48 (1H, m), 6.49 (1H, d), 5.19 (2H, s), 4.83 (2H, br s), 4.28 (1H, br s), 3.04 (2H, q), 2.43 (3H, s), 1.05 (3H, t); MS (ESI): 486 (MH⁺).

Example 10

Preparation of 2-(5-acetyl-2-ethylamino-phenylimino)-3-benzyl-5-benzylidene-thiazolidin-4-one

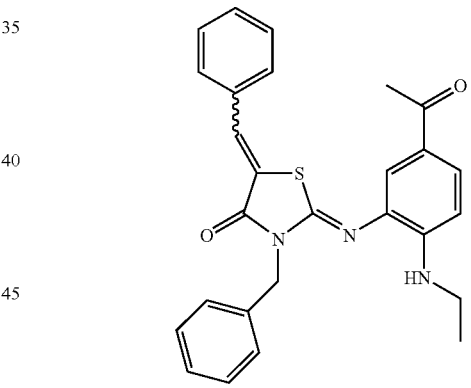

A. A mixture of 3-benzylrhodanine (0.50 g, 2.2 mmol), benzaldehyde (0.23 mL, 2.3 mmol) and TEA (0.68 mL, 4.9 mmol) in MeCN (5 mL, anhyd) was heated at reflux. After 2 h the reaction mixture was cooled. Precipitated solids were collected by filtration, triturated with MeCN-Hex and dried under vacuum to yield 3-benzyl-5-benzylidene-2-thioxothiazolidin-4-one, which was used without further purification.

In a manner similar to Example 6C, but replacing 3-benzyl-5-({N-[4-(2-methoxy-ethoxy)-phenyl]-methylamino}-methylene)-2-thioxothiazolidin-4-one with 3-benzyl-5-benzylidene-2-thioxothiazolidin-4-one, the title product was prepared. ¹H-NMR (CDCl₃): δ 7.86 (1H, s), 7.74 (1H, dd, J=8.6 Hz, 2.0 Hz), 7.57 (1H, d, J=2.0 Hz), 7.32-7.50 (10H, m), 6.55 (1H, d, J=8.6 Hz), 5.21 (2H, s), 3.07 (2H, q, J=7.2 Hz), 2.52 (3H, s), 1.06 (3H, t, J=7.2 Hz); MS (ESI): 456 (MH⁺).

B. In a similar manner as described above, but replacing benzaldehyde with 2-furaldehyde, the following compound was prepared:

2-(5-acetyl-2-ethylamino-phenylimino)-3-benzyl-5-furan-2-ylmethylene-thiazolidin-4-one; $^1$H-NMR (CDCl$_3$): δ 7.73 (1H, dd, J=8.6 Hz, 2.0 Hz), 7.57-7.61 (3H, m), 7.30-7.46 (5H, m), 6.71 (1, d, J=3.5 Hz), 6.54 (1H, d, J=8.6 Hz), 6.52 (1H, dd, J=3.5 Hz, 1.8 Hz), 5.18 (2H, s), 3.06 (2H, q, J=7.2 Hz), 2.52 (3H, s), 1.05 (J=7.2 Hz); MS (ESI): 446 (MH$^+$).

Example 11

Time Resolved Fluorescence Resonance Energy Transfer (TR-FRET) Assay

The TR-FRET assay was performed by incubating 8 nM of GST-farnesoid X receptor-LBD (comprising glutathione-5-transferase fused in frame to the farnesoid X receptor ligand binding domain, (amino acids 244-471 of the human farnesoid X receptor)), 8 nM of Europium-labeled anti-GST antibody (Wallac/PE Life Sciences Cat#AD0064), 16 nM biotin-SRC-1 peptide [5'-biotin-CPSSHSSLTERHKILHRLLQEGSPS-CONH2], 20 nM APC-SA [allophycocyanin conjugated streptavidin] (Wallac/PE Life Sciences, Cat# AD0059A) in FRET assay buffer (20 mM KH$_2$PO$_4$/K$_2$HPO$_4$ (pH 7.3), 150 mM NaCl, 2 mM CHAPS, 2 mM EDTA, 1 mM DTT) in the presence of the test compound(s) for 2-4 hours at room temperature in a 384 well assay plate. Data was collected using an LJL Analyst using the standard operating instructions and conditions with readings at emission wavelengths of 615 nm and 665 nm after a delay of 65 μs and an excitation wavelength of 330 nm.

Example 12

Co-Transfection Assay

The basic co-transfection protocol for measuring the farnesoid X receptor activity is as follows. CV-1 African Green Monkey Kidney cells were plated 24 hours before transfection to achieve approximately 70-80 percent confluency. Cells were transfected with the following expression vectors, CMX-farnesoid X receptor (full length human farnesoid X receptor), CMX-7RXRα (full length human RXR), Luc12 (ECREx7-Tk-Luciferase) luciferase reporter gene construct. (See WO 00/76523, Venkateswaran et al., (2000) J. Biol. Chem. 275 14700-14707). A CMX-β-Galactosidase expression vector was used as a transfection control. The transfection reagent used was DOTAP (Boehringer Mannheim). Cells were incubated with the DOTAP/DNA mixture for 5 hours after which the cells were harvested and plated onto either 96 well or 384 well plates containing the appropriate concentration of test compound. The assay was allowed to continue for an additional 18-20 hours, after which the cells were lysed, with lysis buffer (1% triton X 100, 10% glycerol, 5 mM Dithiothreitol, 1 mM EGTA, 25 mM Tricine, pH 7.8) and the luciferase activity measured in the presence of Luciferase assay buffer (0.73 mM ATP, 22.3 mM Tricine, 0.11 mM EGTA, 0.55 mM Luciferin, 0.15 mM Coenzyme A, 0.5 mM HEPES, 10 mM Magnesium sulphate) on a standard luminomter plate reader (PE Biosystems, NorthStar Reader), using recommended operating instructions and conditions Results of Example 11 and 12

Both the farnesoid X receptor/ECREx7 co-transfection assay (Example 9) and the TR-FRET assay (Example 8) can be used to establish the EC$_{50}$/IC$_{50}$ values for potency and percent activity or inhibition for efficacy. Efficacy defines the activity of a compound relative to a high control (chenodeoxycholic acid, CDCA) or a low control (DMSO/vehicle). The dose response curves are generated from an 8 point curve with concentrations differing by ½ LOG units. Each point represents the average of 4 wells of data from a 384 well plate. The curve for the data is generated by using the equation:

$$Y=\text{Bottom}+(\text{Top}-\text{Bottom})/(1+10^{((\log EC50-X)*\text{HillSlope})})$$

The EC$_{50}$/IC$_{50}$ is therefore defined as the concentration at which an agonist or antagonist elicits a response that is half way between the Top (maximum) and Bottom (baseline) values. The EC$_{50}$/IC$_{50}$ values represented are the averages of at least 3 independent experiments. The determination of the relative efficacy or % control for an agonist is by comparison to the maximum response achieved by chenodeoxycholic acid that is measured individually in each dose response experiment.

For the antagonist assay, CDCA is added to each well of a 384 well plate to elicit a response. The % inhibition for each antagonist is therefore a measurement of the inhibition of the activity of CDCA. In this example, 100% inhibition would indicate that the activity of CDCA has been reduced to baseline levels, defined as the activity of the assay in the presence of DMSO only.

Most of the compounds disclosed herein and tested exhibited activity in at least one of the above assays (EC$_{50}$ or IC$_{5-6}$ less than 10 μM). Most showed activity at or below 1 μM. For example, the following compound exhibited agonist activity at or less than 1 μM EC$_{50}$ with 50-100% efficacy as measured via the co-transfection assay:

2-(3-acetylphenylimino)-5-(2,3-dihydroindol-1-ylmethylene)-3-furan-2-ylmethyl-thiazolidin-4-one;

2-(5-acetyl-2-ethylamino-phenylimino)-3-benzyl-5-[(N-methyl-phenylamino)-methylene]-thiazolidin-4-one;

N-{4-[5-(2,3-dihydroindol-1-ylmethylene)-3-furan-2-ylmethyl-4-oxothiazolidin-2-ylideneamino]-phenyl}-acetamide;

2-(5-acetyl-2-ethylamino-phenylimino)-3-benzyl-5-[(N-benzyl-methylamino)-methylene]-thiazolidin-4-one;

2-(5-acetyl-2-ethylamino-phenylimino)-3-benzyl-5-[(N-methyl-phenethylamino)-methylene]-thiazolidin-4-one;

2-(5-acetyl-2-ethylamino-phenylimino)-3-benzyl-5-benzylidene-thiazolidin-4-one; and 2-(5-acetyl-2-ethylamino-phenylimino)-3-benzyl-5-furan-2-ylmethylene-thiazolidin-4-one.

The following compound exhibited agonist activity at less than 200 nM with 100% or greater efficacy as measured via the co-transfection assay:

3-[3-benzyl-5-(2,3-dihydroindol-1-ylmethylene)-4-oxothiazolidin-2-ylideneamino]-4-ethylamino-benzonitrile; and 2-(5-acetyl-2-ethylamino-phenylimino)-3-benzyl-5-{[N-(3-methoxyphenyl)-methylamino]-methylene}-thiazolidin-4-one.

The following compound exhibited agonist activity at less than 100 nM with greater than 100% efficacy as measured via the co-transfection assay:

2-(5-acetyl-2-ethylamino-phenylimino)-3-benzyl-5-(2,3-dihydroindol-1-ylmethylene)-thiazolidin-4-one;

The following compound exhibited apparent partial agonist activity with $EC_{50}$ at about 1 μM and $IC_{50}$ at about 300-500 nM with 40-50% efficacy and about 60% efficacy as measured via the one or more of the in vitro assays described herein:

2-(5-acetyl-2-ethylamino-phenylimino)-3-benzyl-5-[(N-benzyl-methylamino)-methylene]-thiazolidin-4-one; and 3-(3-benzyl-5-{[N-(4-methoxyphenyl)-methylamino]-methylene}-4-oxothiazolidin-2-ylideneamino)-4-ethylamino-benzonitrile.

Since modifications will be apparent to those of skill in this art, it is intended that this invention be limited only by the scope of the appended claims.

TABLE 1

| No. | STRUCTURE | CHEMICAL NAME |
|---|---|---|
| 1 | 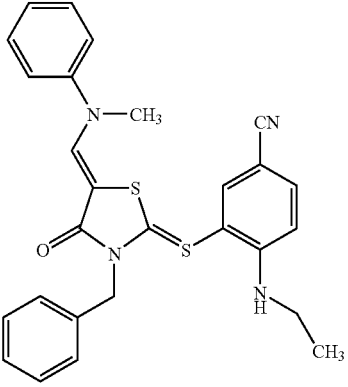 | 4-(ethylamino)-3-{[(2Z,5Z)-5-{[methyl(phenyl)amino]methylidene}-4-oxo-3-(phenylmethyl)-1,3-thiazolidin-2-ylidene]amino}benzonitrile |
| 2 | 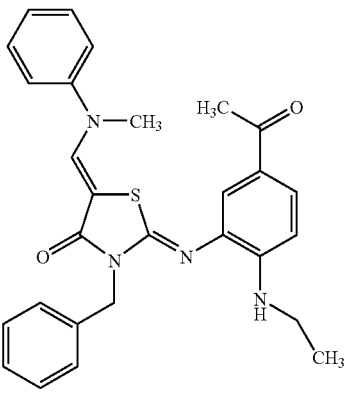 | (2Z,5Z)-2-{[5-acetyl-2-(ethylamino)phenyl]imino}-5-{[methyl(phenyl)amino]methylidene}-3-(phenylmethyl)-1,3-thiazolidin-4-one |
| 3 | 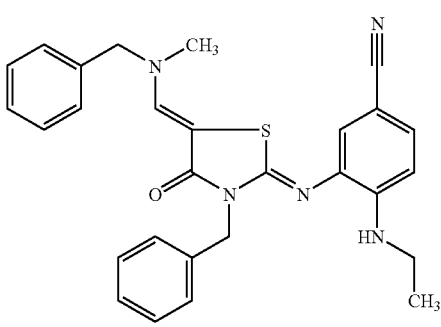 | 4-(ethylamino)-3-{[(2Z,5Z)-5-{[methyl(phenylmethyl)amino]methylidene}-4-oxo-3-(phenylmethyl)-1,3-thiazolidin-2-ylidene]amino}benzonitrile |

| No. | STRUCTURE | CHEMICAL NAME |
|---|---|---|
| 4 | 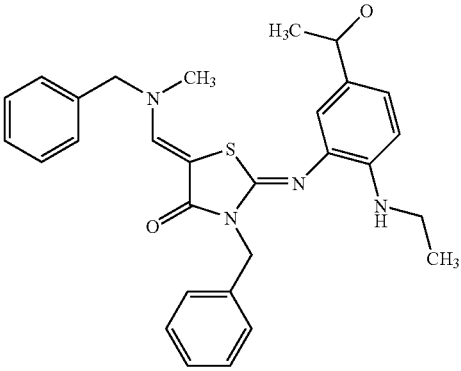 | (2Z,5Z)-2-{[5-acetyl-2-(ethylamino)phenyl]imino}-5-{[methyl(phenylmethyl)amino]methylidene}-3-(phenylmethyl)-1,3-thiazolidin-4-one |
| 5 | 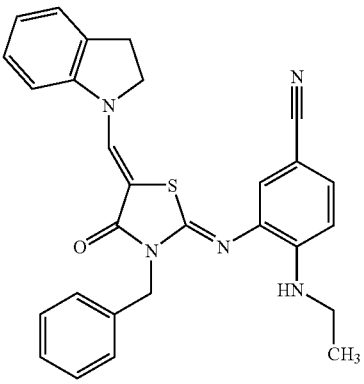 | 3-{[(2Z,5Z)-5-(2,3-dihydro-1H-indol-1-ylmethylidene)-4-oxo-3-(phenylmethyl)-1,3-thiazolidin-2-ylidene]amino}-4-(ethylamino)benzonitrile |
| 6 | 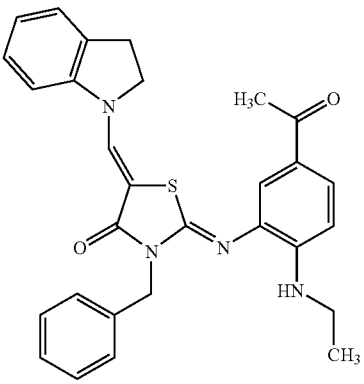 | (2Z,5Z)-2-{[5-acetyl-2-(ethylamino)phenyl]imino}-5-(2,3-dihydro-1H-indol-1-ylmethylidene)-3-(phenylmethyl)-1,3-thiazolidin-4-one |

TABLE 1-continued

| No. | STRUCTURE | CHEMICAL NAME |
|---|---|---|
| 7 | 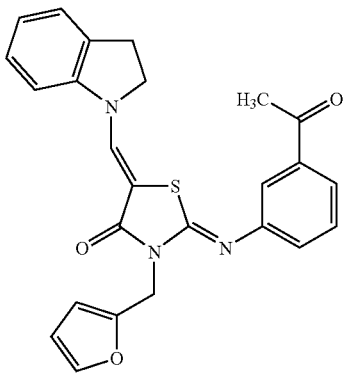 | (2Z,5Z)-2-[(3-acetylphenyl)imino]-5-(2,3-dihydro-1H-indol-1-ylmethylidene)-3-(furan-2-ylmethyl)-1,3-thiazolidin-4-one |
| 8 | 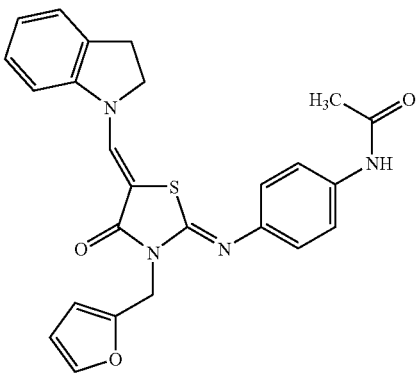 | N-(4-{[(2Z,5Z)-5-(2,3-dihydro-1H-indol-1-ylmethylidene)-3-(furan-2-ylmethyl)-4-oxo-1,3-thiazolidin-2-ylidene]amino}phenyl)acetamide |
| 9 | 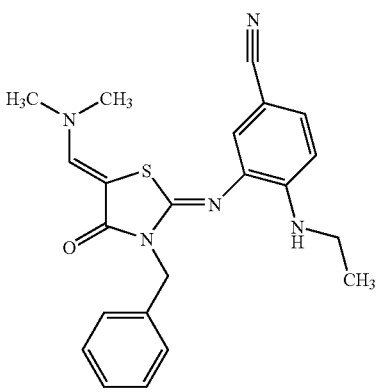 | 3-{[(2Z,5Z)-5-[(dimethylamino)methylidene]-4-oxo-3-(phenylmethyl)-1,3-thiazolidin-2-ylidene]amino}-4-(ethylamino)benzonitrile |
| 10 | 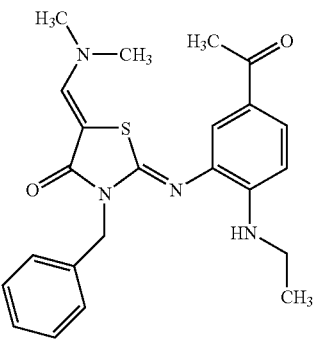 | (2Z,5Z)-2-{[5-acetyl-2-(ethylamino)phenyl]imino}-5-[(dimethylamino)methylidene]-3-(phenylmethyl)-1,3-thiazolidin-4-one |

TABLE 1-continued

| No. | STRUCTURE | CHEMICAL NAME |
|---|---|---|
| 11 | 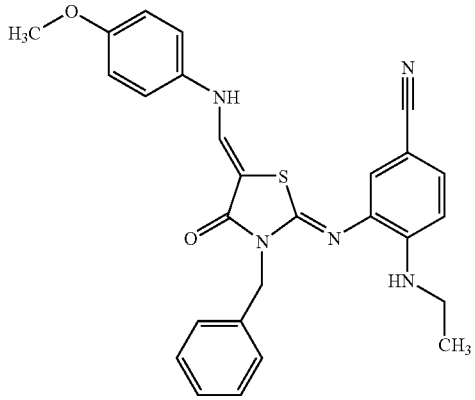 | 4-(ethylamino)-3-{[(2Z,5Z)-5-({[4-(methyloxy)phenyl]amino}methylidene)-4-oxo-3-(phenylmethyl)-1,3-thiazolidin-2-ylidene]amino}benzonitrile |
| 12 | 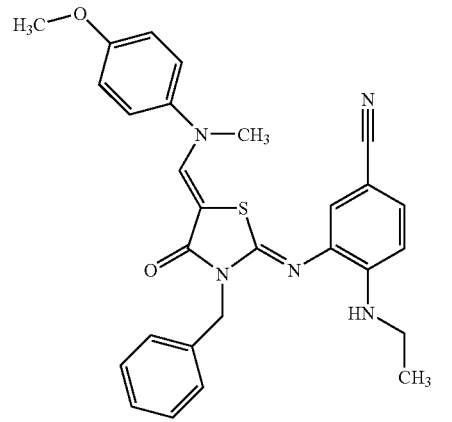 | 4-(ethylamino)-3-{[(2Z,5Z)-5-({methyl[4-(methyloxy)phenyl]amino}methylidene)-4-oxo-3-(phenylmethyl)-1,3-thiazolidin-2-ylidene]amino}benzonitrile |
| 13 | 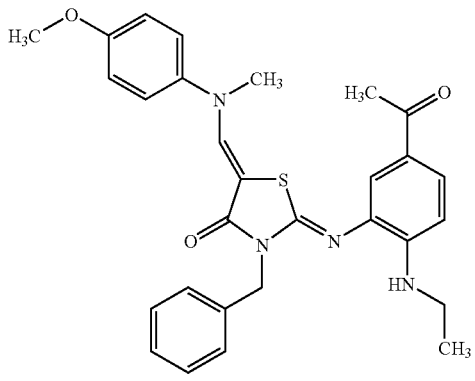 | (2Z,5Z)-2-{[5-acetyl-2-(ethylamino)phenyl]imino}-5-({methyl[4-(methyloxy)phenyl]amino}-methylidene)-3-(phenylmethyl)-1,3-thiazolidin-4-one |
| 14 | 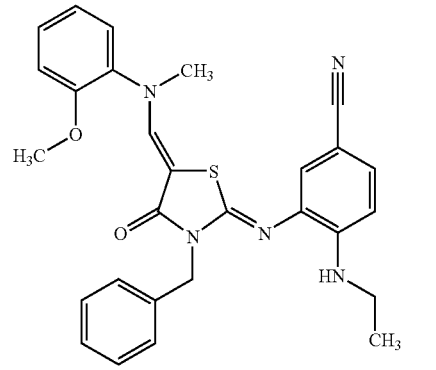 | 4-(ethylamino)-3-{[(2Z,5Z)-5-({methyl[2-(methyloxy)phenyl]amino}methylidene)-4-oxo-3-(phenylmethyl)-1,3-thiazolidin-2-ylidene]amino}benzonitrile |

TABLE 1-continued

| No. | STRUCTURE | CHEMICAL NAME |
|---|---|---|
| 15 | 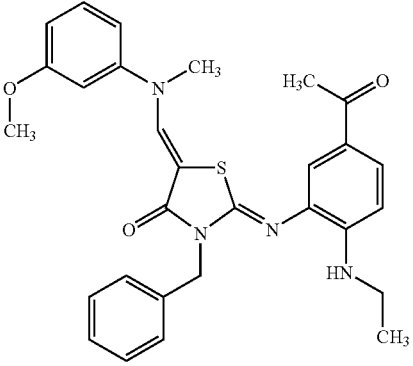 | (2Z,5Z)-2-{[5-acetyl-2-(ethylamino)phenyl]imino}-5-({methyl[3-(methyloxy)phenyl]amino}methylidene)-3-(phenylmethyl)-1,3-thiazolidin-4-one |
| 16 | 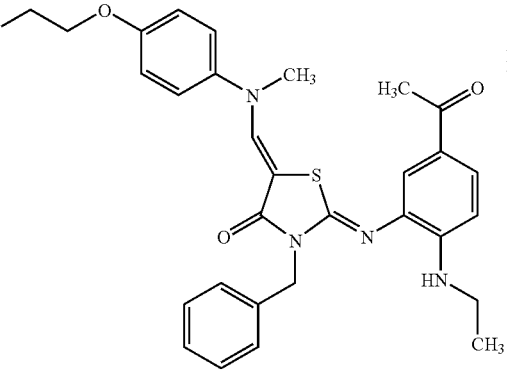 | (2Z,5Z)-2-{[5-acetyl-2-(ethylamino)phenyl]imino}-5-{[methyl(4-{[2-(methyloxy)ethyl]oxy}phenyl)amino]methylidene}-3-(phenylmethyl)-1,3-thiazolidin-4-one |
| 17 | 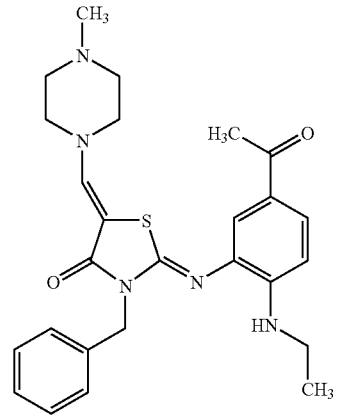 | (2Z,5Z)-2-{[5-acetyl-2-(ethylamino)phenyl]imino}-5-[(4-methylpiperazin-1-yl)methylidene]-3-(phenylmethyl)-1,3-thiazolidin-4-one |
| 18 | 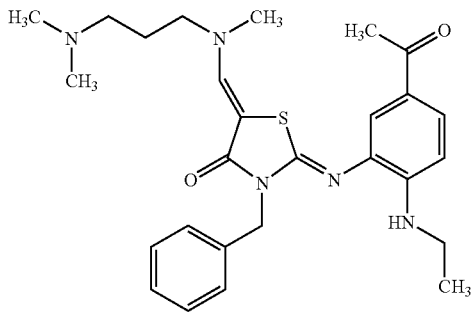 | (2Z,5Z)-2-{[5-acetyl-2-(ethylamino)phenyl]imino}-5-({[3-(dimethylamino)propyl](methyl)amino}methylidene)-3-(phenylmethyl)-1,3-thiazolidin-4-one |

TABLE 1-continued

| No. | STRUCTURE | CHEMICAL NAME |
|---|---|---|
| 19 | 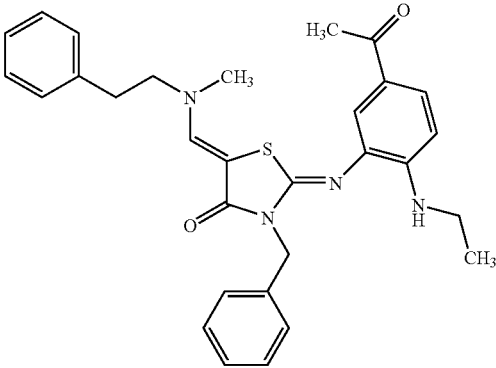 | (2Z,5Z)-2-{[5-acetyl-2-(ethylamino)phenyl]imino}-5-{[methyl(2-phenylethyl)amino]methylidene}-3-(phenylmethyl)-1,3-thiazolidin-4-one |
| 20 | 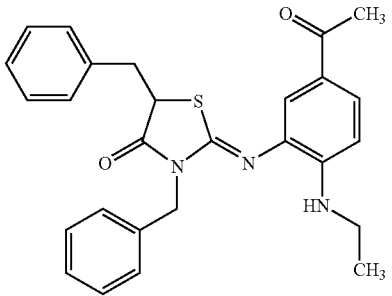 | (2Z)-2-{[5-acetyl-2-(ethylamino)phenyl]imino}-3,5-bis(phenylmethyl)-1,3-thiazolidin-4-one |
| 21 | 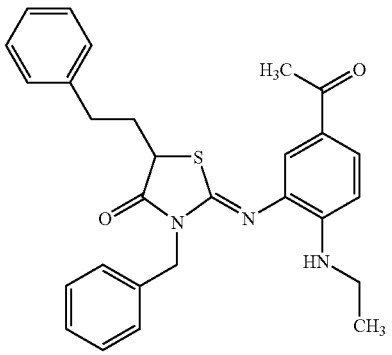 | (2Z)-2-{[5-acetyl-2-(ethylamino)phenyl]imino}-5-(2-phenylethyl)-3-(phenylmethyl)-1,3-thiazolidin-4-one |
| 22 | 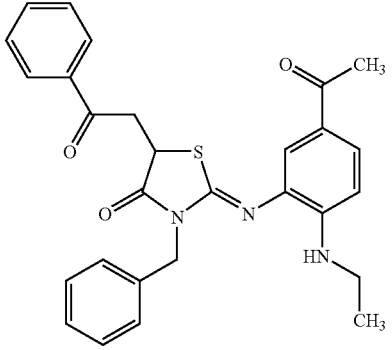 | (2Z)-2-{[5-acetyl-2-(ethylamino)phenyl]imino}-5-(2-oxo-2-phenylethyl)-3-(phenylmethyl)-1,3-thiazolidin-4-one |

TABLE 1-continued

| No. | STRUCTURE | CHEMICAL NAME |
|---|---|---|
| 23 | 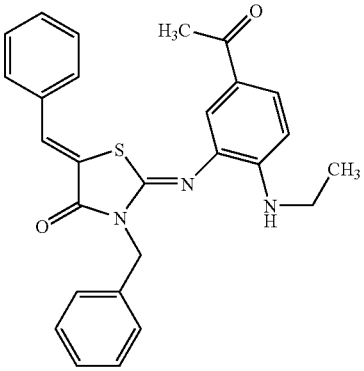 | (2Z,5Z)-2-{[5-acetyl-2-ethylamino)phenyl]imino}-3-(phenylmethyl)-5-(phenylmethylidene)-1,3-thiazolidin-4-one |
| 24 | 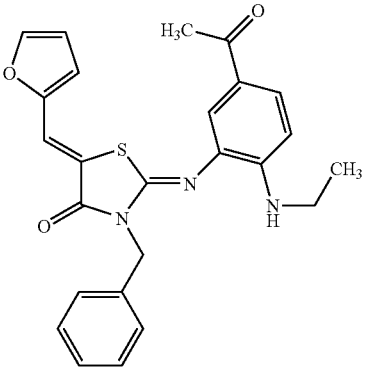 | (2Z,5Z)-2-{[5-acetyl-2-(ethylamino)phenyl]imino}-5-(furan-2-ylmethylidene)-3-(phenylmethyl)-1,3-thiazolidin-4-one |

What is claimed is:

1. A compound having the formula (I):

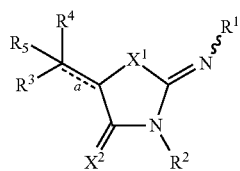

or a pharmaceutically acceptable derivative thereof, wherein:
bond a is a single bond or double bond;
$X^1$ is $NR^6$, O or $S(O)_r$;
$X^2$ is S or O;
$R^1$ is optionally substituted alkyl, optionally substituted alkenyl or optionally substituted alkynyl, all or which, when substituted, are substituted with one to five substituents each independently selected from the group consisting of cyano, nitro, halo, pseudohalo, —$OR^{10}$, —$SR^{16}$, —$N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$, —$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, —$Si(R^{14})_3$, —$N(R^{10})S(O)_rR^{15}$ and —$R^9$—$S(O)_rR^{15}$;

or $R^1$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_rR^{15}$ and —$R^9$—$S(O)_rR^{15}$;

or $R^1$ is —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$N(R^{10})C(J)R^{13}$, —$R^9$—$N(R^{10})C(J)OR^{10}$, —$R^9$—$S(O)_rR^{15}$ or —$R^9$—$N(R^{10})C(J)N(R^{11})(R^{12})$;

$R^2$ is optionally substituted alkyl, optionally substituted alkenyl, optionally substituted alkynyl, all or which, when substituted, are substituted with one to five substituents each independently selected from the group consisting of cyano, nitro, halo, pseudohalo, —$OR^{10}$, —$SR^{16}$, —$N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$, —$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, —$Si(R^{14})_3$, —$N(R^{10})S(O)_rR^{15}$ and —$S(O)_rR^{15}$;

or $R^2$ is optionally substituted cycloalkyl, optionally substituted cycloalkylalkyl, optionally substituted heterocyclyl, optionally substituted heterocyclylalkyl, optionally substituted aryl, optionally substituted heteroaryl, optionally substituted aralkyl, optionally substituted heteroaralkyl or optionally substituted aryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})$, $-R^9-C(J)N(R^{10})N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-R^9-S(O)_tR^{15}$;

or $R^2$ is $-R^9-C(J)R^{13}$, $-R^9-C(J)OR^{10}$, $-R^9-C(J)N(R^{11})(R^{12})$, $-R^9-C(J)N(R^{10})N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-N(R^{11})(R^{12})$ or $-R^9-S(O)_tR^{15}$;

$R^3$, $R^4$ and $R^5$ are each independently selected as in (a), (b) or (c) as follows:

(a) $R^3$, $R^4$ and $R^5$ are each independently optionally substituted alkyl, optionally substituted alkenyl or optionally substituted alkynyl, all of which, when substituted are substituted with cyano, nitro, halo, pseudohalo, $-OR^{10}$, $-SR^{16}$, $-N(R^{11})(R^{12})$, $-C(J)R^{13}$, $-C(J)OR^{10}$, $-C(J)N(R^{11})(R^{12})$, $-C(J)N(R^{10})N(R^{11})(R^{12})$, $-N(R^{10})C(J)R^{13}$, $-N(R^{10})C(J)OR^{10}$, $-N(R^{10})C(J)N(R^{11})(R^{12})$, $-OC(J)R^{13}$, $-OC(J)OR^{10}$, $-OC(J)N(R^{11})(R^{12})$, $-Si(R^{14})_3$, $-N(R^{10})S(O)_tR^{15}$ and $-S(O)_tR^{15}$;

or (b) $R^3$, $R^4$ and $R^5$ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)N(R^{11})(R^{12})$, $-Si(R^{14})_3$, $-N(R^{10})S(O)_tR^{15}$ and $-R^9-S(O)_tR^{15}$;

or (c) $R^3$, $R^4$ and $R^5$ are each independently selected from a group consisting of hydrogen, halo, $-N(R^7)(R^8)$, $-N(R^{10})C(J)R^{13}$, $-N(R^{10})C(J)OR^{10}$, $-R^9-C(J)R^{13}$, $-N(R^{10})C(J)N(R^{11})(R^{12})$ and $-N(R^{10})S(O)_tR^{15}$;

provided that $R^5$ is present only when bond a is a single bond;

and further provided that:

when $R^3$, $R^4$ or $R^5$ is cycloalkylalkyl or $-N(R^7)(R^8)$ and bond a is a single bond, then $R^1$ is phenyl substituted with at least two different substituents selected from the following: cyano, $-R^9-C(J)R^{13}$, $-R^9-C(J)N(R^{11})(R^{12})$, $-R^9-C(J)N(R^{10})N(R^{12})R^{13}$, $-R^9-N(R^{10})C(J)OR^{10}$, $-R^9-N(R^{10})C(J)N(R^{11})(R^{12})$, $-N(R^{10})S(O)_tR^{13}$, $-R^9-N(R^{10})C(J)R^{13}$, and $-R^9-N(R^{11})(R^{12})$;

or when $R^3$, $R^4$ or $R^5$ is alkyl, alkenyl, alkynyl, halo, haloalkyl, cycloalkyl, heterycyclylalkyl, aralkyl, $-R^9-C(J)R^{13}$, $-R^9-C(J)OR^{10}$, $-R^9-S(O)_tR^{15}$, aryl or heteroaryl, then $R^1$ is phenyl substituted with at least two different substituents selected from the following: cyano, $-R^9-C(J)R^{13}$, $-R^9-C(J)N(R^{11})(R^{12})$, $-R^9-C(J)N(R^{10})N(R^{12})R^{13}$, $-R^9-N(R^{10})C(J)OR^{10}$, $-R^9-N(R^{10})C(J)N(R^{11})(R^{12})$, $-N(R^{10})S(O)_tR^{13}$, $-R^9-N(R^{10})C(J)R^{13}$, and $-R^9-N(R^{11})(R^{12})$;

and further provided that $R^3$, $R^4$ and $R^5$ are not all hydrogen;

$R^6$ is hydrogen, alkyl, alkenyl, alkynyl, aryl, heteroaryl, cycloalkyl, heterocyclyl, aralkyl, heteroaralkyl, $-R^9-S(O)_tR^{15}$, $-R^9-C(J)R^{13}$, $-R^9-C(J)OR^{10}$ or $-R^9-C(J)N(R^{11})(R^{12})$;

$R^7$ and $R^8$ each independently selected as in (a), (b) or (c) as follows:

(a) $R^7$ and $R^8$ are each independently optionally substituted alkyl, optionally substituted alkenyl or optionally substituted alkynyl, all of which, when substituted, are substituted with one to three substituents each independently selected from the group consisting of cyano, nitro, halo, pseudohalo, $-OR^{10}$, $-SR^{16}$, $-N(R^{11})(R^{12})$, $-OR^{16}OR^{10}$, $-C(J)R^{13}$, $-C(J)OR^{10}$, $-C(J)N(R^{11})(R^{12})$, $-C(J)N(R^{10})N(R^{11})(R^{12})$, $-N(R^{11})(R^{12})$, $-N(R^{10})C(J)R^{13}$, $-N(R^{10})C(J)OR^{10}$, $-N(R^{10})C(J)N(R^{11})(R^{12})$, $-OC(J)R^{13}$, $-OC(J)OR^{10}$, $-OC(J)N(R^{11})(R^{12})$, $-Si(R^{14})_3$, $-N(R^{10})S(O)_tR^{15}$ and $-S(O)_tR^{15}$;

or (b) $R^7$ and $R^8$ are are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-OR^{16}OR^{16}OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-C(J)N(R^{10})N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-R^9-S(O)_tR^{15}$;

or (c) $R^7$ and $R^8$ are each independently hydrogen, $-C(J)R^{13}$, $-C(J)OR^{10}$, $-C(J)N(R^{11})(R^{12})$, $-N(R^{10})C(J)OR^{10}$ or $-S(O)_tR^{15}$ provided, however, that both $R^7$ and $R^8$ cannot be hydrogen;

or $R^7$ and $R^8$ together with the nitrogen atom to which they are attached, form an optionally substituted heterocyclyl or an optionally substituted heteroaryl, either of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, $-R^9-OR^{10}$, $-R^9-OR^{16}OR^{10}$, $-R^9-SR^{16}$, $-R^9-N(R^{11})(R^{12})$, $-R^9-C(J)R^{13}$, $-R^9-C(J)OR^{10}$, $-R^9-C(J)N(R^{11})(R^{12})$, $-R^9-C(J)N(R^{10})N(R^{12})$, $-R^9-N(R^{10})C(J)R^{13}$, $-R^9-N(R^{10})C(J)OR^{10}$, $-R^9-N(R^{10})C(J)N(R^{11})(R^{12})$, $-R^9-OC(J)R^{13}$, $-R^9-OC(J)OR^{10}$, $-R^9-OC(J)N(R^{11})(R^{12})$, $-Si(R^{14})_3$, $-N(R^{10})S(O)_tR^{15}$ and $-S(O)_tR^{15}$;

each $R^9$ is independently a direct bond or a straight or branched alkylene chain;

$R^{10}$ and $R^{13}$ are each independently hydrogen, alkyl, alkenyl, alkynyl, haloalkyl, cycloalkyl, cycloalkylalkyl, heterocyclyl, heterocyclylalkyl, aryl, aralkyl, heteroaryl or heteroaralkyl;

$R^{11}$ and $R^{12}$ are each independently hydrogen, alkyl, alkenyl, alkynyl, haloalkyl, cycloalkyl, cycloalkylalkyl, heterocyclyl, heterocyclylalkyl, aryl, aralkyl, heteroaryl or heteroaralkyl;

or $R^{11}$ and $R^{12}$ together with the nitrogen atom to which they are attached, form a heterocyclyl, heterocyclylalkenyl, or heteroaryl;

$R^{14}$ $R^{15}$ and $R^{16}$ are each independently alkyl, alkenyl, alkynyl, haloalkyl, cycloalkyl, cycloalkylalkyl, heterocyclyl, heterocyclylalkyl, aryl, aralkyl, heteroaryl or heteroaralkyl;

each J is independently O or S; and each t is independently 0 to 2.

2. A compound of claim 1 having the formula (II):

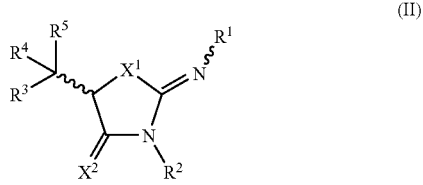

(II)

or a pharmaceutically acceptable derivative thereof, wherein side a is a single bond and wherein $R^1$-$R^5$, $X^1$ and $X^2$ are as defined in claim 1.

3. A compound of claim 2 wherein:

$X^1$ is S;

$X^2$ is O; and $R^3$, $R^4$ and $R^5$ are each independently selected as in (a) or (c) as follows:

(a) $R^3$, $R^4$ and $R^5$ are each independently optionally substituted alkyl, optionally substituted alkenyl or optionally substituted alkynyl, all of which, when substituted are substituted with cyano, nitro, halo, pseudohalo, —$OR^{10}$, —$SR^{16}$, —$N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$, —$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, —$Si(R^{14})_3$, —$N(R^{10})S(O)_tR^{15}$ and —$S(O)_tR^{15}$;

or (c) $R^3$, $R^4$ and $R^5$ are each independently selected from a group consisting of hydrogen, halo, —$N(R^7)(R^8)$, —$N(R^{10})C(J)R^{13}$, —$N(R^{10})C(J)OR^{10}$, —$R^9$—$C(J)R^{13}$, —$N(R^{10})C(J)N(R^{11})(R^{12})$ and —$N(R^{10})S(O)_tR^{15}$.

4. A compound of claim 3 wherein:

$R^1$ is optionally substituted cycloalkyl, optionally substituted heterocyclyl, optionally substituted aryl or optionally substituted heteroaryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$; and $R^2$ is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$ and —$R^9$—$N(R^{11})(R^{12})$.

5. A compound of claim 2 wherein:

$X^1$ is S;

$X^2$ is O;

$R^1$ is optionally substituted alkyl, optionally substituted with one to five substituents each independently selected from the group consisting of cyano, nitro, halo, pseudohalo, —$OR^{10}$, —$SR^{16}$, and —$N(R^{11})(R^{12})$;

or $R^1$ is optionally substituted cycloalkyl, optionally substituted heterocyclyl, optionally substituted aryl or optionally substituted heteroaryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$;

$R^2$ is optionally substituted alkyl or optionally substituted alkenyl, optionally substituted with one to five substituents each independently selected from the group consisting of cyano, nitro, halo, pseudohalo, —$OR^{10}$, —$SR^{16}$ and —$N(R^{11})(R^{12})$, or $R^2$ is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$ and —$R^9$—$N(R^{11})(R^{12})$;

$R^3$, $R^4$ and $R^5$ are each independently selected as in (a), (b) or (c) as follows:

(a) $R^3$, $R^4$ and $R^5$ are each independently optionally substituted alkyl or optionally substituted alkenyl, either of which, when substituted is substituted with cyano, nitro, halo, pseudohalo, —$OR^{10}$, —$SR^{16}$, —$N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$, —$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, —$Si(R^{14})_3$, —$N(R^{10})S(O)_tR^{15}$ and —$S(O)_tR^{15}$;

(b) $R^3$, $R^4$ and $R^5$ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$;

or (c) $R^3$, $R^4$ and $R^5$ are each independently hydrogen or —$R^9$—$C(J)R^{13}$.

6. A compound of claim 5 wherein:

$R^1$ is optionally substituted cycloalkyl, optionally substituted heterocyclyl, optionally substituted aryl or optionally substituted heteroaryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})R^{12})$, —$Si(R^{14})_3$, —$N(R^{10})S(O)_tR^{15}$ and —$R^9$—$S(O)_tR^{15}$; and $R^2$ is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$ and —$R^9$—$N(R^{11})(R^{12})$.

7. A compound of claim 6 wherein the compound is
2-(5-acetyl-2-ethylamino-phenylimino)-3-benzyl-5-(2-oxo-2-phenylethyl)-thiazolidin-4-one;
2-(5-acetyl-2-ethylamino-phenylimino)-3,5-dibenzyl-thiazolidin-4-one; and
2-(5-acetyl-2-ethylamino-phenylimino)-3-benzyl-5-phenethyl-thiazolidin-4-one.

8. A compound of claim 1 having the formula (III)

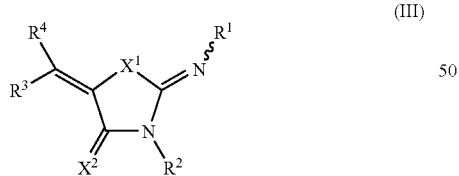

(III)

or a pharmaceutically acceptable derivative thereof, wherein bond a is a double bond.

9. A compound of claim 8 wherein:

$X^1$ is S;

$X^2$ is O;

$R^1$ is optionally substituted alkyl, optionally substituted with one to five substituents each independently selected from the group consisting of cyano, nitro, halo, pseudohalo, —$OR^{10}$, —$SR^{16}$, and —$N(R^{11})(R^{12})$;

or $R^1$ is optionally substituted cycloalkyl, optionally substituted heterocyclyl, optionally substituted aryl or optionally substituted heteroaryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$;

$R^2$ is optionally substituted alkyl or optionally substituted alkenyl, optionally substituted with one to five substituents each independently selected from the group consisting of cyano, nitro, halo, pseudohalo, —$OR^{10}$, —$SR^{16}$ and —$N(R^{11})(R^{12})$, or $R^2$ is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$ and —$R^9$—$N(R^{11})(R^{12})$;

$R^3$ and $R^4$ are each independently selected as in (a), (b) or (c) as follows:

(a) $R^3$ and $R^4$ are each independently optionally substituted alkyl, optionally substituted alkenyl or optionally substituted alkynyl, all of which, when substituted are substituted with cyano, nitro, halo, pseudohalo, —$OR^{10}$, —$SR^{16}$, —$N(R^{11})(R^{12})$, —$C(J)R^{13}$, —$C(J)OR^{10}$, —$C(J)N(R^{11})(R^{12})$, —$C(J)N(R^{10})N(R^{11})(R^{12})$, —$N(R^{10})C(J)R^{13}$, —$N(R^{10})C(J)OR^{10}$, —$N(R^{10})C(J)N(R^{11})(R^{12})$, —$OC(J)R^{13}$, —$OC(J)OR^{10}$, —$OC(J)N(R^{11})(R^{12})$, —$Si(R^{14})_3$, —$N(R^{10})S(O)_tR^{15}$ and —$S(O)_tR^{15}$;

(b) $R^3$ and $R^4$ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$;

or (c) $R^3$ and $R^4$ are each independently hydrogen or —$R^9$—$C(J)R^{13}$;

provided that when $R^3$ or $R^4$ is alkyl, alkenyl, alkynyl, halo, haloalkyl, cycloalkyl, —$R^9$—$C(J)R^{13}$, aryl or heteroaryl, then $R^1$ is phenyl and $R^1$ is substituted with at least two different substituents selected from the following: cyano, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{12})R^{13}$, —$R^9$—$N(R^{10})C(J)OR^{10}$, —$R^9$—$N(R^{10})C(J)N(R^{11})(R^{12})$, —$N(R^{10})S(O)_tR^{13}$, —$R^9$—$N(R^{10})C(J)R^{13}$, and —$R^9$—$N(R^{11})(R^{12})$;

and further provided, however, that both R³ and R⁴ cannot be hydrogen.

10. The compound of claim 9 selected from the group consisting of the following:
2-(5-acetyl-2-ethylamino-phenylimino)-3-benzyl-5-benzylidene-thiazolidin-4-one; and
2-(5-acetyl-2-ethylamino-phenylimino)-3-benzyl-5-furan-2-ylmethylene-thiazolidin-4-one.

11. A compound of claim 9 having the formula (IVa or IVb):

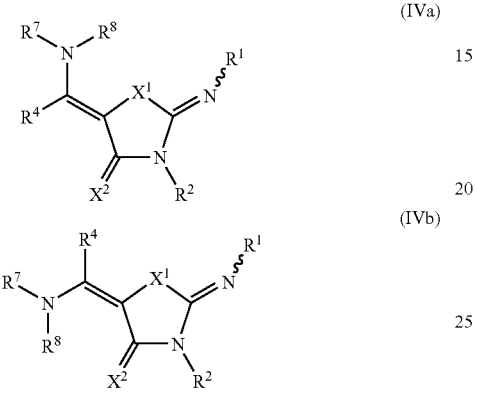

or a pharmaceutically acceptable derivative thereof.

12. A compound of claim 11 wherein:
R⁷ and R⁸ are selected as in (a), (b) or (c) as follows:
(a) R⁷ and R⁸ are each independently optionally substituted alkyl, optionally substituted alkenyl or optionally substituted alkynyl, optionally substituted with cyano, nitro, halo, pseudohalo, —OR¹⁰, —SR¹⁶, —N(R¹¹)(R¹²), —OR¹⁶OR¹⁰, —C(J)R¹³, —C(J)OR¹⁰, —C(J)N(R¹¹)(R¹²), —C(J)N(R¹⁰)N(R¹¹)(R¹²), —N(R¹⁰)C(J)R¹³, —N(R¹⁰)C(J)OR¹⁰, —N(R¹⁰)C(J)N(R¹¹)(R¹²), —OC(J)R¹³, —OC(J)OR¹⁰, —OC(J)N(R¹¹)(R¹²), —Si(R¹⁴)₃, —N(R¹⁰)S(O)ᵣR¹⁵ and —S(O)ᵣR¹⁵;
or (b) R⁷ and R⁸ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R⁹—OR¹⁰, —R⁹—OR¹⁶OR¹⁰, —R⁹—SR¹⁶, —R⁹—N(R¹¹)(R¹²), —R⁹—C(J)R¹³, —R⁹—C(J)OR¹⁰, —R⁹—C(J)N(R¹¹)(R¹²), —R⁹—N(R¹⁰)C(J)R¹³, —R⁹—N(R¹⁰)C(J)OR¹⁰, —R⁹—N(R¹⁰)C(J)N(R¹¹)(R¹²), —R⁹—C(J)N(R¹⁰)N(R¹¹)(R¹²), —R⁹—OC(J)R¹³, —R⁹—OC(J)OR¹⁰, —R⁹—OC(J)N(R¹¹)(R¹²), —Si(R¹⁴)₃, —N(R¹⁰)S(O)ᵣR¹⁵ and —R⁹—S(O)ᵣR¹⁵;
or (c) one of R⁷ and R⁸ is hydrogen and the other of R⁷ and R⁸ is selected as in (a) or (b) above;
or R⁷ and R⁸ together with the nitrogen atom to which they are attached, form an optionally substituted heterocyclyl or an optionally substituted heteroaryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R⁹—OR¹⁰, —R⁹—OR¹⁶OR¹⁰, —R⁹—SR¹⁶, —R⁹—N(R¹¹)(R¹²), —R⁹—C(J)R¹³, —R⁹—C(J)OR¹⁰, —R⁹—C(J)N(R¹¹)(R¹²), —R⁹—C(J)N(R¹⁰)N(R¹¹)(R¹²), —R⁹—N(R¹⁰)C(J)R¹³, —R⁹—N(R¹⁰)C(J)OR¹⁰, —R⁹—N(R¹⁰)C(J)N(R¹¹)(R¹²), —R⁹—OC(J)R¹³, —R⁹—OC(J)OR¹⁰, —R⁹—OC(J)N(R¹¹)(R¹²), —Si(R¹⁴)₃, —N(R¹⁰)S(O)ᵣR¹⁵ and —S(O)ᵣR¹⁵.

13. A compound of claim 12 wherein:
X¹ is S;
X² is O;
R¹ is optionally substituted alkyl or optionally substituted alkenyl, optionally substituted with one to five substituents each independently selected from the group consisting of cyano, nitro, halo, pseudohalo, —OR¹⁰, —SR¹⁶ and —N(R¹¹)(R¹²),
or R¹ is optionally substituted cycloalkyl, optionally substituted heterocyclyl, optionally substituted aryl or optionally substituted heteroaryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R⁹—OR¹⁰, —R⁹—SR¹⁶, —R⁹—N(R¹¹)(R¹²), —R⁹—C(J)R¹³, —R⁹—C(J)OR¹⁰, —R⁹—C(J)N(R¹¹)(R¹²), —R⁹—C(J)N(R¹⁰)N(R¹¹)(R¹²), —R⁹—N(R¹⁰)C(J)R¹³, —R⁹—N(R¹⁰)C(J)OR¹⁰, —R⁹—N(R¹⁰)C(J)N(R¹¹)(R¹²), —R⁹—OC(J)R¹³, —R⁹—OC(J)OR¹⁰, —R⁹—OC(J)N(R¹¹)(R¹²), —Si(R¹⁴)₃, —N(R¹⁰)S(O)ᵣR¹⁵ and —R⁹—S(O)ᵣR¹⁵;
R² is optionally substituted alkyl or optionally substituted alkenyl, optionally substituted with one to five substituents each independently selected from the group consisting of cyano, nitro, halo, pseudohalo, —OR¹⁰, —SR¹⁶ and —N(R¹¹)(R¹²),
or R² is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R⁹—OR¹⁰, —R⁹—SR¹⁶, —R⁹—N(R¹¹)(R¹²);
R⁴ is hydrogen or alkyl;
R⁷ and R⁸ together with the nitrogen atom to which they are attached, form an optionally substituted heterocyclyl or an optionally substituted heteroaryl optionally substituted with cyano, nitro, halo, pseudohalo, —OR¹⁰, —SR¹⁶ or —N(R¹¹)(R¹²).

14. The compound of claim 13 wherein:
R¹ is optionally substituted cycloalkyl, optionally substituted heterocyclyl, optionally substituted aryl or optionally substituted heteroaryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R⁹—OR¹⁰, —R⁹—SR¹⁶, —R⁹—N(R¹¹)(R¹²), —R⁹—C(J)R¹³, —R⁹—C(J)OR¹⁰, —R⁹—C(J)N(R¹¹)(R¹²), —R⁹—C(J)N(R¹⁰)N(R¹¹)(R¹²), —R⁹—N(R¹⁰)C(J)R¹³, —R⁹—N(R¹⁰)C(J)OR¹⁰, —R⁹—N(R¹⁰)C(J)N $(R^{11})(R^{12})$, —$R^9$—OC(J)$R^{13}$, —$R^9$—OC(J)O$R^{10}$, —$R^9$—OC(J)N($R^{11}$)($R^{12}$), —Si($R^{14}$)$_3$, —N($R^{10}$)S(O)$_t$$R^{15}$ and —$R^9$—S(O)$_t$$R^{15}$;

$R^2$ is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—O$R^{10}$, —$R^9$—S$R^{16}$ and —$R^9$—N($R^{11}$)($R^{12}$).

15. The compound of claim 14 selected from the group consisting of the following:
- 3-[3-benzyl-5-(2,3-dihydroindol-1-ylmethylene)-4-oxothiazolidin-2-ylideneamino]-4-ethylamino-benzonitrile;
- 2-(5-acetyl-2-ethylamino-phenylimino)-3-benzyl-5-(2,3-dihydroindol-1-ylmethylene)-thiazolidin-4-one;
- 2-(3-acetylphenylimino)-5-(2,3-dihydroindol-1-ylmethylene)-3-furan-2-ylmethyl-thiazolidin-4-one;
- N-{4-[5-(2,3-dihydroindol-1-ylmethylene)-3-furan-2-ylmethyl-4-oxothiazolidin-2-ylideneamino]-phenyl}-acetamide; and
- 2-(5-acetyl-2-ethylamino-phenylimino)-3-benzyl-5-(4-methylpiperazin-1-ylmethylene)-thiazolidin-4-one.

16. A compound of claim 11 or claim 12 wherein:
$R^7$ and $R^8$ each independently selected as in (a), (b) or (c) as follows:
(a) $R^7$ and $R^8$ are each independently optionally substituted alkyl, optionally substituted with cyano, nitro, halo, pseudohalo, —O$R^{10}$, —S$R^{16}$ or —N($R^{11}$)($R^{12}$);
or (b) $R^7$ and $R^8$ are each independently optionally substituted aryl, optionally substituted aralkyl, optionally substituted heteroaryl or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—O$R^{10}$, —$R^9$—O$R^{16}$O$R^{10}$, —$R^9$—S$R^{16}$ and —$R^9$—N($R^{11}$)($R^{12}$);
or (c) one of $R^7$ and $R^8$ is hydrogen and the other of $R^7$ and $R^8$ is selected as in (a) or (b) above.

17. The compound of claim 16, wherein:
$R^1$ is optionally substituted cycloalkyl, optionally substituted heterocyclyl, optionally substituted aryl or optionally substituted heteroaryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—O$R^{10}$, —$R^9$—S$R^{16}$, —$R^9$—N($R^{11}$)($R^{12}$), —$R^9$—C(J)$R^{13}$, —$R^9$—C(J)O$R^{10}$, —$R^9$—C(J)N($R^{11}$)($R^{12}$), —$R^9$—C(J)N($R^{10}$)N($R^{11}$)($R^{12}$), —$R^9$—N($R^{10}$)C(J)$R^{13}$, —$R^9$—N($R^{10}$)C(J)O$R^{10}$, —$R^9$—N($R^{10}$)C(J)N($R^{11}$)($R^{12}$), —$R^9$—OC(J)$R^{13}$, —$R^9$—OC(J)O$R^{10}$, —$R^9$—OC(J)N($R^{11}$)($R^{12}$), —Si($R^{14}$)$_3$, —N($R^{10}$)S(O)$_t$$R^{15}$ and —$R^9$—S(O)$_t$$R^{15}$; and $R^2$ is optionally substituted cycloalkyl, optionally substituted cycloalkylalkyl, optionally substituted heterocyclyl, optionally substituted heterocyclylalkyl, optionally substituted aralkyl or optionally substituted heteroaralkyl, optionally substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—O$R^{10}$, —$R^9$—S$R^{16}$ and —$R^9$—N($R^{11}$)($R^{12}$).

18. The compound of claim 17 selected from the group consisting of the following:
- 3-{3-Benzyl-5-[(N-methyl-phenylamino)-methylene]-4-oxothiazolidin-2-ylideneamino}-4-ethylamino-benzonitrile;
- 2-(5-acetyl-2-ethylamino-phenylimino)-3-benzyl-5-[(N-methyl-phenylamino)-methylene]-thiazolidin-4-one;
- 3-{3-benzyl-5-[(N-benzyl-methylamino)-methylene]-4-oxothiazolidin-2-ylideneamino}-4-ethylamino-benzonitrile;
- 2-(5-acetyl-2-ethylamino-phenylimino)-3-benzyl-5-[(N-benzyl-methylamino)-methylene]-thiazolidin-4-one;
- 3-(3-benzyl-5-[[N-(4-methoxyphenyl)-methylamino]methylene}-4-oxothiazolidin-2-ylideneamino)-4-ethylamino-benzonitrile;
- 2-(5-acetyl-2-ethylamino-phenylimino)-3-benzyl-5-{[N-(4-methoxyphenyl)-methylamino]-methylene}-thiazolidin-4-one;
- 3-(3-benzyl-5-{[N-(2-methoxyphenyl)-methylamino]-methylene}-4-oxothiazolidin-2-ylideneamino)-4-ethylamino-benzonitrile;
- 2-(5-acetyl-2-ethylamino-phenylimino)-3-benzyl-5-{[N-(3-methoxyphenyl)-methylamino]-methylene}-thiazolidin-4-one;
- 2-(5-acetyl-2-ethylamino-phenylimino)-3-benzyl-5-[(N-methyl-phenethylamino)-methylene]-thiazolidin-4-one;
- 2-(5-acetyl-2-ethylamino-phenylimino)-3-benzyl-5-({N-[4-(2-methoxy-ethoxy)-phenyl]-methylamino}-methylene)-thiazolidin-4-one;
- 3-{3-benzyl-5-[(4-methoxyphenylamino)-methylene]-4-oxothiazolidin-2-ylideneamino}-4-ethylamino-benzonitrile;
- 3-(3-benzyl-5-dimethylaminomethylene-4-oxothiazolidin-2-ylideneamino)-4-ethylamino-benzonitrile;
- 2-(5-acetyl-2-ethylamino-phenylimino)-3-benzyl-5-dimethylaminomethylene-thiazolidin-4-one; and
- 2-(5-acetyl-2-ethylamino-phenylimino)-3-benzyl-5-{[(3-dimethylaminopropyl)-methylamino]-methylene}-thiazolidin-4-one.

19. A pharmaceutical composition, comprising a pharmaceutically acceptable carrier and a compound of formula (I) of claim 1:

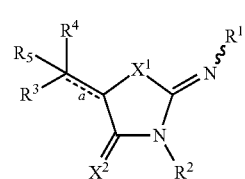

(I)

or a pharmaceutically acceptable derivative thereof, wherein:
$X^1$ is N$R^6$, O or S(O)$_t$;
$X^2$ is S or O;
$R^1$ is optionally substituted alkyl, optionally substituted alkenyl or optionally substituted alkynyl, all or which, when substituted, are substituted with one to five substituents each independently selected from the group consisting of cyano, nitro, halo, pseudohalo, —OR$^{10}$, —SR$^{16}$, —N(R$^{11}$)(R$^{12}$), —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_t$R$^{15}$ and —R$^9$—S(O)$_t$R$^{15}$;

or R$^1$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_t$R$^{15}$ and —R$^9$—S(O)$_t$R$^{15}$;

or R$^1$ is —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—N(R$^{10}$)C(J)R$^{13}$, —R$^9$—N(R$^{10}$)C(J)OR$^{10}$ or —R$^9$—N(R$^{10}$)C(J)N(R$^{11}$)(R$^{12}$);

R$^2$ is optionally substituted alkyl, optionally substituted alkenyl, optionally substituted alkynyl, all or which, when substituted, are substituted with one to five substituents each independently selected from the group consisting of cyano, nitro, halo, pseudohalo, —OR$^{10}$, —SR$^{16}$, N(R$^{11}$)(R$^{12}$), —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_t$R$^{15}$ and —S(O)$_t$R$^{15}$;

or R$^2$ is optionally substituted cycloalkyl, optionally substituted cycloalkylalkyl, optionally substituted heterocyclyl, optionally substituted heterocyclylalkyl, optionally substituted aryl, optionally substituted heteroaryl, optionally substituted aralkyl, optionally substituted heteroaralkyl or optionally substituted aryl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_t$R$^{15}$ and —R$^9$—S(O)$_t$R$^{15}$;

or R$^2$ is —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$) or —R$^9$—S(O)$_t$R$^{15}$;

R$^3$, R$^4$ and R$^5$ are each independently selected as in (a), (b) or (c) as follows:

(a) R$^3$, R$^4$ and R$^5$ are each independently optionally substituted alkyl, optionally substituted alkenyl or optionally substituted alkynyl, all of which, when substituted are substituted with cyano, nitro, halo, pseudohalo, —OR$^{10}$, —SR$^{16}$, —N(R$^{11}$)(R$^{12}$), —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_t$R$^{15}$ and —S(O)$_t$R$^{15}$;

or (b) R$^3$, R$^4$ and R$^5$ are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —R$^9$—OR$^{10}$, —R$^9$—SR$^{16}$, —R$^9$—N(R$^{11}$)(R$^{12}$), —R$^9$—C(J)R$^{13}$, —R$^9$—C(J)OR$^{10}$, —R$^9$—C(J)N(R$^{11}$)(R$^{12}$), —R$^9$—N(R$^{10}$)C(J)R$^{13}$, —R$^9$—N(R$^{10}$)C(J)OR$^{10}$, —R$^9$—N(R$^{10}$)C(J)N(R$^{11}$)(R$^{12}$), —R$^9$—OC(J)R$^{13}$, —R$^9$—OC(J)OR$^{10}$, —R$^9$—OC(J)N(R$^{11}$)(R$^{12}$), —Si(R$^{14}$)$_3$, —N(R$^{10}$)S(O)$_t$R$^{15}$ and —R$^9$—S(O)$_t$R$^{15}$;

or (c) R$^3$, R$^4$ and R$^5$ are each independently selected from a group consisting of hydrogen, —N(R$^7$)(R$^8$), —N(R$^{10}$)C(J)R$^{13}$, —N(R$^{10}$)C(J)OR$^{10}$, —R$^9$—C(J)R$^{13}$, —N(R$^{10}$)C(J)N(R$^{11}$)(R$^{12}$) and —N(R$^{10}$)S(O)$_t$R$^{15}$;

provided that R$^5$ is present only when bond a is a single bond;

and further provided that:

when R$^3$, R$^4$ or R$^5$ is cycloalkylalkyl or —N(R$^7$)(R$^8$) and bond a is a single bond, then R$^1$ is phenyl substituted with at least two different substituents selected from the following: cyano, —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{12}$)R$^{13}$, —R$^9$—N(R$^{10}$)C(J)OR$^{10}$, —R$^9$—N(R$^{10}$)C(J)N(R$^{11}$)(R$^{12}$), —N(R$^{10}$)S(O)$_t$R$^{13}$, —R$^9$—N(R$^{10}$)C(J)R$^{13}$, and —R$^9$—N(R$^{11}$)(R$^{12}$);

or when R$^3$, R$^4$ or R$^5$ is alkyl, alkenyl, alkynyl, halo, haloalkyl, cycloalkyl, heterocyclylalkyl, aralkyl, —R$^9$—C(J)R$^{13}$, —R$^9$—C(J)OR$^{10}$, —R$^9$—S(O)$_t$R$^{15}$, aryl or heteroaryl, then R$^1$ is phenyl and R$^1$ is substituted with at least two different substituents selected from the following: cyano, —R$^9$—C(J)R$^{13}$, —R$^9$—C(J)OR$^{10}$, —R$^9$—C(J)N(R$^{11}$)(R$^{12}$), —R$^9$—C(J)N(R$^{10}$)N(R$^{12}$)R$^{13}$, —R$^9$—N(R$^{10}$)C(J)OR$^{10}$, —R$^9$—N(R$^{10}$)C(J)N(R$^{11}$)(R$^{12}$), —N(R$^{10}$)S(O)$_t$R$^{13}$, —R$^9$—N(R$^{10}$)C(J)R$^{13}$, and —R$^9$—N(R$^{11}$)(R$^{12}$);

and further provided that R$^3$, R$^4$ and R$^5$ are not all hydrogen;

R$^6$ is hydrogen, alkyl, alkenyl, alkynyl, aryl, heteroaryl, cycloalkyl, heterocyclyl, aralkyl, heteroaralkyl, —R$^9$—S(O)$_t$R$^{15}$, —R$^9$—C(J)R$^{13}$, —R$^9$—C(J)OR$^{10}$ or —R$^9$—C(J)N(R$^{11}$)(R$^{12}$);

R$^7$ and R$^8$ each independently selected as in (a), (b) or (c) as follows:

(a) R$^7$ and R$^8$ are each independently optionally substituted alkyl, optionally substituted alkenyl or optionally substituted alkynyl, all of which, when substituted, are substituted with one to three substituents each independently selected from the group consisting of cyano, nitro, halo, pseudohalo, —OR$^{10}$, —SR$^{16}$, —N(R$^{11}$)(R$^{12}$), —OR$^{16}$OR$^{10}$, —C(J)R$^{13}$, —C(J)OR$^{10}$, —C(J)N(R$^{11}$)(R$^{12}$), —C(J)N(R$^{10}$)N(R$^{11}$)(R$^{12}$), —N(R$^{10}$)C(J)R$^{13}$, —N(R$^{10}$)C(J)OR$^{10}$, —N(R$^{10}$)C(J)N(R$^{11}$)(R$^{12}$), —OC(J)R$^{13}$, —OC(J)OR$^{10}$, —OC(J)N(R$^{11}$)(R$^{12}$), —Si(R$^{14}$)$_3$, —N(R$^{10}$)S(O)$_t$R$^{15}$ and —S(O)$_t$R$^{15}$;

or (b) $R^7$ and $R^8$ are are each independently optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl, all of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$OR^{16}OR^{10}$, —$R^9$—$SR^{16}$, —$R^9$—$N(R^{11})(R^{12})$, —$R^9$—$C(J)R^{13}$, —$R^9$—C(J)$OR^{10}$, —$R^9$—$C(J)N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$C(J)N(R^{10})N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$R^9$—$S(O)_tR^{15}$;

or (c) $R^7$ and $R^8$ are each independently hydrogen, —C(J)$R^{13}$, —C(J)$OR^{10}$, —C(J)$N(R^{11})(R^{12})$, —$N(R^{10})C(J)OR^{10}$ or —$S(O)_tR^{15}$ provided, however, that both $R^7$ and $R^8$ cannot be hydrogen;

or $R^7$ and $R^8$ together with the nitrogen atom to which they are attached, form an optionally substituted heterocyclyl or an optionally substituted heteroaryl, either of which, when substituted, are substituted with one to five substituents each independently selected from the group consisting of alkyl, haloalkyl, cycloalkyl, cycloalkylalkyl, heterocyclyl, heterocyclylalkyl, aryl, aralkyl, heteroaryl, heteroaralkyl, cyano, nitro, halo, pseudohalo, —$R^9$—$OR^{10}$, —$R^9$—$OR^{16}OR^{10}$, —$R^9$—$SR^{16}$, —$R^9$—$N(R^{11})(R^{12})$, —$R^9$—$C(J)R^{13}$, —$R^9$—$C(J)OR^{10}$, —$R^9$—$C(J)N(R^{11})(R^{12})$, —$R^9$—$C(J)N(R^{10})N(R^{11})(R^{12})$, —$R^9$—$N(R^{10})C(J)R^{13}$, —$R^9$—$N(R^{10})C(J)OR^{10}$, —$R^9$—$N(R^{10})C(J)N(R^{11})(R^{12})$, —$R^9$—$OC(J)R^{13}$, —$R^9$—$OC(J)OR^{10}$, —$R^9$—$OC(J)N(R^{11})(R^{12})$, —$Si(R^{14})_3$, —$N(R^{10})S(O)_tR^{15}$ and —$S(O)_tR^{15}$;

each $R^9$ is independently a direct bond or a straight or branched alkylene chain;

$R^{10}$ and $R^{13}$ are each independently hydrogen, alkyl, alkenyl, alkynyl, haloalkyl, cycloalkyl, cycloalkylalkyl, heterocyclyl, heterocyclylalkyl, aryl, aralkyl, heteroaryl or heteroaralkyl;

$R^{11}$ and $R^{12}$ are each independently hydrogen, alkyl, alkenyl, alkynyl, haloalkyl, cycloalkyl, cycloalkylalkyl, heterocyclyl, heterocyclylalkyl, aryl, aralkyl, heteroaryl or heteroaralkyl;

or $R^{11}$ and $R^{12}$ together with the nitrogen atom to which they are attached, form a heterocyclyl, heterocyclylalkenyl, or heteroaryl;

$R^{14}$, $R^{15}$ and $R^{16}$ are each independently alkyl, alkenyl, alkynyl, haloalkyl, cycloalkyl, cycloalkylalkyl, heterocyclyl, heterocyclylalkyl, aryl, aralkyl, heteroaryl or heteroaralkyl;

each J is independently O or S; and each t is independently 0 to 2.

20. The pharmaceutical composition of claim 19 wherein the pharmaceutical composition further comprises at least one additional active agent(s) selected from antihyperlipidemic agents, plasma HDL-raising agents, antihypercholesterolemic agents, cholesterol biosynthesis inhibitors, HMG CoA reductase inhibitors, acyl-coenzyme A cholesterol acytransferase (ACAT) inhibitors, probucol, raloxifene, nicotinic acid, niacinamide, cholesterol absorption inhibitors, bile acid sequestrants, low density lipoprotein receptor inducers, clofibrate, fenofibrate, benzofibrate, cipofibrate, gemfibrizol, vitamin $B_6$, vitamin $B_{12}$, vitamin C, vitamin E, β-blockers, anti-diabetes agents, sulfonylureas, biguanides, thiazolidinediones, activators of PPARα, PPARβ, and PPARγ, dehydroepiandrosterone, antiglucocorticoids, TNFα inhibitors, α-glucosidase inhibitors, pramlintide, amylin, insulin, angiotensin II antagonists, angiotensin converting enzyme inhibitors, platelet aggregation inhibitors, fibrinogen receptor antagonists, LXR α agonists, antagonists or partial agonists, LXR β agonists, antagonists or partial agonists, phenylpropanolamine, phentermine, diethylpropion, mazindol, fenfluramine, dexfenfluramine, phentiramine, $β_3$ adrenoceptor agonist agents, sibutramine, gastrointestinal lipase inhibitors, neuropeptide Y, enterostatin, cholecytokinin, bombesin, amylin, histamine $H_3$ receptor agonists or antagonists, dopamine $D_2$ receptor agonists or antagonists, melanocyte stimulating hormone, corticotrophin releasing factor, leptins, galanin or gamma amino butyric acid (GABA), aspirin or fibric acid derivatives.

21. A compound or pharmaceutically acceptable derivative of claim 1, selected from the group consisting of 4-(ethylamino)-3-{[(2Z,5Z)-5-{[methyl(phenyl)amino]methylidene}-4-oxo-3-(phenylmethyl)-1,3-thiazolidin-2-ylidene]amino}benzonitrile;

(2Z,5Z)-2-{[5-acetyl-2-(ethylamino)phenyl]imino}-5-{[methyl(phenyl)amino]methylidene}-3-(phenylmethyl)-1,3-thiazolidin-4-one;

4-(ethylamino)-3-{[(2Z,5Z)-5-{[methyl(phenylmethyl)amino]methylidene}-4-oxo-3-(phenylmethyl)-1,3-thiazolidin-2-ylidene]amino}benzonitrile;

(2Z,5Z)-2-{[5-acetyl-2-(ethylamino)phenyl]imino}-5-{[methyl(phenylmethyl)amino]methylidene}-3-(phenylmethyl)-1,3-thiazolidin-4-one;

3-{[(2Z,5Z)-5-(2,3-dihydro-1H-indol-1-ylmethylidene)-4-oxo-3-(phenylmethyl)-1,3-thiazolidin-2-ylidene]amino}-4-(ethylamino)benzonitrile;

(2Z,5Z)-2-{[5-acetyl-2-(ethylamino)phenyl]imino}-5-(2,3-dihydro-1H-indol-1-ylmethylidene)-3-(phenylmethyl)-1,3-thiazolidin-4-one;

(2Z,5Z)-2-[(3-acetylphenyl)imino]-5-(2,3-dihydro-1H-indol-1-ylmethylidene)-3-(furan-2-ylmethyl)-1,3-thiazolidin-4-one;

N-(4-{[(2Z,5Z)-5-(2,3-dihydro-1H-indol-1-ylmethylidene)-3-(furan-2-ylmethyl)-4-oxo-1,3-thiazolidin-2-ylidene]amino}phenyl)acetamide;

3-{[(2Z,5Z)-5-[(dimethylamino)methylidene]-4-oxo-3-(phenylmethyl)-1,3-thiazolidin-2-ylidene]amino}-4-(ethylamino)benzonitrile;

(2Z,5Z)-2-{[5-acetyl-2-(ethylamino)phenyl]imino}-5-[(dimethylamino)methylidene]-3-(phenylmethyl)-1,3-thiazolidin-4-one;

4-(ethylamino)-3-{[(2Z,5Z)-5-({[4-(methyloxy)phenyl]amino}methylidene)-4-oxo-3-(phenylmethyl)-1,3-thiazolidin-2-ylidene]amino}benzonitrile;

4-(ethylamino)-3-{[(2Z,5Z)-5-({methyl[4-(methyloxy)phenyl]amino}methylidene)-4-oxo-3-(phenylmethyl)-1,3-thiazolidin-2-ylidene]amino}benzonitrile;

(2Z,5Z)-2-{[5-acetyl-2-(ethylamino)phenyl]imino}-5-({methyl[4-(methyloxy)phenyl]amino}methylidene)-3-(phenylmethyl)-1,3-thiazolidin-4-one;

4-(ethylamino)-3-{[(2Z,5Z)-5-({methyl[2-(methyloxy)phenyl]amino}methylidene)-4-oxo-3-(phenylmethyl)-1,3-thiazolidin-2-ylidene]amino}benzonitrile;

(2Z,5Z)-2-{[5-acetyl-2-(ethylamino)phenyl]imino}-5-({methyl[3-(methyloxy)phenyl]amino}methylidene)-3-(phenylmethyl)-1,3-thiazolidin-4-one;

(2Z,5Z)-2-{[5-acetyl-2-(ethylamino)phenyl]imino}-5-{[methyl(4-{[2-(methyloxy)ethyl]oxy}phenyl)amino]methylidene}-3-(phenylmethyl)-1,3-thiazolidin-4-one;

(2Z,5Z)-2-{[5-acetyl-2-(ethylamino)phenyl]imino}-5-[(4-methylpiperazin-1-yl)methylidene]-3-(phenylmethyl)-1,3-thiazolidin-4-one;

(2Z,5Z)-2-{[5-acetyl-2-(ethylamino)phenyl]imino}-5-({[3-dimethylamino)propyl](methyl)amino}methylidene)-3-(phenylmethyl)-1,3-thiazolidin-4-one;

(2Z,5Z)-2-{[5-acetyl-2-(ethylamino)phenyl]imino}-5-{[methyl(2-phenylethyl)amino]methylidene}-3-(phenylmethyl)-1,3-thiazolidin-4-one;

(2Z)-2-{[5-acetyl-2-(ethylamino)phenyl]imino}-3,5-bis(phenylmethyl)-1,3-thiazolidin-4-one;

(2Z)-2-{[5-acetyl-2-(ethylamino)phenyl]imino}-5-(2-phenylethyl)-3-(phenylmethyl)-1,3-thiazolidin-4-one;

(2Z)-2-{[5-acetyl-2-(ethylamino)phenyl]imino}-5-(2-oxo-2-phenylethyl)-3-(phenylmethyl)-1,3-thiazolidin-4-one;

(2Z,5Z)-2-{[5-acetyl-2-(ethylamino)phenyl]imino}-3-(phenylmethyl)-5-(phenylmethylidene)-1,3-thiazolidin-4-one; and (2Z,5Z)-2-{[5-acetyl-2-(ethylamino)phenyl]imino}-5-(furan-2-ylmethylidene)-3-(phenylmethyl)-1,3-thiazolidin-4-one.

\* \* \* \* \*